United States Patent
Spaid et al.

(10) Patent No.: US 7,040,144 B2
(45) Date of Patent: May 9, 2006

(54) MICROFLUIDIC VISCOMETER

(75) Inventors: Michael Spaid, Sunnyvale, CA (US); Andrea W. Chow, Los Altos, CA (US); Benjamin N. Wang, Cambridge, MA (US); Ring-Ling Chien, San Jose, CA (US); J. Wallace Parce, Palo Alto, CA (US); Anne R. Kopf-Sill, Portola Valley, CA (US); Josh Molho, Fremont, CA (US); Anubhav Tripathi, Fremont, CA (US); Matthew B. Kerby, Belmont, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 117 days.

(21) Appl. No.: 10/207,735

(22) Filed: Jul. 26, 2002

(65) Prior Publication Data
US 2003/0041652 A1   Mar. 6, 2003

Related U.S. Application Data

(63) Continuation-in-part of application No. 10/008,604, filed on Nov. 9, 2001, now Pat. No. 6,681,616, which is a continuation-in-part of application No. 09/792,435, filed on Feb. 23, 2001, now Pat. No. 6,915,679.

(60) Provisional application No. 60/216,793, filed on Jul. 7, 2000, provisional application No. 60/184,390, filed on Feb. 23, 2000.

(51) Int. Cl.
*G01N 11/04* (2006.01)
*G01F 1/708* (2006.01)

(52) U.S. Cl. .................. 73/54.05; 73/54.07; 73/861.05
(58) Field of Classification Search ............... 73/54.05, 73/54.07, 54.08, 861.05
See application file for complete search history.

(56) References Cited

U.S. PATENT DOCUMENTS

| | | | |
|---|---|---|---|
| 5,304,487 A | | 4/1994 | Wilding et al. |
| 5,573,651 A | | 11/1996 | Dasgupta et al. |
| 5,661,232 A | * | 8/1997 | Van Cleve et al. ........ 73/54.05 |
| 5,858,195 A | | 1/1999 | Ramsey |
| 5,863,801 A | | 1/1999 | Southgate et al. |
| 5,885,470 A | | 3/1999 | Parce et al. |
| 5,942,443 A | | 8/1999 | Parce et al. |
| 5,965,001 A | | 10/1999 | Chow et al. |
| 5,979,868 A | | 11/1999 | Wu et al. |
| 6,001,229 A | | 12/1999 | Ramsey |
| 6,001,231 A | * | 12/1999 | Kopf-Sill .................... 204/454 |

(Continued)

FOREIGN PATENT DOCUMENTS

WO    WO-94/05414 A1    3/1994

(Continued)

OTHER PUBLICATIONS

Gambos and Forester (1998) "An Optical Micro-fluidic Viscometer." *MAMS* 66:187-191.

(Continued)

*Primary Examiner*—Hezron Williams
*Assistant Examiner*—John C. Hanley
(74) *Attorney, Agent, or Firm*—Donald R. McKenna; Ann C. Petersen

(57) ABSTRACT

Microfluidic devices, systems, and methods measure viscosity, flow times, and/or pressures, other flow characteristics within the channels, and the measured flow characteristics can be used to generate a desired flow. Multi-reservoir pressure modulator and pressure controller systems, electrokinetic systems and/or other fluid transport mechanisms can generate the flow, controllably mix fluids, and the like.

8 Claims, 39 Drawing Sheets

U.S. PATENT DOCUMENTS

| | | | |
|---|---|---|---|
| 6,062,261 | A | 5/2000 | Jacobson et al. |
| 6,076,392 | A | 6/2000 | Drzewiecki |
| 6,110,343 | A | 8/2000 | Ramsey et al. |
| 6,134,950 | A | 10/2000 | Foster et al. |
| 6,146,103 | A * | 11/2000 | Lee et al. .................... 417/50 |
| 6,149,787 | A | 11/2000 | Chow et al. |
| 6,156,181 | A | 12/2000 | Parce et al. |
| 6,231,737 | B1 | 5/2001 | Ramsey et al. |
| 6,235,175 | B1 | 5/2001 | Dubrow et al. |
| 6,235,471 | B1 | 5/2001 | Knapp et al. |
| 6,267,858 | B1 | 7/2001 | Parce et al. |
| 6,272,905 | B1 | 8/2001 | Drzewiecki |
| 6,506,609 | B1 | 1/2003 | Wada et al. |
| 6,592,821 | B1 | 7/2003 | Wada et al. |

FOREIGN PATENT DOCUMENTS

| | | |
|---|---|---|
| WO | WO-97/02357 A1 | 1/1997 |
| WO | WO 00/10015 A1 | 2/2000 |
| WO | WO 00/45172 | 8/2000 |
| WO | WO 01/06370 A1 | 8/2001 |

OTHER PUBLICATIONS

Chien, R-L, et al. "Multiport flow-control system for Lab-on-a-chip microfluidic devices" *Fresenius J. Anal. Chem.* (2001) 371:106-111.

Dasgupta, et al., "Electroosmosis: A Reliable Fluid Propulsion System for Flow Injection Analysis," *Anal Chem.*, (1994) 66: 1792-1798.

Jacobson, et al., "Effects of Injection Schemes and Column Geometry on the Performance of Microchip Electrophoresis Devices," *Anal Chem.* (1994) 66: 1107-1113.

Manz, et al., "Miniaturized Total Chemical Analysis Systems: A Novel Concept for Chemical Sensing," *Sensors and Actuators* (1990) B1: 244-248.

Sandoval, et al., "Method for the Accelerated Measurement of Electroosmosis in Chemically Modified Tubes for Capillary Electrophoresis," *Anal Chem.* (1996) 68: 2771-2775.

* cited by examiner

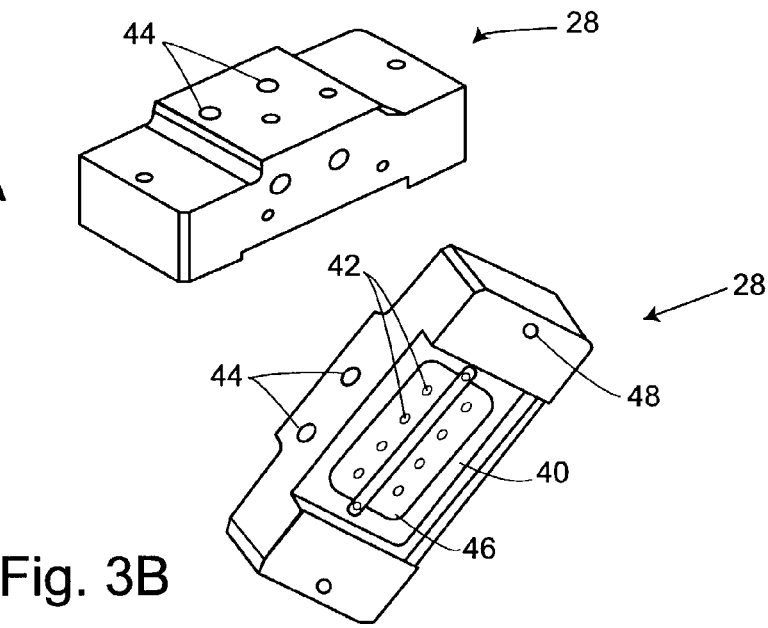
Fig. 3A
Fig. 3B
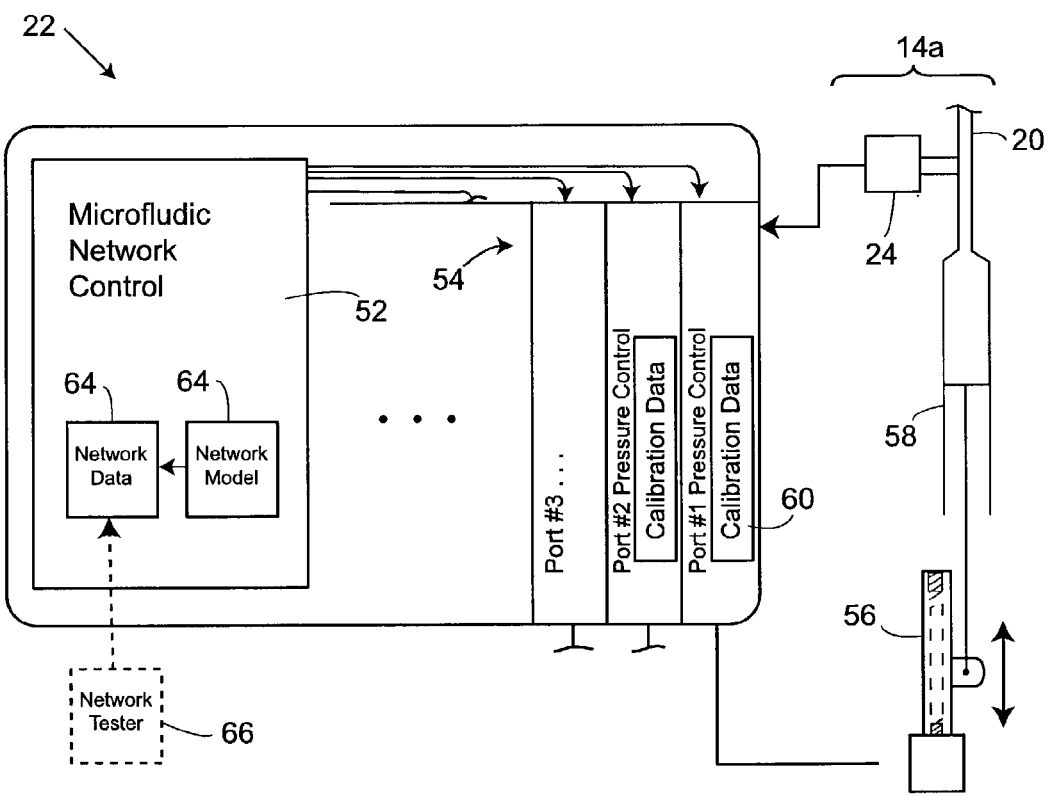
Fig. 4

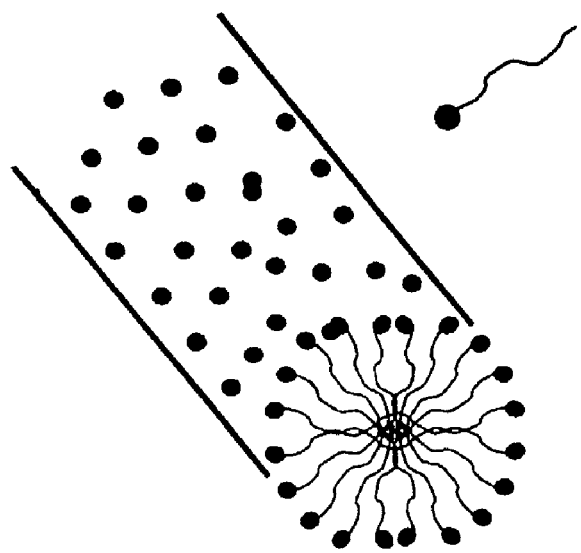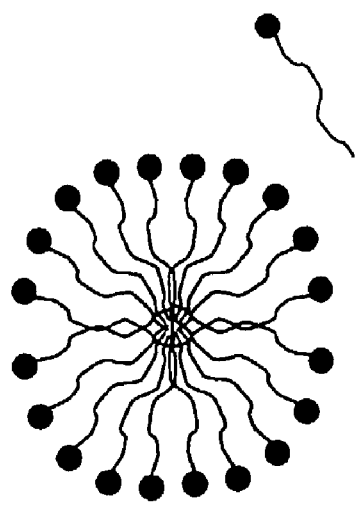
Fig. 40

MICROFLUIDIC VISCOMETER

CROSS-REFERENCES TO RELATED APPLICATIONS

This application is a continuation-in-part of U.S. application Ser. No. 10/008,604, filed Nov. 9, 2001, now U.S. Pat. No. 6,681,616, issued Jan. 27, 2004, which is a continuation-in-part of U.S. application Ser. No. 09/792,435 filed on Feb. 23, 2001 now U.S. Pat. No. 6,915,679. This application claims priority to and benefit of these prior applications. This application also claims the benefit of and priority to U.S. Provisional Patent Application No. 60/216,793 filed on Jul. 7, 2000, and U.S. Provisional Patent Application No. 60/184,390 filed Feb. 23, 2000. The full disclosures of each of these prior applications are incorporated herein by reference.

BACKGROUND OF THE INVENTION

The present invention is generally related to analytical tools for the biological and chemical sciences, and in a particular embodiment, provides microfluidic devices, systems, and methods for determining the viscosity of fluids within microfluidic channels of a microfluidic network, optionally without adding dye (or other agents) which can alter the properties of the fluids.

Microfluidic systems are now in use for the acquisition of chemical and biological information. These microfluidic systems are often fabricated using techniques commonly associated with the semiconductor electronics industry, such as photolithography, wet chemical etching, and the like. As used herein, "microfluidic" means a system or device having channels and chambers which are at the micron or submicron scale, e.g., having at least one cross-sectional dimension in a range from about 0.1 µm to about 500 µm.

Applications for microfluidic systems are myriad. Microfluidic systems have been proposed for capillary electrophoresis, liquid chromatography, flow injection analysis, chemical reaction and synthesis, and many other uses. Microfluidic systems also have wide ranging applications in rapidly assaying compounds for their effects on various chemical, and, preferably, biochemical systems. These interactions include the full range of catabolic and anabolic reactions which occur in living systems, including enzymatic, binding, signaling, and other reactions.

A variety of methods have been described to effect the transport of fluids between a pair of reservoirs within a microfluidic system or device. Incorporation of mechanical micro pumps and valves within a microfluidic device has been described to move the fluids within a microfluidic channel. The use of acoustic energy to move fluid samples within a device by the effects of acoustic streaming has been proposed, along with the use of external pumps to directly force liquids through microfluidic channels.

The capabilities and use of microfluidic systems advanced significantly with the advent of electrokinetics: the use of electrical fields (and the resulting electrokinetic forces) to induce flow of fluid materials through the channels of a microfluidic system. Electrokinetic forces have the advantages of direct control, fast response, and simplicity, and allow fluid materials to be selectively moved through a complex network of channels so as to provide a wide variety of chemical and biochemical analyses. An exemplary electrokinetic system providing variable control of electroosmotic and/or electrophoretic forces within a fluid-containing structure is described in U.S. Pat. No. 5,965,001, the full disclosure of which is incorporated herein by reference.

Despite the above-described advancements in the field of microfluidics, as with all successes, still further improvements are desirable. For example, while electrokinetic material transport systems provide many benefits in the microscale movement, mixing, and aliquoting of fluids, the application of electrical fields can have detrimental effects in some instances. In the case of charged reagents, electrical fields can cause electrophoretic biasing of material volumes, e.g., highly charged materials moving to the front or back of a fluid volume. Where transporting cellular material is desired, elevated electrical fields can, in some cases, result in a perforation or electroporation of the cells, which can effect their ultimate use in the system.

To mitigate the difficulties of electrokinetic systems, simplified transport systems for time domain multiplexing of reagents has been described in WO 00/45172 (assigned to the assignee of the present invention), the full disclosure of which is incorporated herein by reference. Still further alternative fluid transport mechanisms and control methodologies to enhance the flexibility and capabilities of known microfluidic systems, including multiple modulated pressure-driven techniques, have been described in International Application No. PCT/US01/05960, the full disclosure of which is also incorporated herein by reference.

Regardless of the mechanism used to effect movement of fluid and other materials within a microfluidic channel network, accuracy and repeatability of microfluidic flows can be problematic. Quality control can be challenging in light of variability of the fluids making up these flows, and accurate control over microfluidic flows in applications such as high throughput screening would benefit significantly from stable and reliable assays. It would also be beneficial to determine additional characteristics of the fluids flowing within the microfluidic channels of a microfluidic network.

In light of the above, it would be advantageous to provide improved microfluidic devices, systems, and methods. It would be desirable if these improved techniques allowed better control over the flows within a microfluidic network, and/or increased the information provided by the microfluidic systems regarding one or more of the characteristics of the fluids flowing within a microfluidic channel of the network. It would be particularly beneficial if these enhanced techniques provided real-time and/or quality control feedback on the actual flows, ideally without relying on significantly increased system complexity or cost.

SUMMARY OF THE INVENTION

The present invention generally provides improved microfluidic devices, systems, and methods. The devices and systems of the invention generally allow the characteristics of a fluid within a microfluidic system to be determined, often using high-throughput techniques. In many embodiments, the devices and systems will determine the viscosity of one or more sample fluids within a microfluidic channel network of a microfluidic body. The microfluidic networks generally include at least one flow-resisting channel segment, and viscosity can be determined by flowing the sample fluid through the channel segment, often without altering the sample viscosity, by adding any detectable marker (such as fluorescent dyes or the like) to the fluid before it flows through the channel segment. These techniques can also allow the use of dyes which are not normally compatible with a particular sample fluid, for example, dyes which are not soluble or the like. The viscosity can be determined by mixing the sample fluid with a detectable marker at an intersection downstream of the flow-resisting channel segment, with the mixing characteristics at the intersection indicating the pressure drop along the channel segment (and hence the viscosity of the sample fluid). Viscosities can be determined by comparing the flow characteristics of the sample fluid with a reference fluid having a known viscosity. The sensing range can be enhanced using a plurality of flow-resisting channel segments and/or detectable fluid channel intersections.

In a first aspect, the invention provides a microfluidic viscometer system comprising a microfluidic channel network including a first flow-resisting channel segment. A sensor coupled to the first segment of the network determines a viscosity of a sample fluid therein.

In many embodiments, a body having channel walls defines the network. The network can include a plurality of channels with one or more intersections therebetween. A flow generator (e.g., a pressure or voltage source) coupled to the network can induce a flow of the sample fluid within the first segment. A first intersection can be in communication with the first segment, with the sensor coupled to the network at a sensor location disposed downstream of the first segment. This allows the sensor to sense a change in the flow which propagates from the first intersection to the sensor location so as to determine the viscosity of the sample fluid.

In some embodiments, the change in flow comprises a pulse of a detectable fluid introduced at the first intersection, which is optionally upstream of the first segment. The system can then determine the viscosity of the sample fluid using steady state propagation of the flow (which includes the detectable fluid pulse) from the intersection through the first segment and to the sensor location. In such embodiments, it is possible that the presence of the detectable fluid pulse can, to some extent, alter the characteristics (including the viscosity) of the sample fluid flowing through the first segment. Related embodiments can make use of a step-function change in flow of a detectable fluid.

In alternative embodiments, the first segment is optionally disposed upstream of the first intersection. The flow defines a ratio between a quantity of a sample fluid in the flow and a quantity of a detectable fluid in the flow, the detectable fluid being detectable by the sensor and traversing a second flow-resisting channel segment between a detectable fluid source and the intersection. By monitoring the changes in the mixing ratio, typically by monitoring the strength of a detectable signal provided from the mixed flow, a processor coupled to the sensor can determine the viscosity of the sample fluid. Advantageously, the viscosity sensing techniques of the present invention are particularly well-suited for sequential viscosity measurements of a plurality of sample fluids, particularly when the fluids are transferred along a fluid introduction channel in the form of a capillary extending or protruding from the microfluidic body.

The microfluidic systems of the invention can include, e.g., a channel split to a pair of channels having different hydrodynamic resistance, wherein a fluid can flow for detection of a transit time differential related to the viscosity of the fluid. A first segment, with an upstream end, a downstream end, can be intersected at each end by a second flow-resisting segment with a different hydrodynamic resistance. The system can include, e.g., an instruction set to compare transit times of a fluid through the first segment and the second segment for determination of a fluid viscosity.

The microfluidic systems of the invention can optionally be provided with a side channel pressure sensor to measure pressures at any point along a channel. For example, a side channel segment can run between a side channel well and an intersection with a channel intersection where a pressure is to be measured. A detector can be coupled to the side channel segment to detect flow (or zero-flow). A pressure sensor can be coupled, e.g., to the side channel well to measure a side channel well pressure and the pressure at the channel intersection, e.g., when zero-flow conditions have been established in the side channel segment.

In another embodiment of the systems of the invention for determination of fluid viscosity, e.g., a sample fluid channel and reference fluid channel can be connected by a common diluent fluid channel so that the relative viscosity of a sample and reference can be compared. A sample fluid containing flow-resisting channel can be, e.g., in fluid contact with a reference fluid containing channel through a diluent channel. The a diluent fluid can include, e.g., a detectable marker detectable by sensors coupled to the sample channel and/or the reference channel. The system of this embodiment can provide, e.g., pressure, timing and/or detectable marker quantity output values that can be used to calculate sample fluid viscosity.

A further embodiment of microfluidic viscometer system of the invention directs reference and sample fluids to flow together at a T-intersection resulting in a non-mixing interface with a location that reflects the relative viscosities of the two fluids. The system includes, e.g., a sample fluid channel, a reference fluid channel, and a detector channel that come together in a T-intersection. A detector is coupled to the detector channel to detect, e.g., the location of the a fluid interface within the detector channel. Fluid channels can have, e.g., pressure detectors (such as readout from a multiport pressure manifold system) to report pressure levels, e.g., required to center the interface in the detector channel. Such values can be input to formulas for calculations of fluid viscosity.

In one aspect of the systems of the invention, viscoelasticity can be measured, e.g., by inducing an oscillating flow into a sample channel and detecting resultant marker concentration oscillations of sample co-flowing with a reference fluid in a detection channel. A microfluidic viscoelasticity measurement system can include, e.g., a sample fluid channel in fluid contact with a flow generator for induction of an oscillating sample fluid flow, a reference fluid channel in fluid contact with the sample fluid channel at an intersection, a detector channel in fluid contact with the sample channel and the reference channel at the intersection, and a detector coupled to the detector channel. The detector can be configured, e.g., to detect oscillations in the amount of detectable marker a fluid. An instruction set can be configured, e.g., to determine a phase shift between a fluid oscillation and a detectable marker oscillation for determination of a fluid viscoelasticity.

In a method aspect, the invention comprises determining a viscosity of a sample fluid. The method comprises altering a flow of a flow-restricting microfluidic channel segment. The viscosity of the sample fluid can be determined, e.g., by monitoring the altered flow.

In many embodiments, a first flow of a reference fluid through the flow-resisting channel will be monitored, the reference fluid having a known viscosity. A second flow through the flow-resisting channel will also be monitored, the second flow comprising the sample fluid. The viscosity of the sample fluid is optionally determined at least in part by comparing the first and second flows, with calculations based in part on the known viscosity of the reference fluid. The first and second flows can be monitored by a sensor disposed downstream of the flow-resisting channel with an intersection disposed between the flow resisting channel and the sensor. The flows can be monitored, e.g., by sensing a ratio of the sample fluid to a detectable fluid. Advantageously, a plurality of sample fluids can be sequentially transferred to the flow-resisting channel segment, allowing the viscosities of the samples to be determined in a high-throughput manner. In some embodiments, fluids are dispensed and/or mixed within a microfluidic network, for example, allowing viscosities of fluid mixtures to be determined as a function of their composition.

In another aspect, the invention comprises a microfluidic channel network including a first flow-resisting channel segment. A sensor is coupled to the network for sensing flows through the first segment. A processor is coupled to the sensor. The processor derives a viscosity of a sample fluid by comparing first and second flows through the first segment.

The system can further include a reference fluid disposed within the network. The first flow can comprise the reference fluid, and the second flow can comprise the sample fluid. In many embodiments, the second flow within the first segment is substantially composed of the sample fluid. The processor can calculate the viscosity of the sample fluid based at least in part on a viscosity of the reference fluid.

In many embodiments, a second flow-resisting channel segment is coupled to the first segment at a first intersection. A first detectable fluid can be disposed within the second segment. The first intersection can be downstream of the first segment, and the sensor can monitor the flow through the first segment by sensing a quantity of the first detectable fluid added to the flow at the first intersection. Still further additional flow resisting channel segments can be coupled to the first segment by additional intersections. The intersections can optionally be separated by associated flow-resisting channel segments, and the sensor can monitor the flow by sensing a quantity of the first detectable fluid added to the flow at the intersection. Alternatively, one or more additional flow-resisting channel segments can be coupled to the first segment, with the sensor monitoring the flow through the first segment by sensing a quantity of a second detectable fluid added to the flow through the third segment. In such embodiments, the second and third segments can have differing resistances to flows therein. The first and second detectable fluids can be independently detectable by the sensor, for example, comprising dyes having differing color (or other detectable markers) signatures.

The first segment can comprise a channel having a locally enhanced resistance to flows therein. For example, the channel region can have a reduced cross-sectional dimension, such as a reduced depth, a reduced width, or the like. Alternatively, a flow occluding structure can be disposed within the channel.

The first flow optionally comprises a reference fluid having a known viscosity, and the second flow optionally comprises a combination of the sample fluid and a detectable fluid. This combination can define a ratio, with the processor identifying the ratio from a signal produced by the sensor. For example, the sensor can sense a light signal generated by a fluorescent dye of the detectable fluid, with a relative strength of the fluorescence indicating the ratio.

In many embodiments, the processor derives the viscosity of the sample fluid by determining a rate of change of a signal generated by the sensor. In some embodiments, the processor derives the viscosity of the sample fluid by determining a magnitude of a change of a signal generated by the sensor. The processor can determine the sample viscosity throughout a range of at least about two orders of magnitude of cp (centipoise) units, preferably through a range of at least three orders of magnitude of cp units. The processor can determine the sample viscosity throughout at least a range from about 1 cp to 100 cp, preferably from about 1 cp to 1000 cp, and optionally from 0.1 cp to 1000 cp. By, for example, simply altering driving pressures, larger viscosities are sensed, i.e., 1,000 cp–100,000 cp. Hence, at least viscosities throughout ranges of at least 2 or 3 orders of magnitude can be sensed using the systems of this embodiment.

A microfluidic system optionally includes a sample fluid source which includes a plurality of sample fluids and a sample fluid introduction channel. The sample fluids can then be sequentially transferable along the fluid introduction channel to the flow resisting channel so as to sequentially determine viscosities of the sample fluid. The sample introduction channel optionally comprises a capillary extending from the microfluidic body, with the capillary being extendable sequentially (or with multiple capillaries in parallel) into the sample fluids. Generally, the capillary will have significantly less resistance to flow than the first segment.

In yet another embodiment, the invention provides a microfluidic system comprising a microfluidic body having a network of channels. A flow generator induces a flow within the network, and a sensor transmits a signal indicating a time of the flow. A processor effects feedback control of the flow in response to the time signal. Optionally, the processor can determine a viscosity for use in the feedback control loop.

Yet another embodiment of the invention provides a microfluidic system comprising first and second immiscible fluids. A microfluidic body having a network of channels combines the fluids therein, and a sensor is coupled to the network so as to define a viscometer. The viscometer measures interfacial properties of the combined fluid.

A method for determining the viscosity of a sample fluid can include, e.g., flowing the sample fluid through two or more microfluidic channel segments of different hydrodynamic resistance, and monitoring the difference in transit times of sample fluid in the channels so that the viscosity of the sample fluid can be determined based in part on the difference in transit times. The method can optionally include, e.g., comparing the difference in transit times of the sample fluid to the difference in transit times for a reference fluid of known viscosity for viscosity determinations based in part on the known viscosity of the reference fluid.

An alternative method of the invention for determining the viscosity of a sample fluid can be based, e.g., on parameters affecting the location of a non-mixed sample fluid/reference fluid interface flowing in a detection channel. The method can include, e.g., flowing the sample fluid in a first microfluidic channel, flowing the reference fluid in a second microfluidic channel converging with the first channel at a T-intersection, to form a non-mixed interface flowing from the T-intersection into a third micro channel. The location of the interface in the third channel can be adjusted by manipulating the forces inducing flow of the fluids. The viscosity of the sample fluid can be determined based in part, e.g., on the difference in pressures between the first and second channels, and on the known viscosity of the reference fluid.

In other embodiments, methods of the invention can include determining the viscosity, e.g., of a sample fluid flowing in one microfluidic channel relative to a reference standard flowing in another microfluidic channel, where both micro channels are in fluid contact with a diluent channel containing a detectable marker. For example, the method can comprise flowing the reference fluid of known viscosity in a reference channel intersected by the diluent channel, flowing the sample fluid in the sample channel intersected by the diluent channel, flowing the diluent fluid into the reference and/or sample channels, and detecting the diluent fluid in the sample and/or reference channels. The viscosity of the sample fluid can be determined, e.g., based on output values, such as the relative amounts of detectable marker in the sample and reference streams, the relative time required for a detectable marker pulse to travel with the sample and reference fluids to a detector, and/or the relative pressures required to induce a detectable marker pulse to simultaneously traverse the reference and sample channels. In one embodiment, the viscosity of the sample fluid can be determined based on the difference in amounts of detectable marker detected in the sample channel and the reference channel given equivalent flow inducing pressures. In another embodiment, a pulse of detectable marker can be injected from the diluent channel into the sample and reference channels, the travel times of the pulse in the two channels measured, and the viscosity of the sample fluid determined based on the travel time difference for the pulses in the two channels. In still another embodiment, the methods can include monitoring pressures inducing flow in the sample and reference channels, injecting a pulse of detectable marker from the diluent channel into the channels, and determining the viscosity of the sample fluid based in part on the difference in pressures used to induce flow in the two channels.

The present invention provides methods for determining, e.g., the kinematic viscosity and/or the mass-percent composition of a fluid admixed in a microfluidic system with one or more other fluids. The method can include, e.g., flowing one or more fluids into a microfluidic channel, setting a side channel pressure on a side channel intersecting the microfluidic channel at a first location to provide a zero-flow condition in the side channel to determine the intersection pressure, and determining the pressure difference between the intersection pressure and the microfluidic channel pressure at a second location, thereby providing parameters for determination of the viscosity or mass-percent composition of the fluid mixture. Setting the side channel pressure can comprise detecting a marker in a side channel fluid, and adjusting the side channel pressure to provide unchanging detection of the marker to provide a zero-flow condition wherein a pressure measured at the side well is an indirect measure of the pressure at the intersection. The detector of a zero-flow condition on the side channel can be configured to measure conductivity, fluorescence, light absorption, refraction, and/or the like.

The present invention provides methods for determining the viscoelasticity of a sample fluid. The method can include, e.g., flowing a reference fluid in a reference microfluidic channel which intersects a sample microfluidic channel to flow into a common detector channel. An oscillating flow of sample fluid can be, e.g., induced in the sample channel by a flow generator to flow into the detector channel. The sample fluid and/or reference fluid can contain, e.g., a detectable marker. Oscillations in the amount of detectable marker can result, e.g., in the detector channel, which can be compared to the flow oscillations induced by the flow generator in the sample fluid to determine a phase shift between the induced and detected oscillations. The viscoelasticity of the sample fluid can thereby be calculated based in part on the phase shift.

BRIEF DESCRIPTION OF THE DRAWINGS

FIGS. 3A and 3B are perspective views of a pressure manifold for releasably sealing reservoirs of the microfluidic device of channel 2 in fluid communication with the pressure modulators of the system of FIG. 1.

FIG. 4 schematically illustrates a control system for independently varying reservoir pressures in the microfluidic system of FIG. 1.

FIG. 8 illustrates the reaction, FIG. 8A is a titration curve for different substrate concentrations, FIG. 8B is a plot of the corrected signal verses substrate concentration, FIG. 8C is a plot for determination of the Michaelis constant, and FIG. 8D is a substrate titration plot.

FIGS. 13A, 13B, and 13C schematically illustrate microfluidic networks and method for imposing detectable signals on a microfluidic flow for measurement of flow characteristics which can be used to calculate pressures to affect a desired flow, for viscometry, and the like.

FIG. 40 schematically illustrates a surfactant micellar phase change that can affect fluid viscoelasticity.

DESCRIPTION OF THE SPECIFIC EMBODIMENTS

Figure 1:
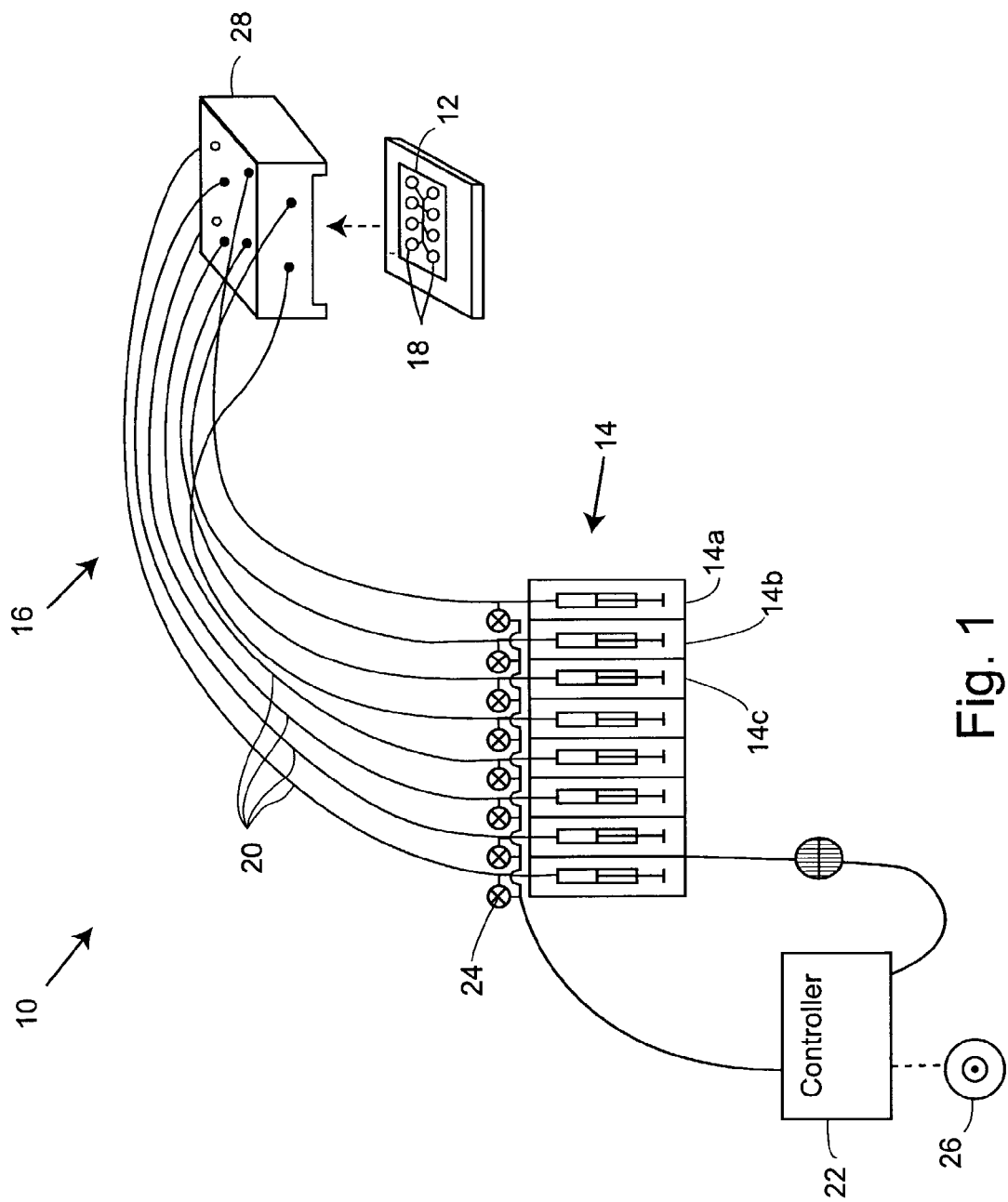
FIG. 1 schematically illustrates a microfluidic system having a multi-reservoir pressure modulation system according to the principles of the present invention.

The present invention will provide improved microfluidic devices, systems, and methods. The systems of the present invention will often determine a viscosity (or other characteristics) of a sample fluid by making use of the resistance to flow present within the small channels of a microfluidic network. Viscosities can be determined without, for example, adding fluorescent dyes or other detectable substances in a manner which could alter or distort the indicated viscosity. Toward that end, the fluid sample can flow through a flow resisting channel while sample fluid is substantially free of a substance which is detectable to the sensor.

As used herein, a sample is "substantially free" of a detectable substance if an associated viscosity sensor does not receive a sufficient signal from the detectable substance so as to identify the presence or speed of the detectable substance. It should be noted that such detectable substances can be, and often are, added to the sample fluid flow downstream of the flow-resisting channel segment. Nonetheless, as it flows through the flow-resisting channel segment (and hence as its viscosity is measured) the fluid can still be substantially free of the detectable substance. As used herein, a sensor having a detection region in fluid communication with a microfluidic network (or some component thereof) is encompassed within the term "a sensor coupled to" the microfluidic network (or component thereof).

Preferably, viscosities of fluid samples of no more than about 30 µl can be determined, ideally providing viscosities with fluid samples volumes of less than 5 µl. In fact, only a few (about 3 or more) nanoliters of a sample fluid can be brought into the network, so that viscosities of this quantity of fluid or more can be determined in some embodiments, with many embodiments able to measure as little as 10 nanoliters, typically allowing samples of 100 nanoliters or more to be measured. When used to determine viscosities, flow of a sample fluid can be generated by applying positive-gauge pressures, by applying vacuum or negative-gauge pressures, by electrokinetic microfluidic techniques, or the like. When a fluid sample flows through a flow-resisting channel, the pressure loss can be determined by providing an intersection downstream of the flow-resisting channel segment. Specifically, by coupling a detectable fluid source to the intersection via a second flow resisting channel segment, and (for example) drawing a vacuum downstream of the intersection, the sample and detectable fluid is drawn and mixed in a ratio which depends in part on the viscosities of the sample and detectable fluid. Determination of the viscosity of a particular sample fluid can be simplified by flowing a reference fluid through the flow-resisting channel so as to calibrate the signal provided by a downstream sensor.

The present invention optionally makes use of a multi-reservoir pressure controller coupled to a plurality of independently variable pressure modulators to effect movement of fluids within microfluidic networks, e.g., while providing monitoring of flow inducing pressures. By selectively controlling and changing the pressure applied to the reservoirs of a microfluidic device, hydrodynamic flow at very low flow rates can be accurately controlled within intersecting microfluidic channels. Such pressure-induced flows can help to decrease (or entirely avoid) any detrimental effects of the electrical fields associated with electrokinetic transportation methods, such as sample bias, cell perforation, electroporation, and the like. Additionally, such pressure-induced microfluidic flows can, through proper chip design, reduce flow variabilities as compared to electrokinetic techniques through the use of pressure differentials (and/or channel resistances) that are significantly greater than flow variations induced by secondary effects, such as inflow/outflow capillary force differentials within the reservoirs). Advantageously, the pressure-induced flows of the present invention can also be combined with electrokinetic and/or other fluid transportation mechanisms, thereby providing composite pressure/electrokinetic microfluidic systems.

The techniques of the present invention will often make use of data regarding the network of channels within a microfluidic device. This network data can be calculated using a model of the microfluidic network, measured by testing a microfluidic device, sensed using a sensor, and/or the like. The network data will often be in the form of hydrodynamic resistances along microfluidic channel segments connecting nodes, with the nodes often being intersections between channels, ports or reservoirs, connections between channel segments having differing cross-sectional dimensions and/or flow characteristics, and the like. As used herein, the term "reservoir" encompasses ports for interfacing with a microfluidic network within a microfluidic body, including ports which do not have cross-sections that are much larger than the microfluidic channel to enhance fluid capacity.

By selectively controlling the pressure at most or all of the reservoirs of a microfluidic system, very small flow rates can be induced through selected channel segments. Such small pressure-induced flows can be accurately controlled at flow rates which might be difficult and/or impossible to control using alternative fluid transportation mechanisms. Advantageously, the present invention can provide flow rates of less than 0.1 nanoliters per second, the flow rates often being less than 1 nanoliters per second, and the pressure induced flow rates typically being less than 10 nanoliters per second within the microfluidic channel.

To accurately apply the pressures within the microfluidic network, the invention can optionally make use of a pressure transmission system having relatively large lumens coupling the pressure modulators to the reservoirs of the microfluidic device, with the pressure transmission lumens ideally containing a compressible gas. Pressure is often transmitted through this relatively low resistance pressure transmission system to fluids disposed within the reservoirs of the microfluidic system via a gas/fluid interface within the reservoir. The resistance of the microfluidic channels to the fluid flows therein is typically much greater than the resistance of the pressure transmission lumens to the associated flow of compressible gas. Generally, the channel resistance is at least 10 times the transmission system resistance, preferably being at least 100 times, and ideally being at least 1000 times the transmission system resistance of the compressible gas used to induce the channel flows. In other words, a response time constant of the pressure transmission system will generally be lower than the time constant of the channel network, preferably being much lower, and ideally being at least one, two, or three orders of magnitude lower. The head space of a fluid (for example, in the pressure modulator pump and/or in the port or reservoir) times the resistance of the fluid flow (for example, in the channels or lumens) generally define the response time constant.

It is often advantageous to enhance the resistance of the microfluidic channels to provide the desired relative resistance factors. The channels optionally have reduced cross-sectional dimensions, pressure drop members (such as a small cross-section pressure orifice, a flow restricting substance or coating, or the like), and/or lengths of some, most, or even all of the microfluidic channel segments are optionally increased by including serpentine segment paths. As the resistance of the pressure transmission system can be several orders of magnitude less than the resistance of the channels, pressure differentials can be accurately transmitted from the pressure modulators to the reservoirs of the microfluidic device. Additionally, reduced transmission system resistances can help to enhance the response of the pressure system, providing a faster response time constant.

Referring now to FIG. 1, a microfluidic system 10 includes a microfluidic device 12 coupled to a bank of pressure modulators 14 by a pressure transmission system 16. Pressure modulator bank 14 includes a plurality of pressure modulators 14a, 14b, . . . Modulator bank 14 will generally include at least three independently, selectively variable pressure modulators, typically having at least four modulators, and ideally having eight or more modulators. Each modulator is in fluid communication with a reservoir 18 of microfluidic device 12 via an associated tube 20, the tube having a pressure transmission lumen with a compressible gas therein.

Modulator bank 14 generally provides independently selectable pressures to the lumens of tubing 20 under the direction of a controller(s) 22. Feedback can be provided to controller 22 from pressure sensors 24, as will be described hereinbelow. Processor 22 will often comprise a machine-readable code embodied by tangible media 26, with the machine-readable code comprising program instructions and/or data for effecting the methods of the present invention. Processor 22 can comprise a personal computer having at least an Intel Pentium® or Pentium II® processor having a speed of at least 200 MHz, 300 MHz, or more. Tangible media 26 can comprise one or more floppy disks, compact disks, or "CDs," magnetic recording tape, a read-only memory, a random access memory, or the like. In some embodiments, the programming instructions can be input into controller 22 via a disk drive or other input/output system such as an internet, intranet, modem reservoir, or the like. Suitable programs can be written in a variety of programming languages, including the LabView™ language, as available from National Instruments of Austin, Tex. Controller 22 transmits drive signals to modulator bank 14, ideally via an RS232/RS485 serial connection.

In addition to tubing 20, pressure transmission system 16 includes a manifold 28. Manifold 28 releasably seals the lumen of each tube 20 with an associated reservoir 18 of microfluidic device 12. Tubing 20 can comprise a relatively high-strength polymer such as polyetheretherketone (PEEK), or a polytetrafluoroethylene (such as a Teflon™ material), or the like. The tubing typically has an inner diameter in a range from about 0.01" to about 0.05", with a length from about 1 m to about 3 m. A "T" connector couples the pressure output from each pressure modulator to an associated pressure sensor 24.

Each modulator 14a, 14b . . . generally comprises a pump or other pressure source which pressurizes the compressible gas within the lumen of associated tubing 20. The modulators preferably comprise positive displacement pumps, with the exemplary modulators comprising a piston which is selectively positioned within a surrounding cylinder by an actuator. Preferably, the actuators are adapted to allow accurate positioning of the piston in response to drive signals from controller 22, the exemplary actuators comprising stepper motors. The exemplary piston/cylinder arrangement is similar to a syringe. Exemplary modulator banks can be provided by (or modified from components available through) a variety of commercial sources, including Kloehn of Las Vegas, Nev., Cavaro of Sunnyvale, Calif., and the like.

Figure 2:
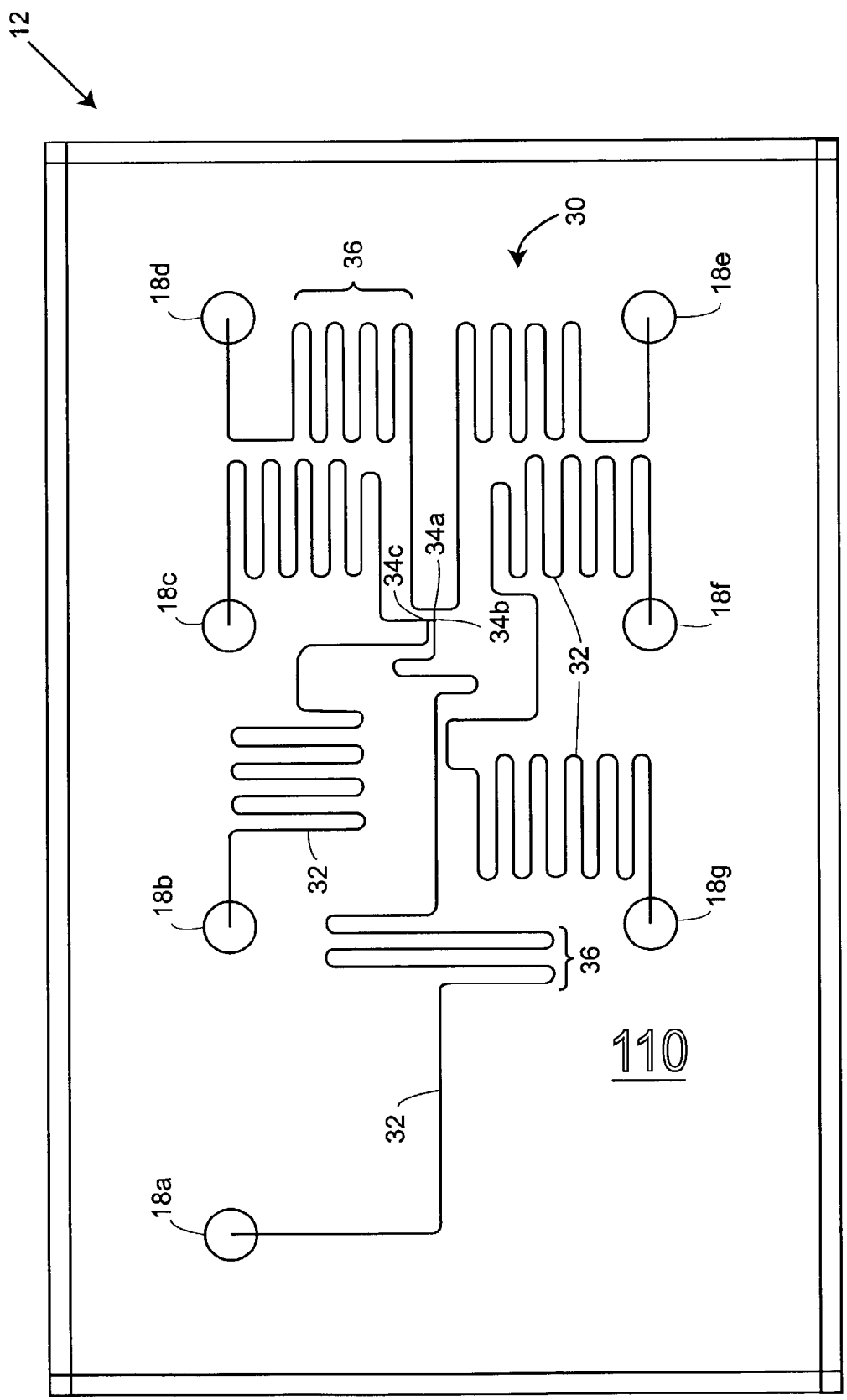
FIG. 2 is a plan view of a representative microfluidic device having microfluidic channels with enhanced fluid flow resistance for use in the microfluidic system of FIG. 1.

Microfluidic device 12 is seen more clearly in FIG. 2. Microfluidic device 12 includes an array of reservoirs 18a, 18b, . . . coupled together by microscale channels defining a microfluidic network 30. As used herein, the term "microscale" or "microfabricated" generally refers to structural elements or features of a device which have at least one fabricated dimension in the range of from about 0.1 µm to about 500 µm. Thus, a device referred to as being microfabricated or microscale will include at least one structural element or feature having such a dimension. When used to describe a fluidic element, such as a passage, chamber or conduit, the terms "microscale", "microfabricated" or "microfluidic" generally refer to one or more fluid passages, chambers or conduits which have at least one internal cross-sectional dimension, e.g., depth, width, length, diameter, etc., that is less than 500 µm, and typically between about 0.1 µm and about 500 µm. In the devices of the present invention, the microscale channels or chambers preferably have at least one cross-sectional dimension between about 0.1 µm and 200 µm, more preferably between about 0.1 µm and 100 µm, and often between about 0.1 µm and 50 µm.

The microfluidic devices or systems of the present invention typically include at least one microscale channel, usually at least two intersecting microscale channel segments, and often, three or more intersecting channel segments disposed within a single body structure. Channel intersections can exist in a number of formats, including cross intersections, "T" intersections, or any number of other structures whereby two channels are in fluid communication.

The body structures of the devices which integrate various microfluidic channels, chambers or other elements can be fabricated from a number of individual parts, which, when connected, form the integrated microfluidic devices described herein. For example, the body structure can be fabricated from a number of separate capillary elements, microscale chambers, and the like, all of which are connected together to define an integrated body structure. Alternatively and in preferred aspects, the integrated body structure is fabricated from two or more substrate layers which are mated together to define a body structure having the channel and chamber networks of the devices within. In particular, a desired channel network is laid out upon a typically planar surface of at least one of the two substrate layers as a series of grooves or indentations in that surface. A second substrate layer is overlaid and bonded or fused to the first substrate layer, covering and sealing the grooves, to define the channels within the interior of the device. In order to provide fluid and/or control access to the channels of the device, a series of reservoirs or reservoirs is typically provided in at least one of the substrate layers, which reservoirs or reservoirs are in fluid communication with the various channels of the device.

A variety of different substrate materials can be used to fabricate the devices of the invention, including silica-based substrates, i.e., glass, quartz, fused silica, silicon and the like, polymeric substrates, i.e., acrylics (e.g., polymethylmethacrylate) polycarbonate, polypropylene, polystyrene, and the like. Examples of preferred polymeric substrates are described in commonly owned published international patent application no. WO 98/46438 which is incorporated herein by reference for all purposes. Silica-based substrates are generally amenable to microfabrication techniques that are well-known in the art including, e.g., photolithographic techniques, wet chemical etching, reactive ion etching (RIE) and the like. Fabrication of polymeric substrates is generally carried out using known polymer fabrication methods, e.g., injection molding, embossing, or the like. In particular, master molds or stamps are optionally created from solid substrates, such as glass, silicon, nickel electro forms, and the like, using well-known micro fabrication techniques. These techniques include photolithography followed by wet chemical etching, LIGA methods, laser ablation, thin film deposition technologies, chemical vapor deposition, and the like. These masters are then used to injection mold, cast or emboss the channel structures in the planar surface of the first substrate surface. In particularly preferred aspects, the channel or chamber structures are embossed in the planar surface of the first substrate. Methods of fabricating and bonding polymeric substrates are described in commonly owned U.S. patent application Ser. No. 09/073,710, filed May 6, 1998, and incorporated herein by reference in its entirety for all purposes.

Further preferred aspects of the microfluidic devices of the present invention are more fully described in co-pending U.S. patent application Ser. No. 09/238,467, as filed on Jan. 28, 1999 (commonly assigned with the present application), the full disclosure of which is incorporated herein by reference. These preferred aspects include, for example, a reaction zone disposed within the overall body structure of the device, a reagent or other component of an "biochemical system" (generally referring to a chemical interaction that involves molecules of the type generally found within living organisms), sensing systems for detecting and/or quantifying the results of a particular reaction (often by sensing an optical or other detectable signal of the reaction), and the like.

Referring once again to FIG. 2, reservoirs 18 will often be defined by openings in an overlaying substrate layer. Reservoirs 18 are coupled together by channels 32 of microfluidic network 30, with the channels generally being defined by indentations in an underlying layer of the substrate, as was also described above.

Microfluidic channels 32 are in fluid communication with each other at channel intersections 34a, 34b, . . . (generally referred to as intersections 34). To simplify analysis of microfluidic network 30, channels 32 can be analyzed as channel segments extending between nodes defined at reservoirs 18 and/or channel intersections 34.

To provide enhanced control over movement of fluids within microfluidic network 30 by reducing the effects of secondary hydrostatic forces (such as capillary forces within reservoirs 18), the resistance of channels 32 to flow through the microfluidic network can be enhanced. These enhanced channel resistances can be provided by having a channel length greater than the normal separation between the nodes defining the channel segment, such as by having serpentine areas 36 along the channel segments. Alternatively, a cross-sectional dimension of the channel can be decreased along at least a portion of the channel, or flow can be blocked by a flow restrictor such as a local orifice, a coating or material disposed in the channel, or the like. In general, to take advantage of the full range of flow control provided by the pressure modulators, microfluidic device 12 should be optimized for hydrodynamic flow. Flow control is generally enhanced by providing sufficient flow resistance between each reservoir 18 and the adjacent nodes so as to allow a sufficient variation in flow rate to be achieved within the various channel segments given the dynamic operating pressure range of the pressure modulators.

Pressure manifold 28 can be seen more clearly in FIGS. 3A and 3B. Manifold 28 has at least one device engaging surface 40 for engaging microfluidic device 12, with the engagement surface having an array of pressure lumens 42 corresponding to reservoirs 18 of the device. Each of pressure lumens 42 is in fluid communication with a fitting 44 for coupling each reservoir with an associated pressure modulator via an associated tube. Sealing body 46 helps maintain a seal between the associated pressure modulator and reservoir, and manifold 28 is releasably secured to device 12 by a securing mechanism 48, which here includes openings for threaded fasteners, or the like.

Manifold 28 can comprise a polymer, a metal such as 6061-T6 aluminum, or a wide variety of alternative materials. Lumens 42 can have a dimension in a range from about 2 mm to about 3 mm. Fittings 44 optionally comprise standard ¼-28 fittings. Sealing body 46 will often comprise an elastomer such as a natural or synthetic rubber.

The pressure transmission system (including manifold 28) will preferably maintain a seal when transmitting pressures greater than atmospheric pressure (positive gauge pressures) and less than atmospheric pressure (negative gauge pressures or vacuum). The pressure transmission system and modulator bank 14 will generally be capable of applying pressure differentials which are significantly higher than hydrostatic and capillary pressures exerted by, for example, a buffer or other fluid in reservoirs 18, so as to avoid variability or noise in the pressure differential and resulting flow rates. As capillary pressures within reservoirs 18 are typically less than 1/10 of a psi, often being less than 1/100th of a psi, the system will preferably be capable of varying pressure at reservoirs 18 throughout a range of at least ½ psi, more often having a pressure range of at least 1 psi, and most often having a pressure range of at least +/−1 psig (so as to provide a 2 psi pressure differential). Many systems are capable of applying at least about a 5 psi pressure differential, optionally having pressure transmission capabilities so as to apply pressure anywhere throughout a range of at least about +/−5 psig.

A control system for selecting the pressures applied to reservoirs 18 is schematically illustrated in FIG. 4. Controller 22 generally includes circuitry and/or programming which allows the controller to determine reservoir pressures which will provide a desired flow within a channel of microfluidic network 30 (here schematically illustrated as microfluidic network controller 52) and also includes circuitry and/or programming to direct the modulators of modulator bank 14 to provide the desired individual reservoir pressures (here schematically illustrated as a plurality of pressure controllers 54.) It should be understood that network controller 52 and pressure controller 54 can be integrated within a single hardware and/or software system, for example, running on a single processor board, or that a wide variety of distributing process techniques might be employed. Similarly, while pressure controllers 54 are schematically illustrated here as separate pressure controllers for each modulator, a single pressure controller can be used with data sampling and/or multiplexing techniques.

In general, pressure controller 54 transmits drive signals to an actuator 56, and the actuator moves a piston of displacement pump or syringe 58 in response to the drive signals. Movement of the piston within pump 58 changes a pressure in pressure transmission system 20, and the change in pressure is sensed by pressure sensor 24. Pressure sensor 24 provides a feedback signal to the pressure controller 54, and the pressure controller will optionally make use of the feedback signal so as to tailor the drive signals and accurately position the piston.

To enhance the time response of the pressure control system, pressure controller 54 can include pressure calibration data 60. The calibration data will generally indicate a correlation between drive signals transmitted to actuator 56 and the pressure provided from the pressure modulator. Pressure calibration data 60 will preferably be determined by initially calibrating the pressure change system, ideally before initiation of testing using the microfluidic network.

Generation of calibration data 60 can be effected by transmitting a calibration drive signal to actuator 56 and sensing the pressure response using pressure sensor 24. The change of pressure from this calibration test can be stored in the program as calibration data 60. The calibration signal will typically cause a known displacement of the piston within pump 58. Using this known displacement and the measured change in pressure, the overall pressure system response can be calculated for future drive signals using the ideal gas law, $PV=nRT$ (in which P is pressure, V is the total compressible air volume, n is the number of moles of gas in the volume, R is the gas constant, and T is the temperature). Calibration can be preformed for each modulator/pressure transmission systems/reservoir (so as to accommodate varying reagent quantities within the reservoirs, and the like), or can be preformed on a single reservoir pressurization system as an estimate for calibration for all of the modulators of the system.

Once calibration data 60 has been generated, pressure controller 54 can generate drive signals for actuator 56 quite quickly in response to a desired pressure signal transmitted from network controller 52. It should be noted that these estimate will preferably accommodate the changing overall volume of the compressible gas within the system, so that the calculated change in pressure for a given displacement of the piston within pump 58 at low pressures can be different than the same displacement of the piston at high pressures (i.e., the displacement/pressure correlation plot is not linear, but curves.).

In the exemplary embodiment, actuator 56 comprises a stepper motor coupled to a linear output mechanism. Pump 58 comprises a syringe having a length of about 100 mm, and a diameter of about 20 mm. Overall response time for the system can depend on a variety of parameters, including dead volume, syringe size, and the like. Preferably, the response time will be less than about 1 sec/psi of pressure change, ideally being less than about 500 msecs/psi for a pressure change from zero to 1 psi.

Network controller 52 generally calculates the desired pressure from each pressure modulator in response to a desired flow in one or more of the channels of microfluidic network 30. Given a desired channel flow, network controller 52 derives these pressures using network data 62, with the network data typically being supplied by either a mathematical model of the microfluidic network 64 and/or a tester 66. Network data 62 will generally indicate a correlation between pressure differentials applied to reservoirs 18 and flows within the microfluidic channels.

Network model 64 preferably comprises programming to help translate desired hydrodynamic flow rates into pressures to be applied at reservoirs 18. An exemplary network model 64 generates a hydrodynamic multi-level resistance network correlating to each microfluidic network 30, as can be understood with reference to FIGS. 5A–5C.

Figure 5A:
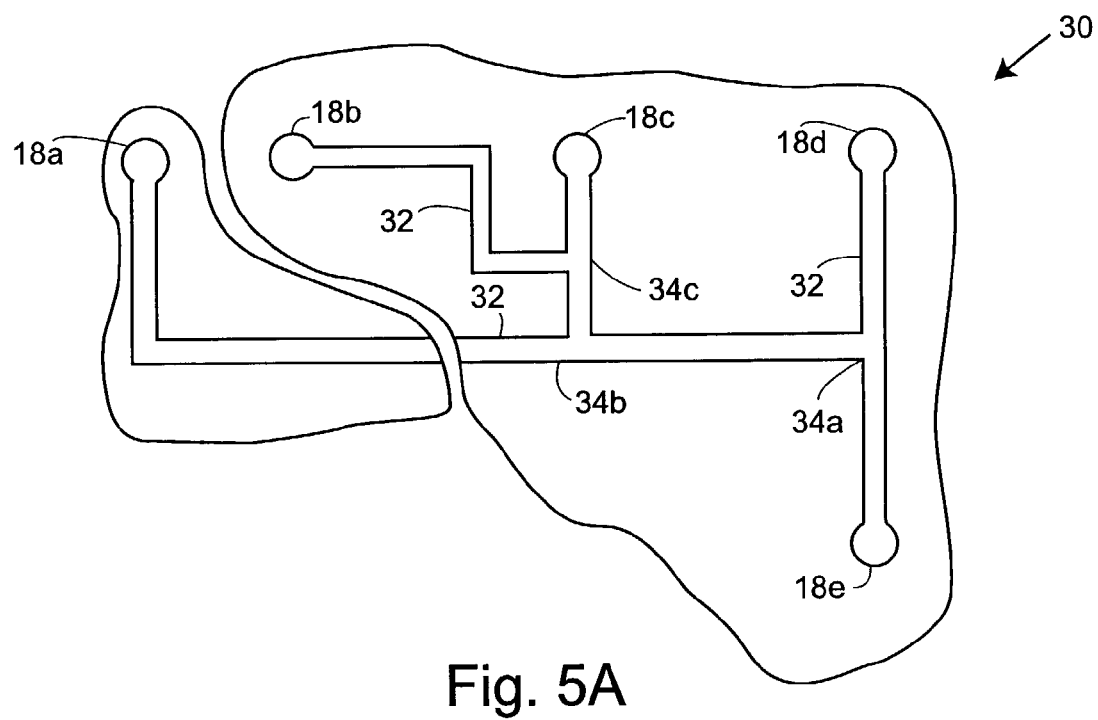
FIGS. 5A–C schematically illustrate a method and computer program for determining pressures to provide a desired flow within a channel of the microfluidic network in the microfluidic device of FIG. 2.

Referring now to FIGS. 5A and 2, nodes can be defined at each well 18 and at each intersection 34. Hydrodynamic resistances of channel segments coupling the nodes can be calculated from the chip design. More specifically, calculation of hydrodynamic resistances can be preformed using hydrostatic pressure loss calculations based on the cross sectional dimensions of channels 32, the length of channel segments connecting the nodes, the channel surface properties, the fluid properties of the fluids included in the flows, and the like.

Figure 5B:
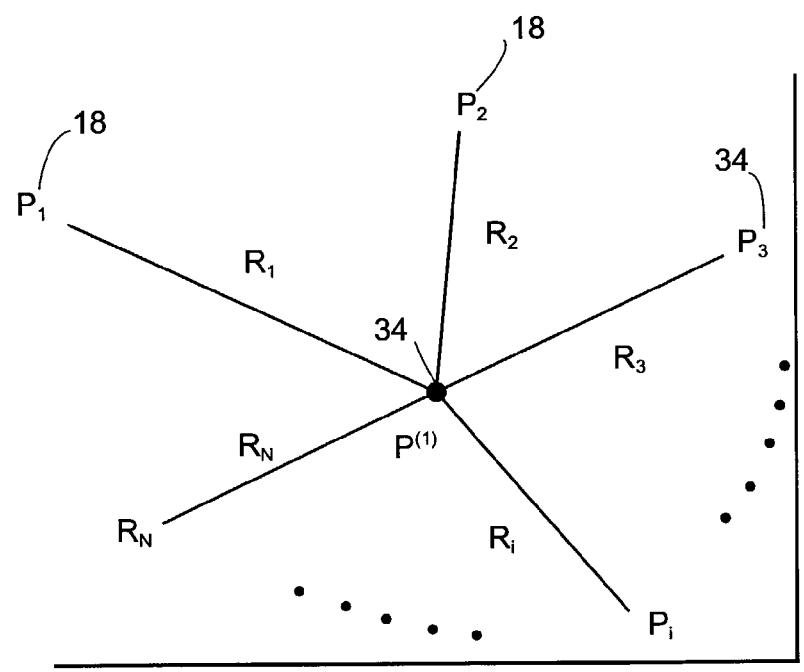
Figure 5C:
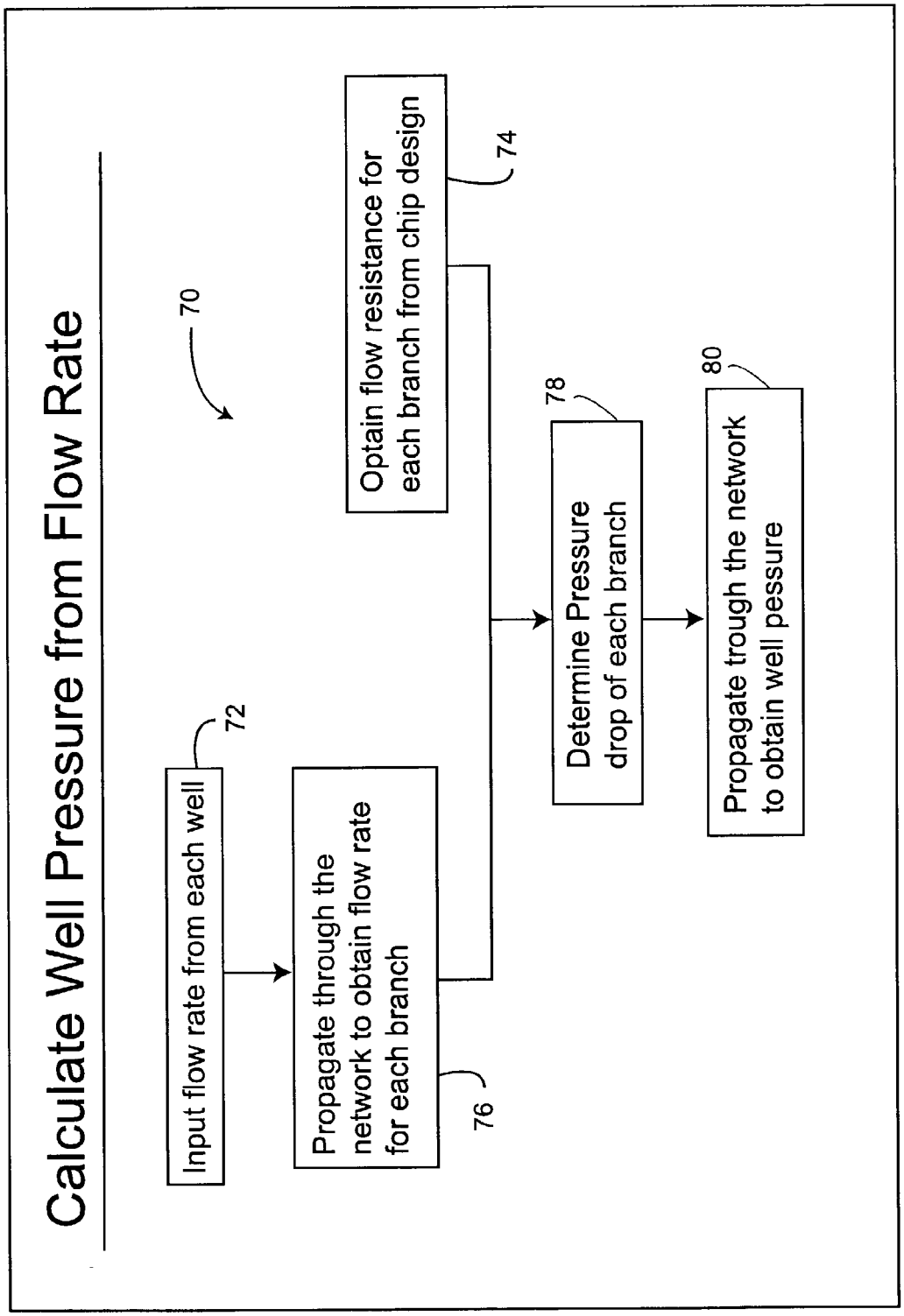

Analysis of the multi-level flow resistance network can be performed using techniques often used for analysis of current in electrical circuits, as can be understood with reference to FIGS. 5B–5C. Hydrodynamic resistances of the channel segments connecting reservoirs 18 to adjacent nodes can be analyzed as the lowest level of a multi-level network. The channel segments adjoining these lowest level segments form the second level of hydrodynamic resistances of the network. This level-by-level analysis continues until all channels of microfluidic network 30 are included in the network model. The relative flow rate of any channel in the microfluidic network can then be obtained once the flow rates from each of the reservoirs 18 in the lowest level have been calculated.

As described above, flow resistances are optionally calculated based upon hydrodynamic chip design alone. It is also possible to measure these resistances using, for example, electrical sensors, pressure drop sensors, or the like. In other words, resistances to hydrodynamic flow of the channels and channel segments can be measured by, for example, measuring electrical resistance between reservoirs 18 while a conductive fluid is disposed within the network. Regardless, once the channel resistances are known, the pressure drop in each channel segment in the network can be obtained by simply multiplying the flow rate of that channel with its associated channel resistance. The pressure of each reservoir 18 can then be calculated by summing up all the pressure drops along the network 30 starting at the top level of the network.

Referring now to the exemplary program for calculating pressures illustrated in FIGS. 5B and 5C, hydrodynamic flow rate Q is related to flow resistance $R_e$ and pressure differential $\Delta P$ by the equation:

$$\Delta P = Q \cdot R_e$$

This relationship is quite similar to that used in electrokinetic calculations, in which current I and electrical resistance R are related to voltage V by the equation:

$$V = I \cdot R$$

This simplifies the application of circuit analysis techniques to the hydrodynamic analysis.

Determination of reservoir pressures so as to provide a desired flow rate are preferably performed using pressure calculation program 70, as illustrated in FIG. 5C. Desired flow rates are input in step 72 from each reservoir 18. These flow rates can be input by the user, by an automated test matrix generation program, or the like. Flow resistances are obtained 74 as described above, and the input flow rate propagates through the network to obtain flow rates for each branch 76. The pressure drop of each branch is then determined using the network resistance circuit 78. These pressure branches are then allowed to propagate through the network to obtain reservoir pressures 80 so as to effect the desired flow.

Figure 6:
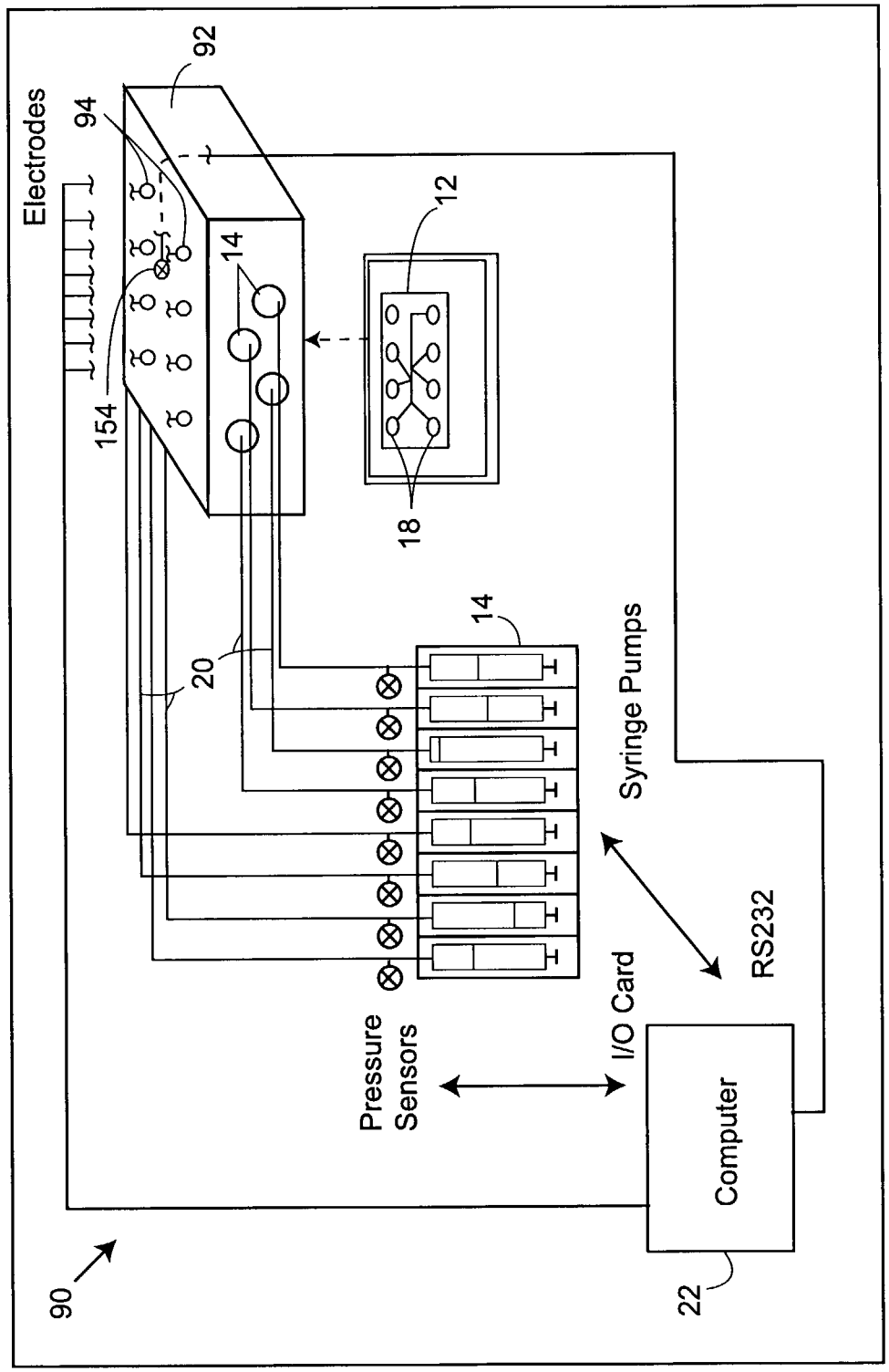
FIG. 6 schematically illustrates a microfluidic system having both a multi-reservoir pressure modulation system and an electrokinetic fluid transportation and control system according to the principles of the present invention.

Referring to FIG. 6, an alternative embodiment of a microfluidic system makes use of both electrokinetic transport and hydrodynamic transport mechanisms to move fluids (induce flow) within microfluidic channels of the system. Electrokinetic transfer of fluids has significant advantages when electro osmosis and/or electrophoresis are desired. Electrokinetic fluid transport is also both fast and convenient, and modifications of the channel surfaces are possible to avoid and/or alleviate electrokinetic transport disadvantages. The plug profiles of fluid plugs moved within a electrokinetic transport system can also be well-controlled and defined. As described in detail hereinbelow, controller 22 can be coupled to a sensor 154 for determining a viscosity of a sample fluid within the microfluidic network. Alternatively, a separate processor can be provided for calculating viscosities.

Electrokinetic/hydrodynamic system 90 also provides the advantages of hydrodynamic transport described above. This hydrodynamic transport is quite reliable, and is independent of charges and electrical surface properties of the channels. Hydrodynamic transport is particularly well-suited for biocompounds which are sensitive to electrical fields.

Electrokinetic/hydrodynamic microfluidic system 90 includes many of the pressurization, microfluidic network and control components described above. In this embodiment, manifold 92 includes fittings 44 opening laterally from the manifold to provide sealed fluid communication from each pressure transmission tube 20 to an associated reservoir 18 of the microfluidic device 12. Additionally, electrodes 94 are coupled to each reservoir 18 via manifold 92. In the exemplary embodiment, the electrodes comprise platinum surfaces which extend down from manifold 92 into electrical contact with fluids disposed within reservoirs 18 when the manifold provides a sealing engagement between fittings 44 and the reservoirs. Coupling of the electrodes with the fittings 44 can be provided by using "T" connectors within the manifold for each well, and inserting a platinum electrode across and through the "T". The appropriate (upper, in this example) connector branch of the T-connector can be sealed and the electrode affixed in place with a sealing material such as epoxy.

By coupling electrodes 94 to computer 22, and by including within computer 22 an electrokinetic fluid transport controller capable of inducing electro-osmosis and electrophoresis, the system of FIG. 6 is capable of emulating pumps, valves, dispensers, reactors, separation systems, and other laboratory fluid handling mechanisms, often without having to resort to moving parts on microfluidic device 12. Electrokinetic transportation and control are described in, for example, U.S. Pat. No. 5,965,001, previously incorporated herein by reference.

Figure 7A:
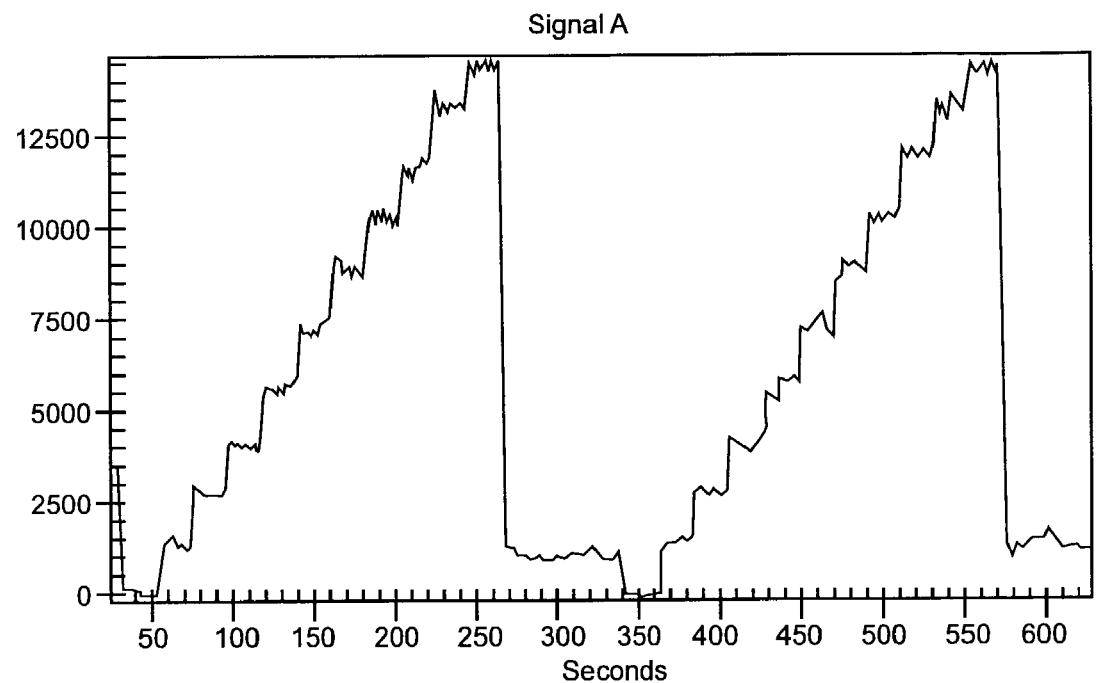
FIGS. 7A and 7B illustrate well-pair dilution in which concentration variations are produced by selectively varying the relative flow rates from two reservoirs connected at an intersection.
Figure 7B:
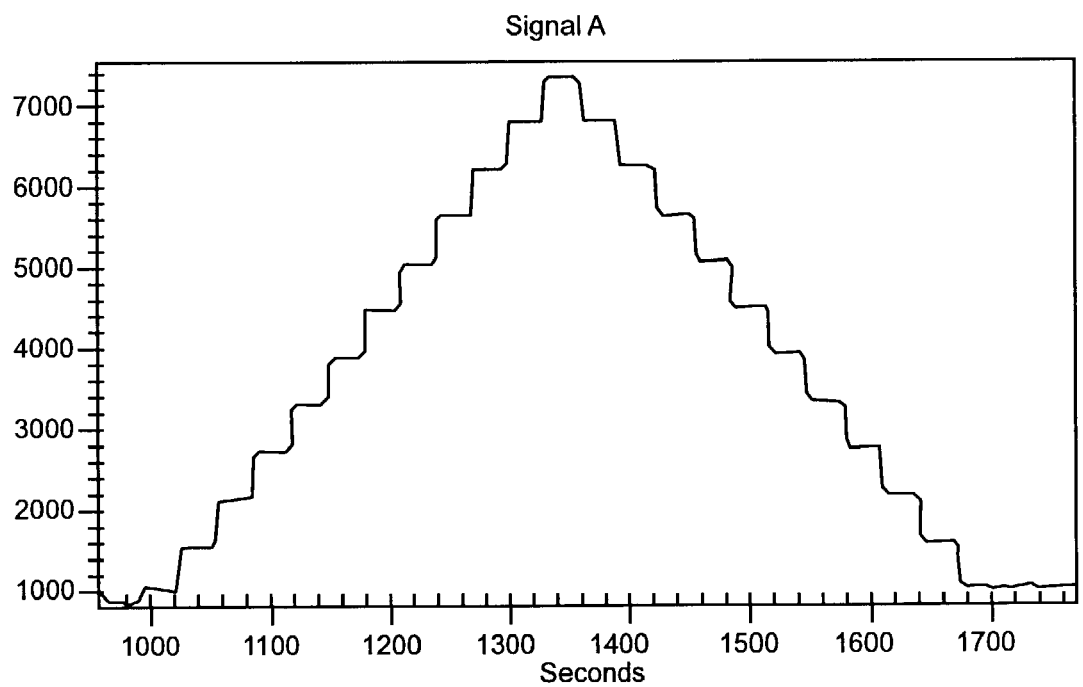

One particular advantageous use of the pressure modulated flow control can be understood with reference to FIGS. 7A and 7B. In many chemical analysis, it is desirable to vary the relative flow rates from two reservoirs connected to a common node so as to vary a concentration of a test solution, reagent, or the like, particularly for defining standard curves of chemical reactions. As illustrated in FIG. 7A, it is possible to vary the flows from two reservoirs electrokinetically, with the relative fluid concentrations being indicated by the changes in fluorescence intensity over time. Unfortunately, control over the relative flow rates (and hence, the concentration) can be less than ideal due to variation in capillary forces within the reservoirs and the like.

An alternative well-pair dilution plot in FIG. 7B can be generated by varying concentrations using multi-pressure control. This plot illustrates the reduced noise and enhanced flow control provided by the pressure control systems of the present invention. As generally described above, hydrodynamic control can be enhanced by increasing resistance of the channel segments. In the exemplary microfluidic device 12 illustrated in FIG. 2, channels 32 coupling wells 18b, 18c, 18d, 18e, 18f, and 18g to the adjacent nodes have a resistance of $1.3 \times 10^{11}$ g/cm$^4$ s. Channel 32 coupling reservoir 18a to the adjacent intersection 34 has a resistance of $4.8 \times 10^{10}$ g/cm$^4$ S. Such a chip is well-suited for use with flows having a pressure drop between reservoirs of about 2 psi, so as to provide a mixing time of about 6 seconds, and a reaction time of about 20 seconds.

Figure 7C:
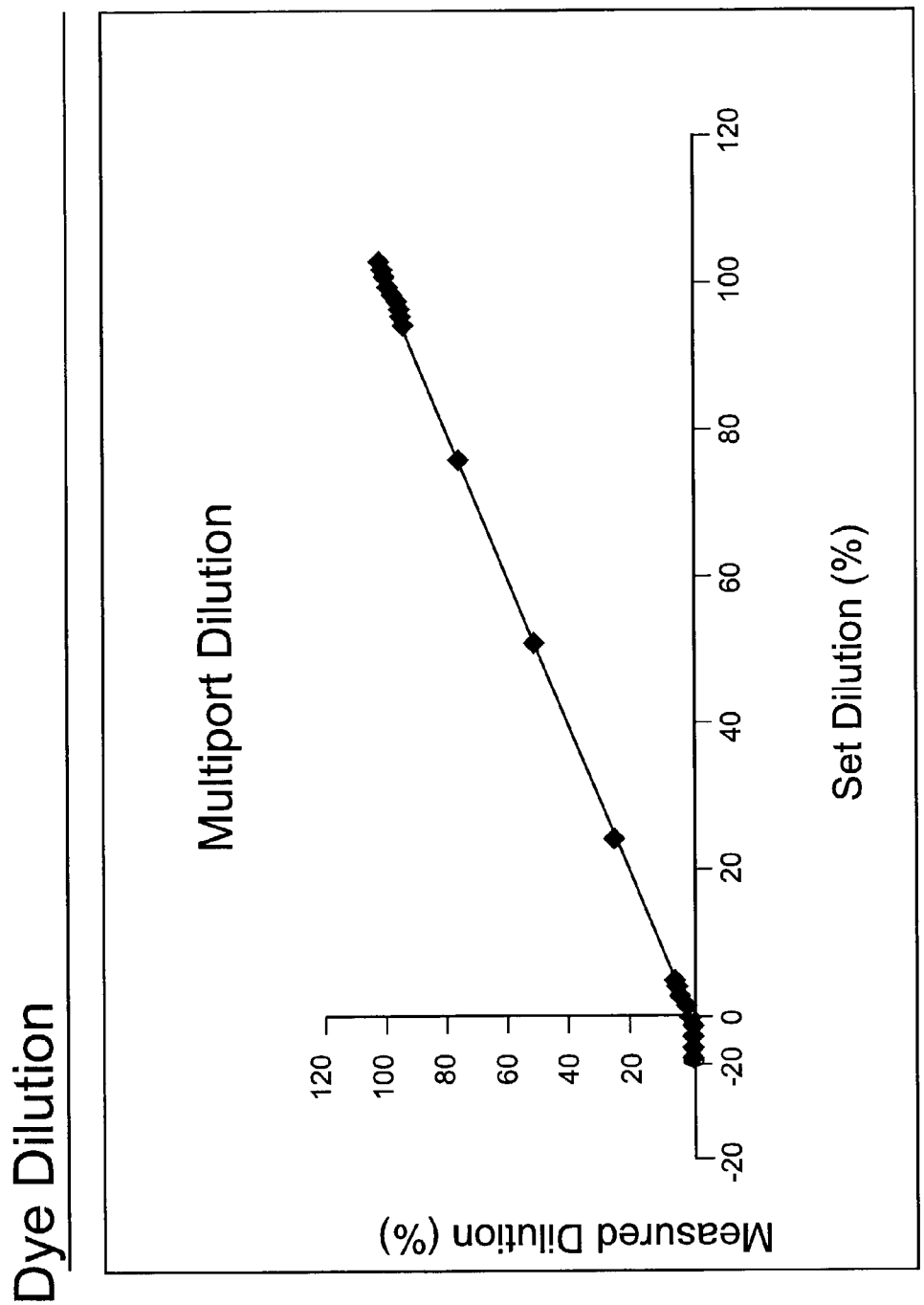
FIGS. 7C–E graphically illustrate measured dilution vs. set or intended dilution for a multi-reservoir pressure controlled well-pair dilution.
Figure 7D:
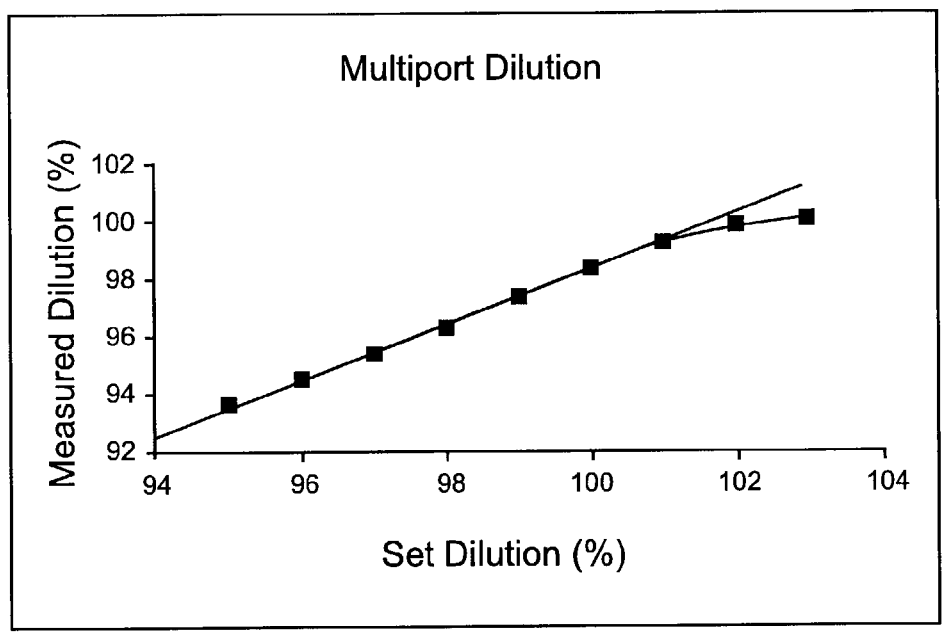
Figure 7E:
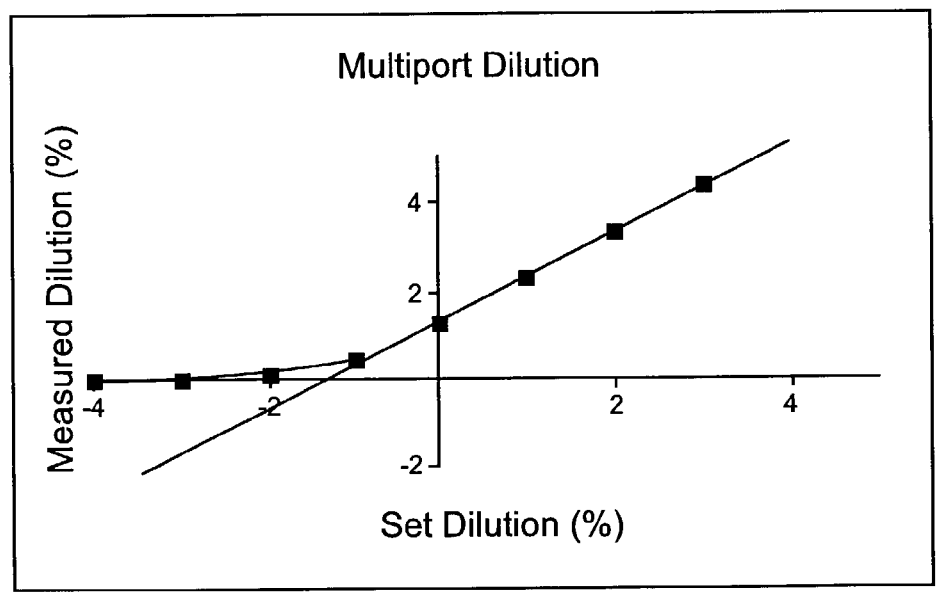

FIG. 7C is a plot of measured dilution vs. set dilution for a dilution well-pair with a hydrodynamic flow system, showing the accuracy and controllability of these dilution methods. FIGS. 7D and 7E are plots of the measured dilution near the upper and lower extremes, respectively, showing that a small amount of mixing at a channel intersection can occur when flow from a channel is at least substantially halted. As can be understood with reference to these figures, some modification of the overall flow from one or more channels at an intersection can be used to effect a desired dilution percentage adjacent a maximum and/or a minimum of the dilution range. For example, relative flow adjustments within 5% of a maximum or minimum desired dilution, and often within 2.5% of a desired maximum and/or minimum can be employed. More specifically, to achieve a near 0% actual dilution from a given channel at an intersection, fluid can flow into the channel at the intersection. Similarly, to achieve 100% measured dilution from the channel, more than 100% of the desired flow can be provided from the supply channel into the intersection.

Figure 8:
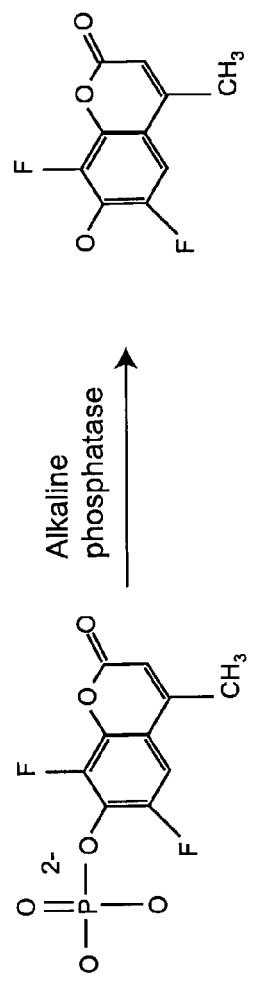
FIGS. 8 and 8A–8D graphically illustrate an enzyme assay using a multi-reservoir pressure controlled microfluidic system, and more specifically.
Figure 8A:
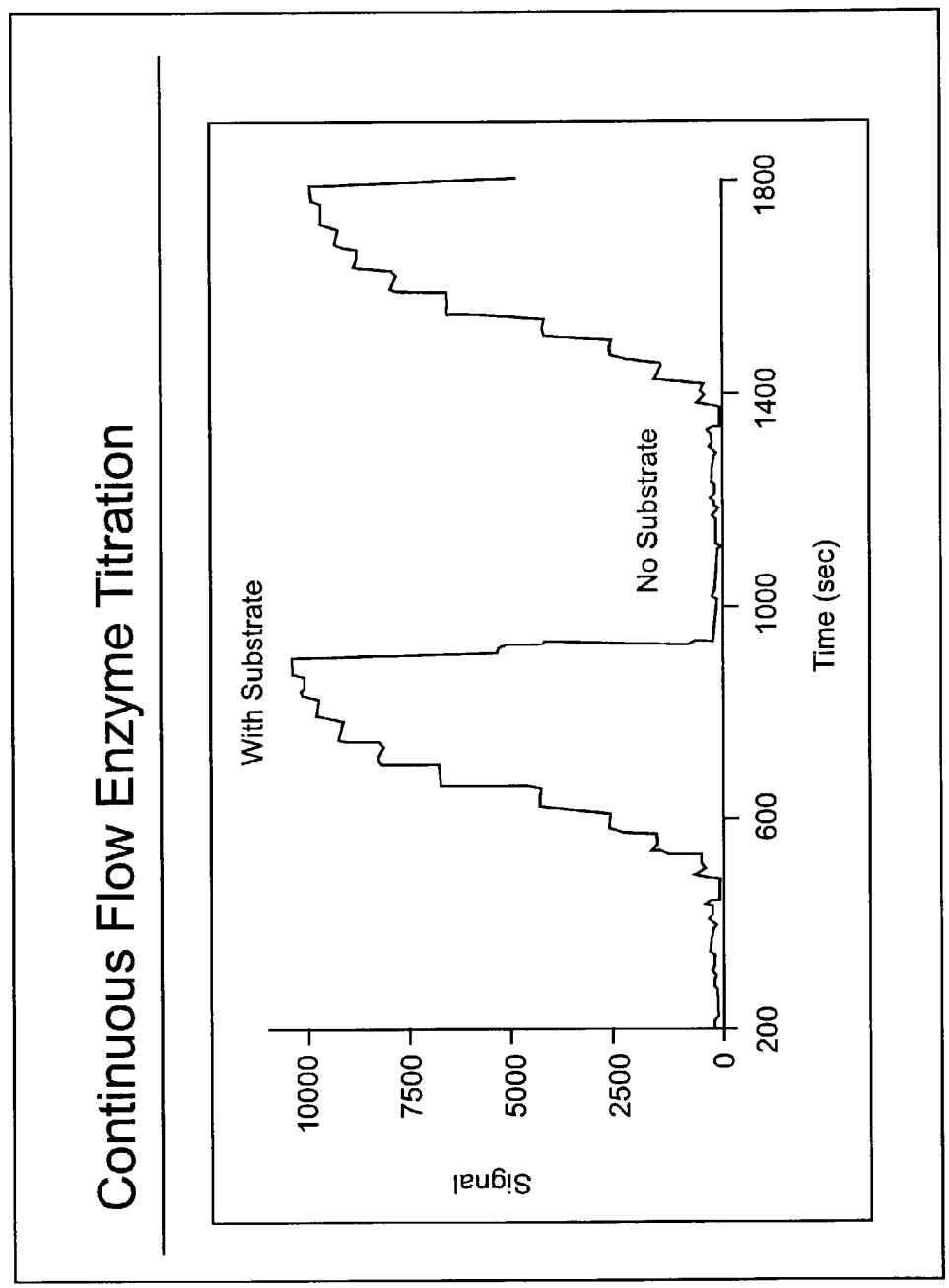
Figure 8B:
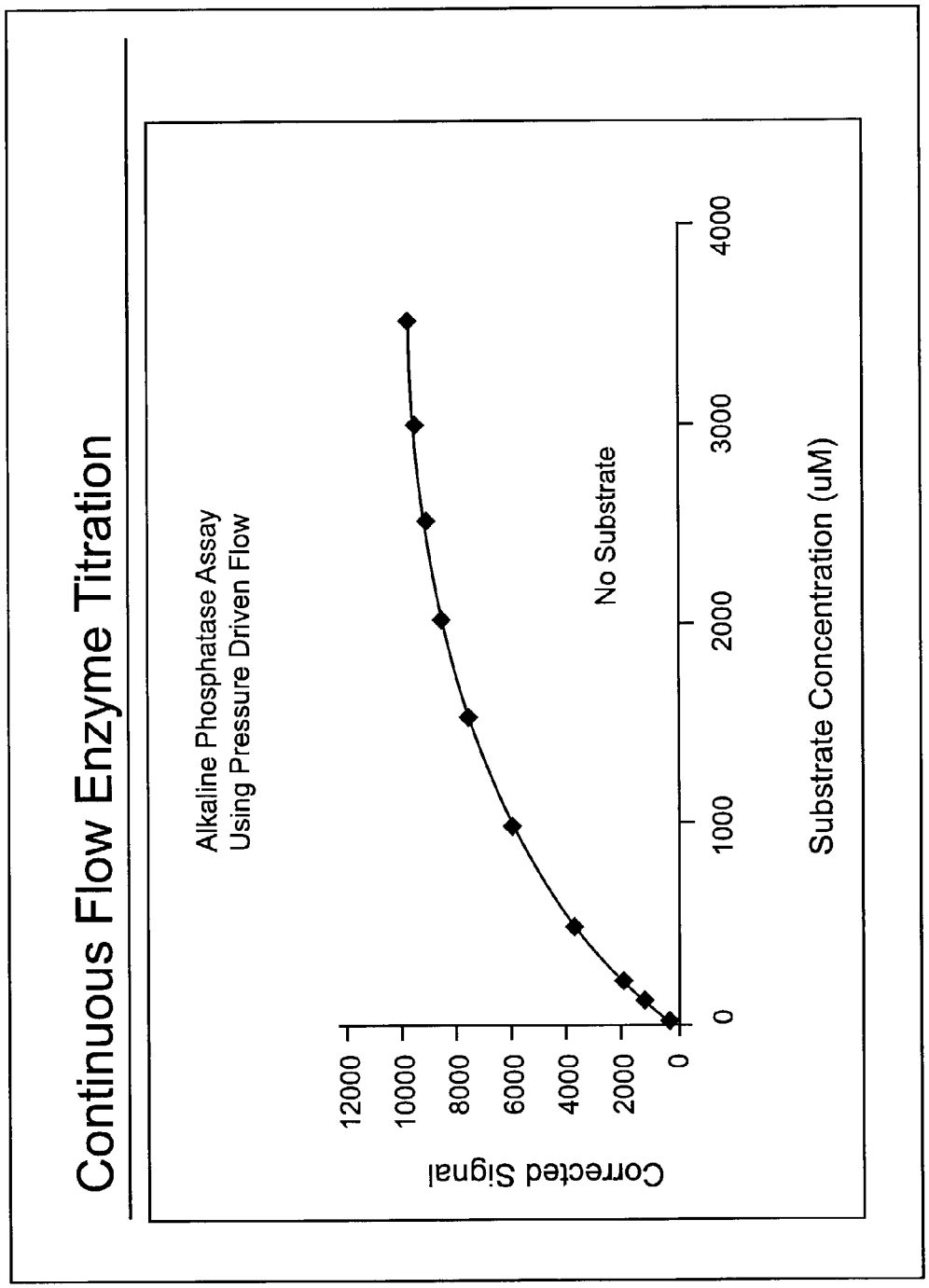
Figure 8C:
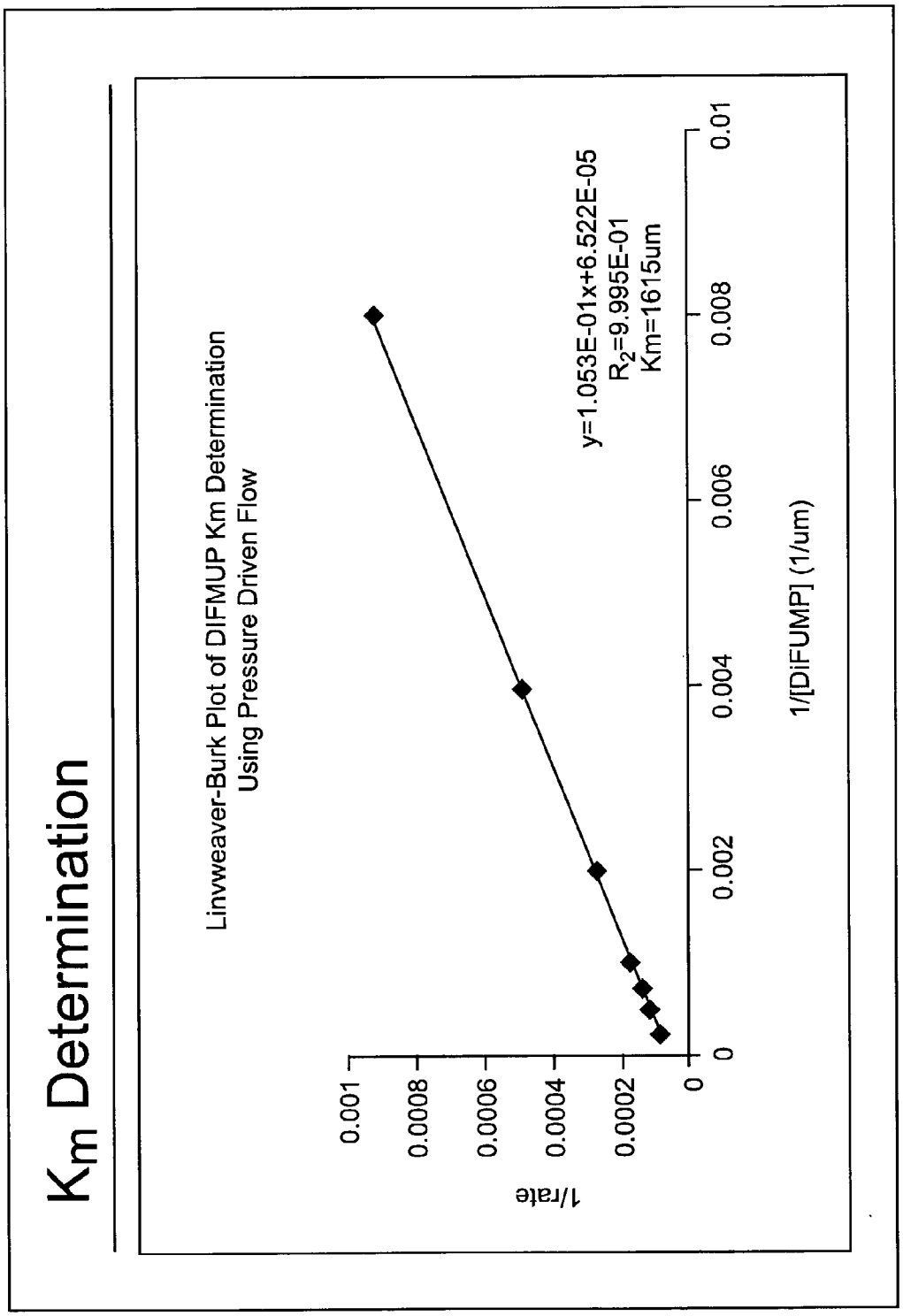
Figure 8D:
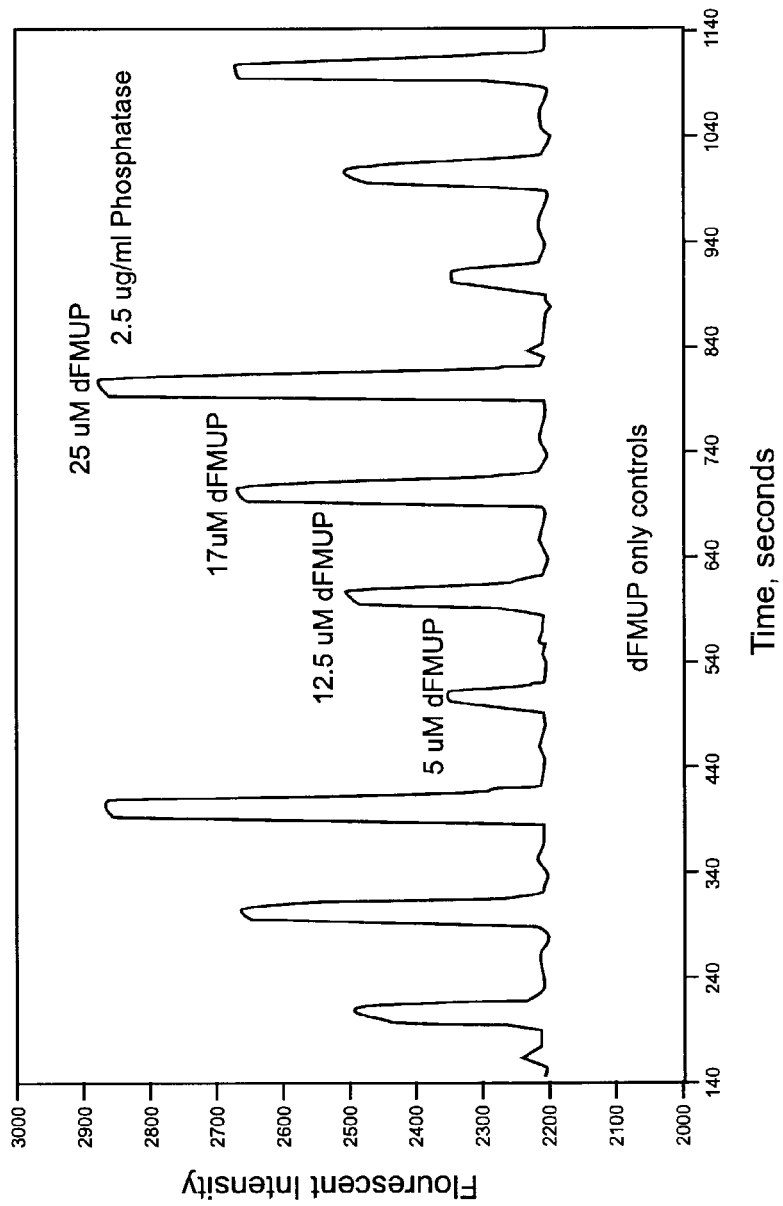

Characterization of an enzyme often involves determination of maximum reaction velocity and a Michaelis constant for each substrate. The enzymatic reaction of Alkaline Phosphatase on dFMUP (as illustrated in FIG. 8) was studied on a microfluidic device 12 optimized for pressure driven flow. FIG. 8A is a titration curve for different concentrations with and without substrate. A plot of background corrected signal vs. substrate concentration is shown in FIG. 8B, while a Lineweaver-Burk plot for the Michaelis constant (Km) is provided in FIG. 8C. Results of a substrate titration assay for the reaction are shown in FIG. 8D.

Figure 9A:
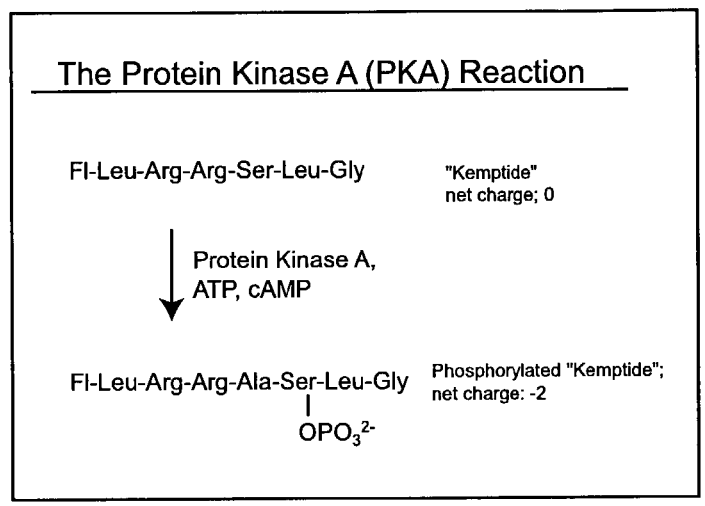
FIGS. 9A–C illustrate a microfluidic Protein Kinase A (PKA) reaction assay with variations in concentration achieved using hydrodynamic pressure modulation.
Figure 9B:
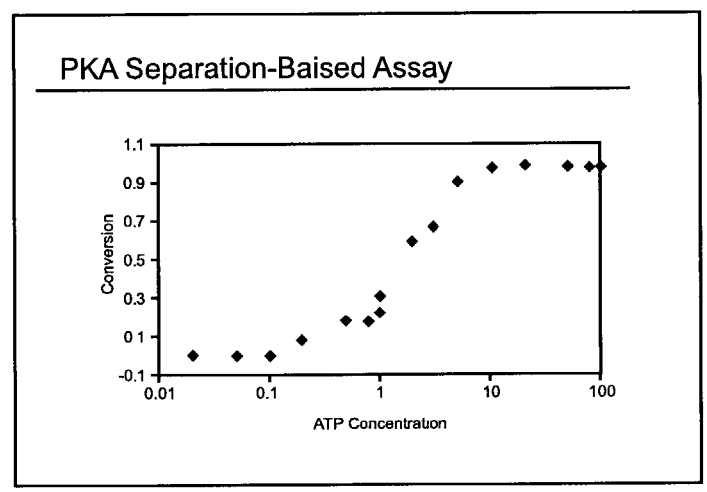
Figure 9C:
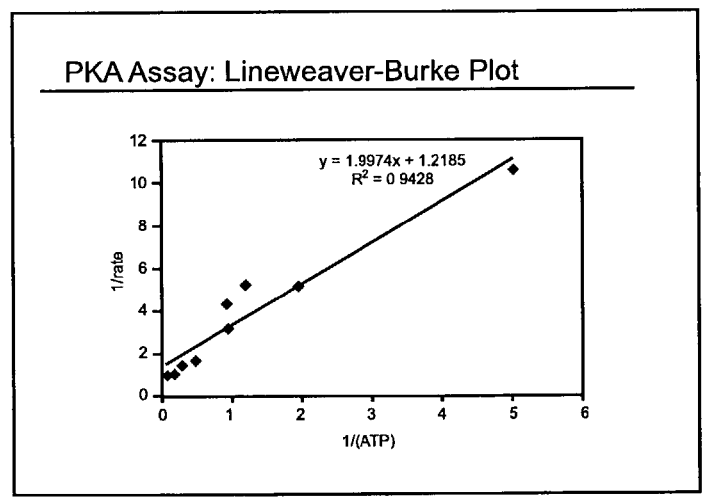
Figure 10A:
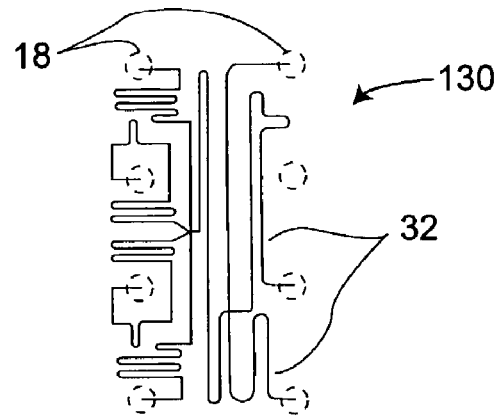
FIGS. 10A and 10B illustrate a mobility shift assay microfluidic network and assay test results at different concentrations.
Figure 10B:
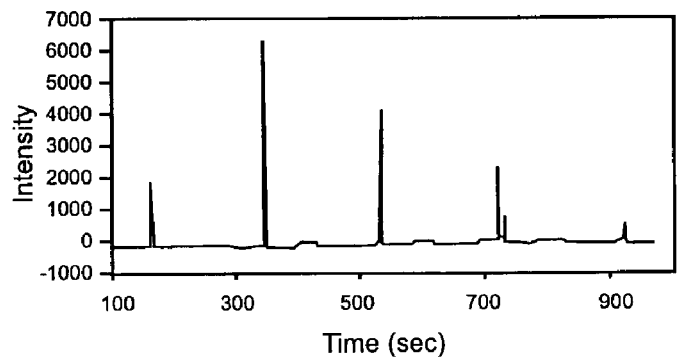

Additional exemplary assay reactions, assay results, and microfluidic networks to provide those results are illustrated in FIGS. 9A through 10B. More specifically, FIGS. 9A–C illustrate the reaction and assay results for a Protein Kinase A (PKA) assay performed at different ATP concentrations. FIG. 10A illustrates a chip design having a microfluidic network 130 of microfluidic channels 32 connecting reservoirs 18, in which the network is adapted for a mobility shift assay. FIG. 10B are exemplary results of a mobility shift assay at different concentrations of ATP as can be measured using the chip design of FIG. 10A.

Figure 11A:
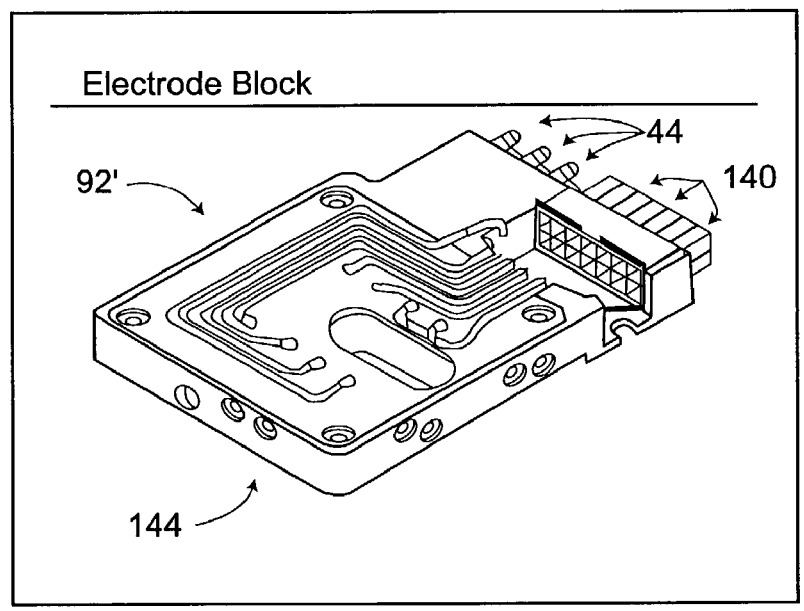
FIGS. 11A and 11B are a perspective and plane view, respectively, of an exemplary hydrodynamic and electrokinetic interface structure for coupling to a microfluidic body.
Figure 11B:
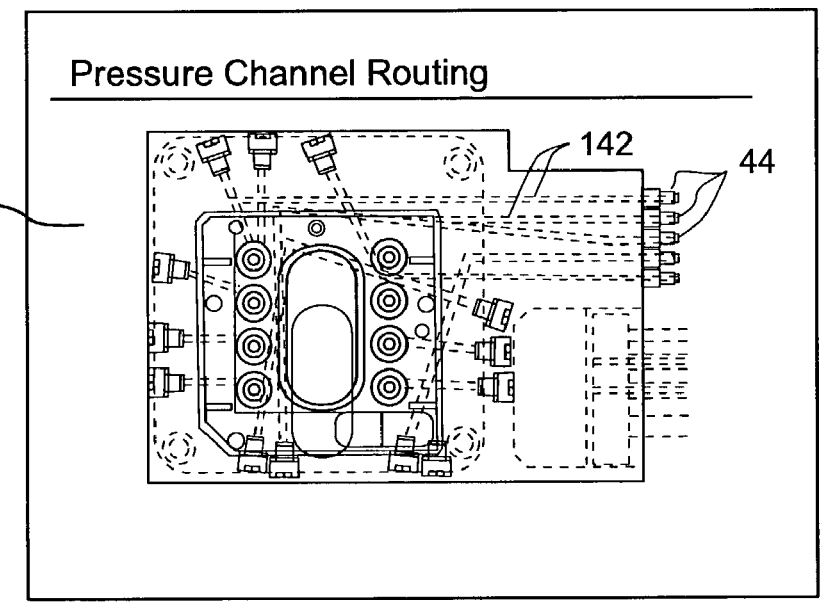

Referring now to FIGS. 11A and 11B, an exemplary manifold or chip interface structure 92' is illustrated in more detail. Exemplary manifold 92' is adapted to provide both hydrodynamic coupling and electrokinetic coupling between a microfluidic body and an associated controller, as described above. Electrical conduit passages 140 for coupling electrodes 94 to a system controller 22 (see FIG. 6) are illustrated in FIG. 11A. FIG. 11B illustrates manifold pressure transmission lumens 142 which provide fluid communication between fittings 44 and a microfluidic body interface surface 144 within manifold 92. Manifold lumens 142 are illustrated in phantom.

Accurate control of the flow of fluids within a network of microfluidic channels can be quite challenging within even a relatively simple network of channels. More specifically, in many microfluidic applications, a variety of different fluids (with different characteristics) can be present in a single channel segment. As described above, where the hydro-resistance of each channel segment can be obtained, it can be possible to simulate and calculate the flow of fluids throughout the network for a given pressure configuration. Unfortunately, it can be quite difficult to accurately calculate viscosities (and, hence, resistances and flow rates) when several different buffers are used within a channel, often together with one or more different test fluid samples.

Fortunately, a relatively simple flow sensor can be provided to measure an actual flow within a channel of a microfluidic network. Where the measured flow results from a known driving force (such as a known pressure differential) can be determined, pressures to be applied at the fluid reservoirs so as to affect a desired flow condition can then be calculated.

Figure 12:
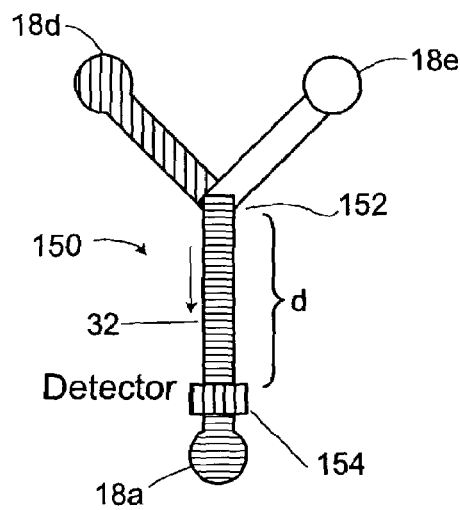
FIG. 12 schematically illustrates an exemplary microfluidic viscometer.

Referring now to FIG. 12, a relatively simple viscometer 150 makes use of a channel intersection 152 at a first location and a detector 154 at a second location to measure fluid flow characteristics. In general, a steady-state flow within a microfluidic channel 32 between intersection 152 and sensor 154 can be produced using a pressure differential between reservoirs 18, as described above. Intersection 152 can impose a signal on the steady-state flow by applying a pressure pulse to one or more of the reservoirs 18, by applying an electrokinetic pulse across intersection 152, or the like. The signal imposed at intersection 152 will often be in the form of a small flow perturbation, typically for a short duration. For example, where reservoir 18d includes a detectable dye, the flow perturbation or signal can comprise an increase or decrease in the dye concentration in the flow of microfluidic channel 32 from intersection 152 toward detector 154.

Detector 154 is downstream from intersection 152, and can be used to detect the arrival time of the signal, for example, as a peak or dip in the intensity of a fluorescent signal from the dye. Thus, the time difference between imposition of the signal at intersection 152 and sensing of the signal flow at detector 154 can be readily measured. Calling this time differential $\Delta t$, and knowing the distance along channel 32 between intersection 152 and detector 154, $\Delta d$, from the microfluidic network geometry, the flow rate Q can be calculated from the equation:

$$Q = A(\Delta d / \Delta t)$$

in which A is the cross-sectional area of the channel. This measured flow rate of a steady-state flow for a given initial driving force greatly facilitates calculation of an appropriate pressure configuration to achieve a desired flow.

While the use of a pressure-controlled microfluidic flow generator (such as modulator bank 14) has significant advantages, alternative flow generators can be used. Volume-controlled microfluidic flow generators, for example, can also be used in a microfluidic system to measure viscosity. A constant (or otherwise controlled) volumetric flow can be driven through a channel segment of a microfluidic network using known nanoliter scale syringe pumps. By measuring the pressure differential $\Delta P$ along the segment, and using the known volumetric flow Q generated by the pump, the flow resistance through the segment can be calculated. Viscosity can be determined from known channel characteristics and the flow resistance, and/or can be derived using calibration data generated by driving reference fluids having known viscosities through the channel segment. Still further alternative flow generator means might be used, including capillary or spontaneous fluid injection, electrically induced flow, and the like.

Where viscosity is to be determined by the system of FIG. 12, reservoirs 18d and 18e coupled to channel 32 by intersection 152 can individually or in combination introduce fluid of known or unknown viscosity into the microfluidic channel at the intersection to provide a flow within the channel having an unknown total flow resistance. With channel 32 optionally containing only a trace amount of fluorescent dye (to inhibit any effect of the dye on the unknown overall viscosity), a substantially constant pressure configuration at ports 18 can drive flow from intersection 152 toward detector 154. This steady-state flow condition can be effected by a constant vacuum at reservoir 18a adjacent detector 154, positive pressures applied at reservoirs 18d, 18e adjacent intersection 152, or a combination of both. Regardless, the steady-state flow with a constant pressure differential will result in a volumetric flow rate Q in channel 32 which is linearly proportional to the pressure differential $\Delta P$ and inversely proportional to the fluid viscosity $\eta$ as follows:

$$Q = K\Delta P/\eta$$

K is a proportionality constant which depends on the geometry of the channel network. K can be calculated from the channel geometry, or can be determined through a calibration standard test, or the like.

When a pressure pulse is used to induce a flow perturbation giving rise to a fluorescence intensity perturbation in viscometer 150, symmetric pressure pulsing can be applied at reservoirs 18d and 18e such that the node pressure at 152 is unchanged to maintain a constant flow rate Q in channel 32 during the introduction of the dye pulse. This symmetric pulsing scheme mitigates the error in flow rate introduced by the perturbation. It also allows the use of a relative long pulse to provide a good signal-to-noise in the measured signal, even with a significant amount of flow-induced dispersion. An alternative embodiment is to use symmetric pressure stopping from reservoirs 18d and 18e. In this case, the flow from 18d steps down sharply in time as compensating flow from 18e steps up simultaneously. The total flow Q in channel 32 is maintained, and the fluorescent intensity goes up and down as a step function (rather than a pulse). The arrival time of the propagation front of the dye (at 50% height of the final intensity value, for instance) can be used to determine the time differential $\Delta t$.

A variety of alternative structures can be used to sense flow characteristics so as to apply a proper pressure configuration to generate a desired flow. For example, a signal can be imposed on a flow within a microfluidic channel by photobleaching of a fluorescent dye, rather than imposing a flow perturbation at a intersection. Alternative flow velocimetry approaches such as laser Dopler velocimetry, tracer particle videography, and the like are also possible. Using such techniques, a simple straight channel connecting a fluid supply reservoir and a waste fluid reservoir can suffice, with the fluid supply reservoir containing a fluid comprising a photobleachable fluorescent tracer dye or appropriate tracer particles.

As can be understood with reference to the calculations of flow rate Q above, sensors can also be used to determine alternative flow characteristics within a microfluidic channel, including flow rate, viscosity, the proportionality constant for a segment or network (by use of fluids having known and/or uniform viscosities) and/or other flow characteristics. In fact, in addition to providing a tool to study effective viscosity of two or more mixed fluids (of optionally unequal viscosity) still further measurements are possible. Mixing of DMSO and an acquiesce buffer can yield a non-monotonic viscosity-composition relationship. By applying different levels of pressure differential $\Delta P$ and measuring the flow rate Q, viscometer 150 could be used to establish a relationship of the effective viscosity during mixing as a function of mixing length. This information can be pertinent to chip design for tests which involve geometric dilution.

Where temperature dependency of viscosity is of interest, systems such as viscometer 150 can be coupled to a temperature control system comprising an external heater block in contact with the body defining the microfluidic channel network, by using joule heating to selectively control the temperature of fluids within the channel network, or the like. In a still further alternative, a structure similar to viscometer 150 might be used to measure non-Newtonian viscosity. Non-Newtonian fluids have viscosities which are a function of the sheer rate experienced by the fluid. One example of a non-Newtonian fluid is a polymer solution containing high molecular weight molecules. A microfluidic viscometer similar to viscometer 150 of FIG. 12 might have a channel geometry and/or channel network intersection structure and/or flow arranged so that the application of a pressure differential creates a range of sheer stresses so as to accurately measure such non-Newtonian viscosity.

Figure 13A:
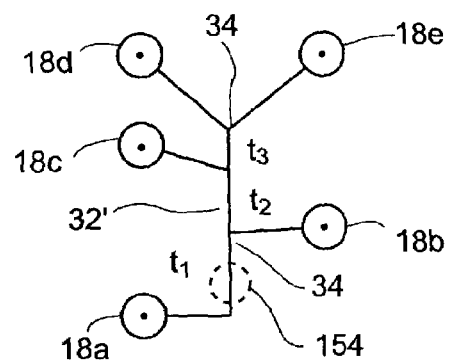
Figure 13B:
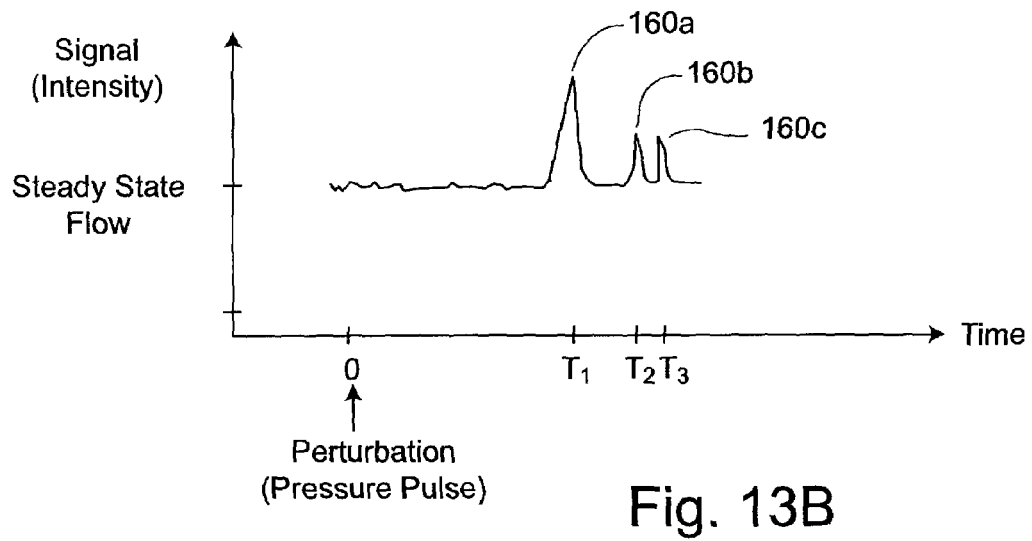

Real-time flow control and viscosity measurements for microfluidic systems based on transient pressure pulse techniques can be further understood with reference to FIGS. 13A and 13B. A microfluidic network structure 30 with a single branch channel coupling each node to a main channel 32' is used. Each branch can be connected to a single reservoir 18 for a different buffer, sample, enzyme, or like. In the simplest embodiment, reservoir 18e at the end of the microfluidic channel network contains a dye solution to provide a detectable signal.

A steady flow can be directed toward reservoir 18a by applying initial pressures on wells 18. A short pressure pulse can be applied to well 18e and/or some or all of the other reservoirs of the microfluidic system. This pressure pulse will propagate substantially instantly to alter flow at some or all of the intersections 34 of network 30. This disturbance of the flow at the node points can change the dilution ratio from one or more of the side branches. After the pressure pulse, steady state flow is resumed.

As can be understood with reference to FIG. 13B, a time series of signals 160a, 160b, and 160c occur at times $T_1$, $T_2$, and $T_3$, respectively. The flow rate from some or all of the side branches can then be obtained from the difference of flow rates between successive node points. Once the flow rates of the branches have been obtained, as the pressures at reservoirs 18 are known, the resistances of the branch channels can then be calculated. From the known channel geometry, the viscosity of the solution mixtures in main channel 32' can be calculated once the viscosities of the solutions in the side branches connecting to reservoirs 18b, 18c, 18d, and 18e are known. This information can then be fed back to the network model to derive the pressures for a desired flow rate from each reservoir.

In addition to providing the benefit of flow rate control, the flow perturbation technique also facilitates measuring viscosities of solution mixtures. For the network shown in FIG. 13A, the transit time $T_3$ is a function of the viscosity of the mixture from 18d and 18e, $T_2$ is a function of the viscosity of the mixture from 18c, 18d, and 18e, and $T_1$ is a function of the viscosity of the mixture from 18b, 18c, 18d, and 18e. Therefore, the microfluidic structure 30 can be used as a viscometer for multi-component solution mixtures. The fluid mixtures are dispensed and mixed microfluidically within the network. The composition of the solution mixture in the main channel 32' can easily be varied by changing the pressures at the reservoirs thus changing the flow ratio from each side branch. Consequently, the complete behavior of viscosity as a function of composition can be mapped out relatively quickly with this method.

Figure 13C:
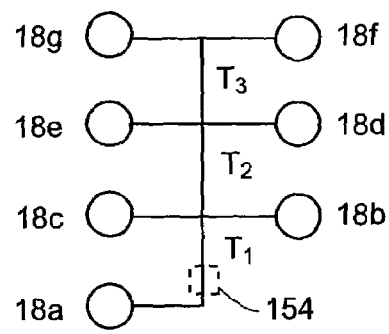

The design of a viscometer for solution mixtures can be further refined to take advantage of the symmetric pressure pulsing and symmetric pressure stepping techniques of the detectable fluid. An example microfluidic structure is shown in FIG. 13C for a 3-fluid system. In this structure, each fluid reservoir has a paired well containing the same fluid with trace fluorescent dye. Fluid 1 with and without dye can be loaded in reservoirs 18g and 18f, respectively, fluid 2 with and without dye in 18e and 18d, respectively, and fluid 3 with and without dye can be loaded in reservoirs 18c and 18b, respectively. As a pressure gradient is applied to induce flow toward reservoir 18a, symmetric pressure pulsing applied at each of the pairing reservoirs can be used to keep the node pressures at all channel intersections constant, thus maintaining constant flow rates and mixture composition in the main channel. The arrival times $T_1$, $T_2$, and $T_3$ of the pulses can be used to calculate mixture viscosities as discussed before. Alternatively, symmetric pressure stepping applied at each of the pairing reservoir yields the same advantages by analyzing the arrival times of the dye fronts rather than dye pulses.

Figure 14A:
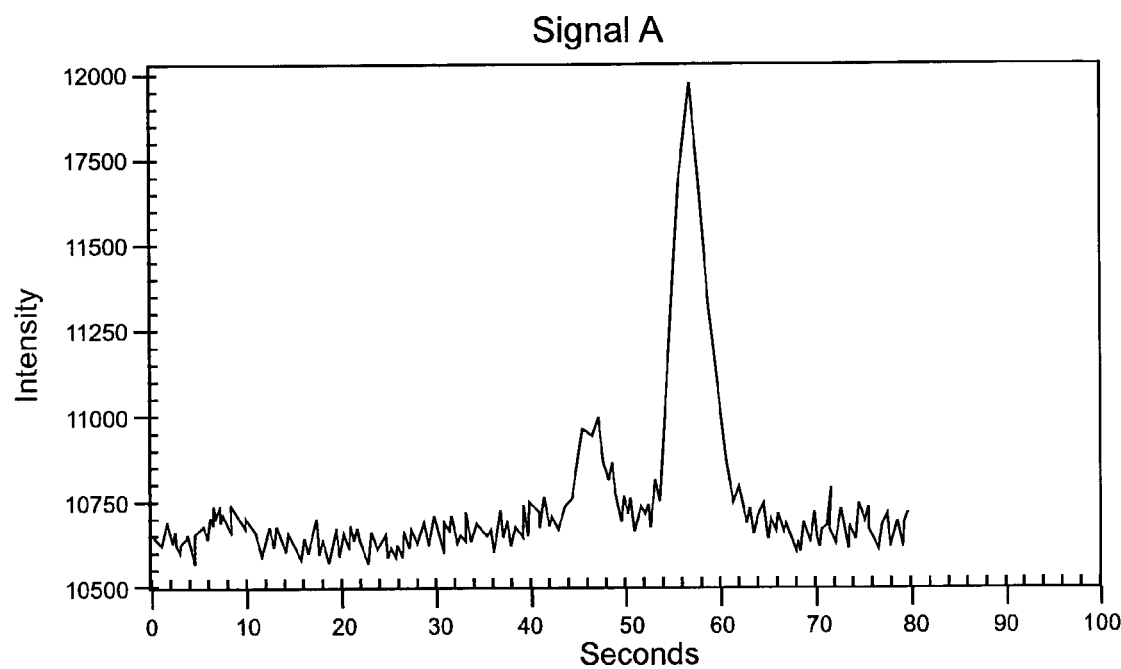
FIGS. 14A and 14B graphically illustrate flow characteristic signals which can be used to determine effective viscosity.
Figure 14B:
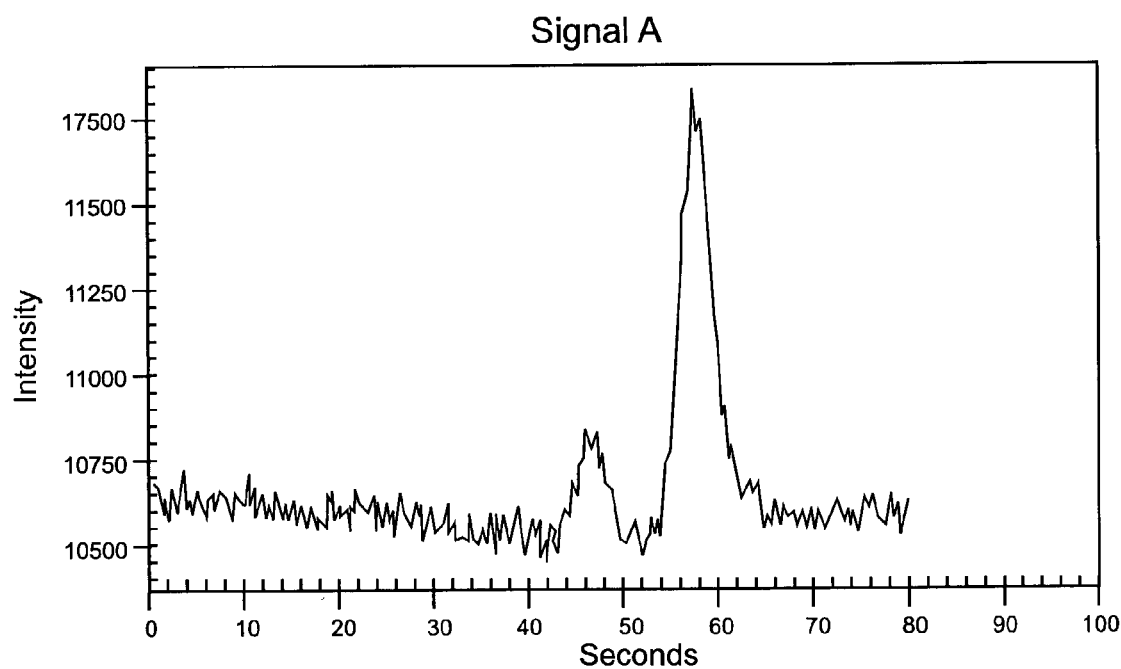

Referring now to FIGS. 14A and 14B, exemplary time signature data indicates that pressure pulse signals can effectively be imposed on the flow within a microfluidic system, and can accurately and repeatedly be sensed by a detector (such as an optical detector, or the like) for measurement of flow characteristics.

Hydrodynamic, electrokinetic, and other fluid transport (flow induction) mechanisms can be used in a variety of ways to provide specialized functions within a microfluidic system. For example, fluid mixtures such as biological fluid samples having particulates and/or cells in suspension within a liquid are often introduced into microfluidic systems. A particularly advantageous system and method for introducing a large number of samples into a microfluidic system is described in U.S. Pat. Nos. 5,779,868 and 5,942,443, the full disclosure of which is incorporated herein by reference. In that system, a vacuum can be used to draw a sequential series of fluid samples from the wells of a multi-well plate into a capillary tube in fluid communication with the microfluidic system.

In the above-described system, it can be desirable to maintain fluids at a substantially stationary location within the microfluidic channel, for example, during the time delay while a sample in a last well of a first multi-well plate is moved away from the capillary tube and before a sample in a first well of a second multi-well plate is in fluid communication with the capillary tube. Maintaining the fluids within the microfluidic channel at a substantially fixed location can avoid introducing significant amounts of air into the microfluidic system, which might interfere with its operation. It can be desirable to maintain fluid mixtures at a given location within a microfluidic network for a wide variety of reasons.

Unfortunately, work in connection with the present invention has found that halting movement of some fluid mixtures within a microfluidic network can have significant disadvantages. Specifically, cell-based assays performed using a fluid mixture including cells suspended in a liquid are susceptible to sticking of the cells to the channel walls if flow is completely halted. Similarly, other fluids can deteriorate if flow within the channel is sufficiently low for a sufficient amount of time.

To avoid deterioration of fluid mixtures, the present invention can provide a small amplitude oscillatory movement of a fluid mixture so as to maintain the fluid mixture within a microfluidic channel. Modulator bank 14 is capable of providing a small amplitude oscillatory pressure such that there is no significant inflow or outflow of materials from the channel. This small amplitude oscillatory pressure will preferably be sufficient to continuously move the fluid mixture (and, for example, the cells within the liquid) continuously back and forth. The oscillation frequency should be high enough such that the instantaneous fluid mixture velocity is sufficiently high to avoid deterioration of the mixture, while amplitude should be small enough such that there is little or no unintended net transportation into or out of the channel from adjacent reservoirs, reservoirs and intersecting channels. Once the desired delay in fluid mixture movement has been provided it will often be desirable to flow an intervening liquid such as a buffer into the channel to help insure that unintended flows and/or mixtures at the channel ends have been flushed.

It should be noted that this small amplitude oscillatory motion can optionally be provided using electrokinetic forces, such as providing an alternating current, particularly if the alternating current is not harmful to cells or other components of the fluid mixture. It can be beneficial to insure that cells in the channel do not lyse when subjected to the alternating current if electrokinetic forces are to be used to induce the oscillatory motion.

Figure 15:
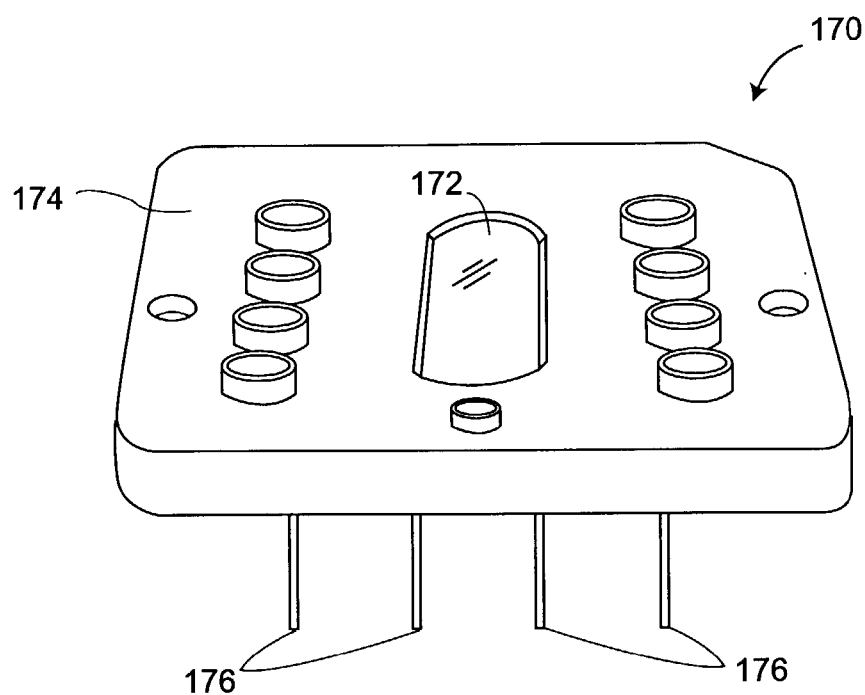
FIG. 15 is a perspective view of a microfluidic chip having a plurality of capillaries for spontaneous injection of fluids into the microfluidic network, typically by introducing the capillaries into fluid sources to bring the fluid into the chip in a controlled fashion.

Referring now to FIG. 15, the systems and methods described above can optionally take advantage of a wide variety of pressure transient generators so as to initiate a flow perturbation. A multiple capillary assembly 170 includes a microfluidic body or chip 172 mounted a polymer interface housing 174. A plurality of capillaries 176 contain fluid introduction channels. As explained in detail in U.S. Pat. No. 6,149,787, the full disclosure of which is incorporated herein by reference, the capillary channels can be used to spontaneously inject fluids into the microfluidic network of chip 172 using capillary forces between the injected fluid and the capillary channels. Such spontaneous injection is sufficient to induce a pressure transient for measurement of hydrodynamic and/or electrokinetic flow. Such flow measurements allow the derivation of information regarding the properties of the chip, microfluidic network, and/or fluids.

Figure 16:
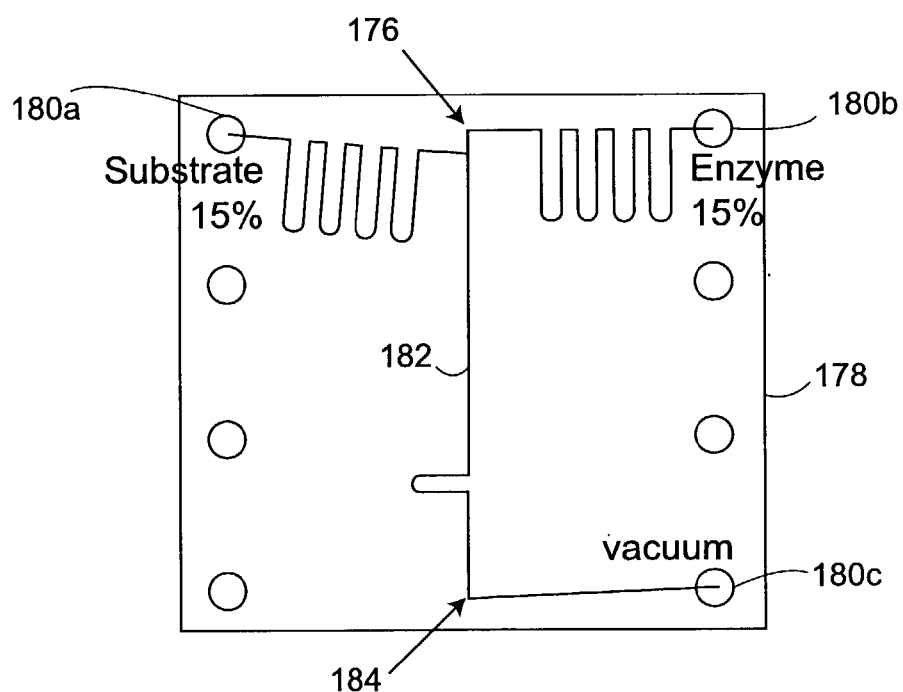
FIG. 16 is a top view of a simple microfluidic chip having a single capillary for spontaneous injection.

The use of multiple capillary assembly 170 is beneficial for parallel assays using a plurality of test samples, and the like. Referring now to FIG. 16, a simple chip 178 having a relatively straightforward microfluidic network can be used to understand the derivation of flow and/or chip properties from spontaneous injection. In many embodiments, the open end of capillary 176 will be placed in a fluid, typically by introducing the end of the capillary into a microtiter plate (or any other structure supporting one or more fluid test samples). This can be effected by moving the capillary 176 and chip 178 relative to the microtiter plate, by moving the microtiter plate relative to the capillary or by moving both structures relative to each other. Regardless, placing capillary 176 into a fluid results in spontaneous introduction of the fluid into the capillary channel. By applying a constant vacuum on at least one well of the microfluidic system, a steady flow can then be provided along a channel coupling the capillary to the well.

If, for example, a steady-state flow is induced from capillary 176, a substrate reservoir 180a, and/or an enzyme reservoir 180b toward a vacuum reservoir or waste well 180c along a channel 182, a flow perturbation can be initiated at intersection 186 between the capillary channel and the microfluidic network at the time the capillary is withdrawn out from the well containing the introduced fluid. This flow perturbation can, for example, comprise a change in composition of the flow progressing along channel 182 toward vacuum reservoir 180c. This change in composition can be sensed at a detection location 184 as, for example, a change in fluorescent intensity. Similar flow perturbations might be induced by applying other pressure transients at intersection 186, for example, when capillary 176 is introduced into the spontaneously injected fluid, or by applying a change in pressure using a pressure modulation pump as described above, again changing the composition of the flow within channel 182. By monitoring the property of the composition at detection point 184, progress of the perturbations can be detected. A time delay between initiation of the perturbation and their respective detections at the detection point, when combined with a known length of channel 182, can be used to determine a speed of the flow within the channel. From this actual, real-time speed, a variety of information regarding the fluid and/or network system can be determined.

Figure 16A:
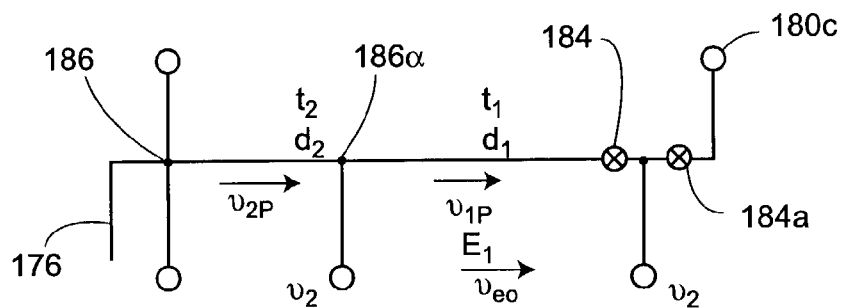
FIGS. 16A–16C graphically illustrate methods for monitoring progress of perturbations induced by spontaneous injection of fluids, for use in determining characteristics of a flow and/or microfluidic network.
Figure 16B:
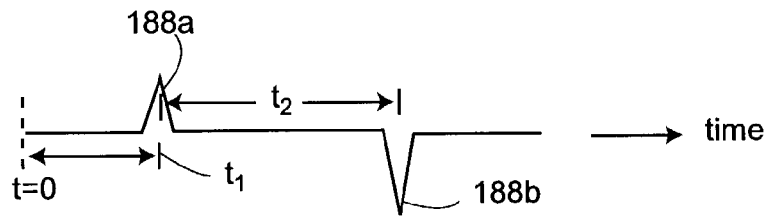

Referring now to FIGS. 16A and 16B, each time capillary 176 is dipped into and are removed from a fluid well, a perturbation will be generated at a capillary intersection 186 coupling the capillary channel with the microfluidic network. Additionally, as the pressure perturbation will propagate throughout the microfluidic network, another flow perturbation can be simultaneously initiated at a second intersection 186a downstream of the sipper intersection 186. If we assume that fluid is flowing from reservoirs affixed to the microfluidic network toward a vacuum reservoir 180c, the pressure transient applied by spontaneous injection at capillary 176 will alter the mixtures occurring at each intersection.

Where the channel lengths can be designated, and $\Delta d_1$, $\Delta d_2$ a time delay can be measured at detector 184 between initiation of the pressure transient (at t=0) and sensing of a first flow perturbation as a signal 188a at detector 184. The first signal 188a can be said to have occurred after a time delay of $\Delta t_1$, with this time being the time required for flow to propagate from the intersection immediately upstream of detector 184. A similar time delay $\Delta t_2$ will then be required for the flow to propagate from the second upstream intersection (186 in the simple network of FIG. 16A). Where the channel lengths between intersection are known, the various time delays can be used to determine the various fluid speeds between intersections. Where the channel cross-sections are known, this information can be used to determined contributions from branch channels to the flow volume, and the like, regardless of whether the flows throughout the microfluidic system are induced hydrodynamically, electrokinetically, electroosmotically, or the like.

Figure 16C:
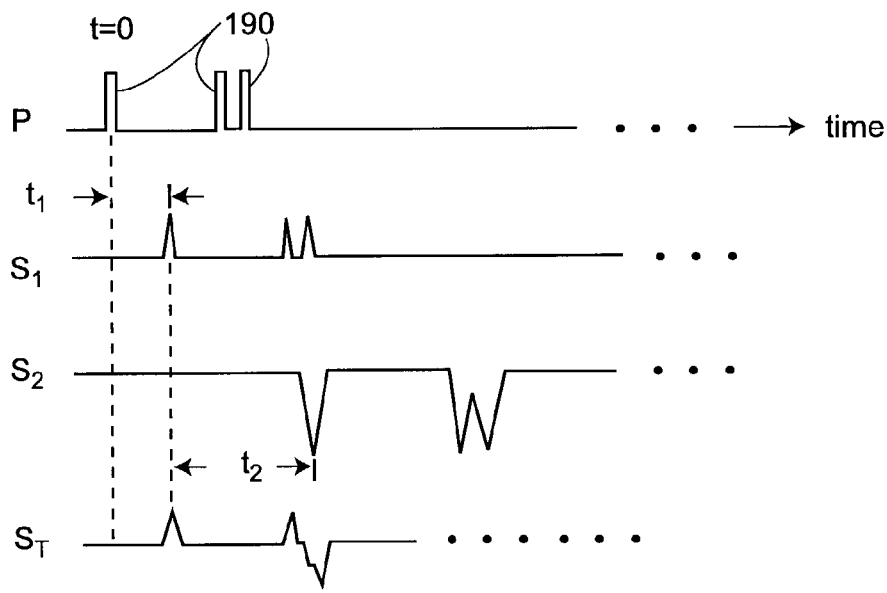

Referring now to FIG. 16C, capillary 176 can be dipped into and removed from a variety of fluids in a sequential series. P indicates pressure, $S_1$ is a signal indicating a flow perturbation caused at a first intersection by spontaneous injection into the capillary, and signals $S_2$ indicates a flow perturbation signal generated at a second intersection by the same spontaneous injection at the capillary. A series of pressure transients 190 will be generated by capillary 176 when the capillary is, for example, dipped into and removed from a dye, followed by dipping of the capillary into a buffer solution, followed dipping of the capillary into a first test substance well, and the like. This sequence of spontaneous injection events at capillary 176 can result in generation of a series of $S_1$ signals due to a series of flow perturbations at, for example, intersection 186a. Simultaneously, a series of second flow perturbation signals $S_2$ will also be generated at intersection 186, with detection of the second series following the first series by a time delay $\Delta t_2$ which is dependent on the speed of fluid within the network channels. The total signal $S_t$ measured at detector 184 will be a combination of this offset series of signals with the more immediate $S_1$ signals. Furthermore, the composition of the overall flow arriving at the detector can vary significantly with the different materials introduced by capillary 176. Regardless, by properly identifying the time delays between signals, flows between the nodes of the microfluidic system can be calculated.

Referring now to FIG. 16A, placing a detector 184a downstream of an electrode $v_1$ can facilitate measurements of electrically induced flow, such as electroosmotic flows induced by a differential voltage between $V_1$ and $V_2$. As described above, pressure perturbations will be initiated at the channel intersections, so that an initial signal can be generated at the detector from the downstream electrode $V_1$, followed by another signal generated at the upstream electrode $V_2$. Setting $\Delta t_1$, as the time delay between these electrode intersections and $\Delta t_2$, as the time delay for a subsequent signal generated by a reaction channel at intersection 186, and knowing the lengths of the channels $\Delta d_1$, $\Delta d_2$ we can calculate the electroosmotic EO flow as follows: With voltage between the electrodes off, using only pressure to drive fluids within the network, we can determine velocities along the channels between nodes caused by pressure $v_{1P}$, $v_{2P}$ from:

$$\frac{\Delta t_2}{\Delta d_2} = v_{2p} \quad \text{and} \quad \frac{\Delta t_1}{\Delta d_1} = v_{1p}$$

While leaving the same pressure differential on, the voltage differential can then be turned on, allowing us to calculate the electroosmotic flow velocity as follows:

$$\frac{\Delta t_2^1}{\Delta d_2} = v_{2p} \quad \text{and} \quad \frac{\Delta t_1^1}{\Delta d_1} = v_{1p} + v_{eo};$$

$$\text{which gives us } v_{eo} = \frac{\Delta t_1^1 - \Delta t_1}{\Delta d_2}$$

Figure 19:
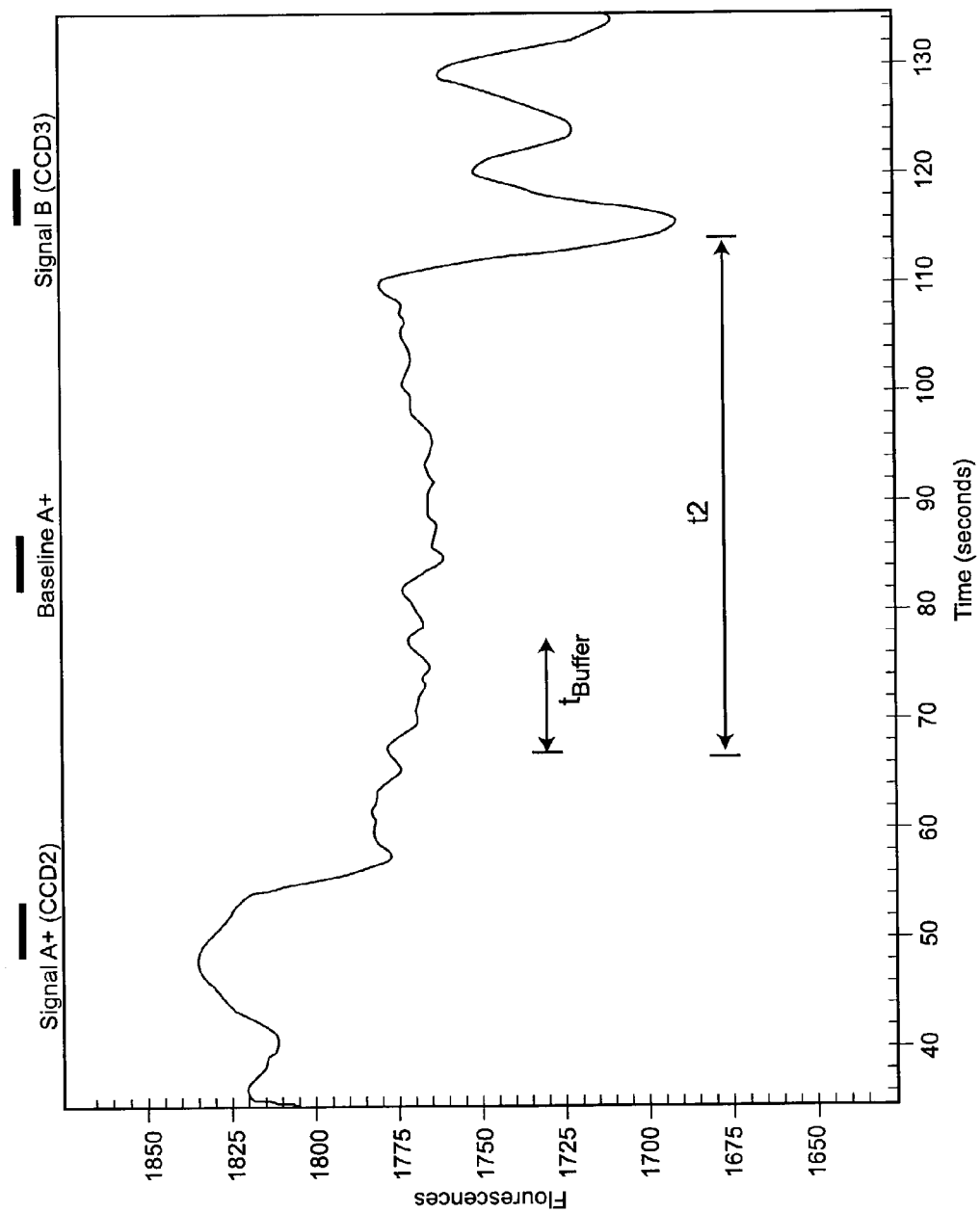
FIG. 19 graphically illustrates the detection of a perturbation generated at an intersection of microfluidic channels by spontaneous injection.

This electroosmotic velocity can then be used to calculate electroosmotic mobility using the equation:

$$\mu_{eo} = \frac{v_{eo}}{E_1},$$

in which $E_1$ is the electric field strength between the first and second voltages $V_1$, $V_2$. FIG. 19 graphically illustrates data from a detector or sensor from which the time delays discussed above can be taken.

The multiple capillary assembly and simplified capillary networks of FIGS. 15, 16 and 16A are examples of microfluidic devices which might benefit from monitoring of pressure induced flow perturbations for analysis and/or control of flows, quality control, and the like. Additional examples of microfluidic structures which can benefit from these techniques are illustrated in FIGS. 17A, 17B, 18A and 18B.

Figure 17A:
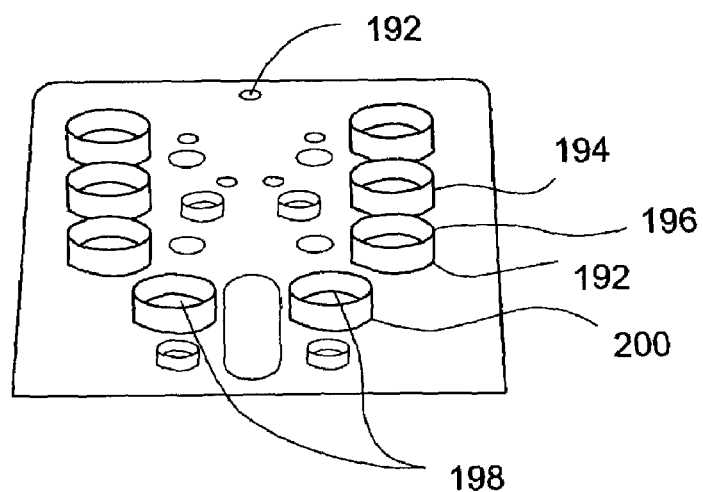
FIGS. 17A and 17B are perspective and plan view of fluorogenic multi-capillary chips.
Figure 17B:
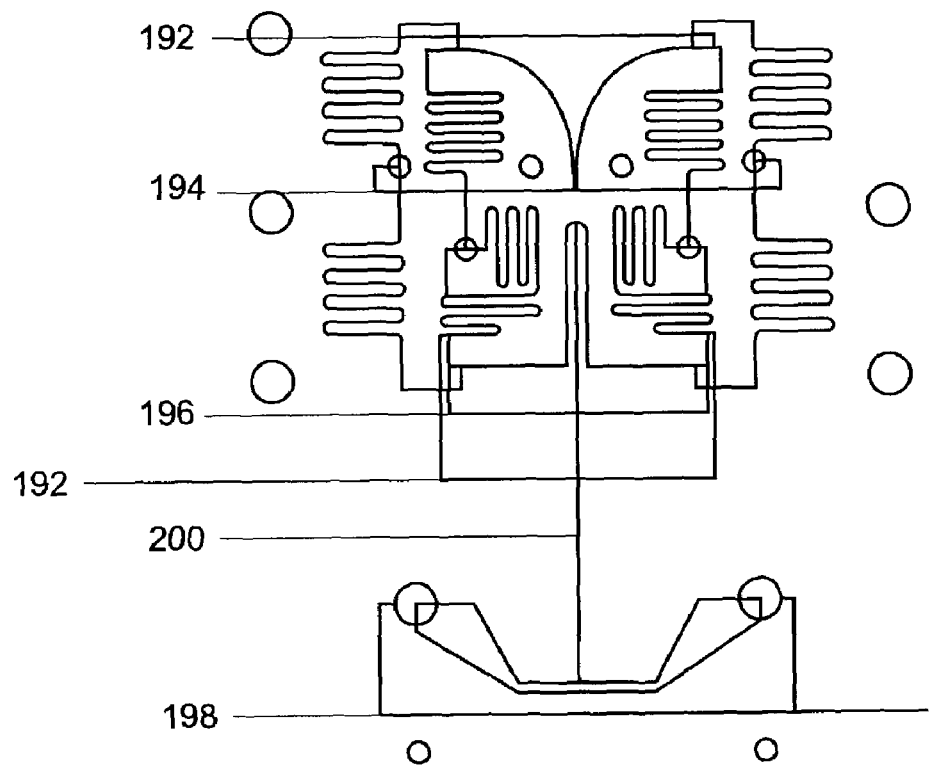
Figure 18A:
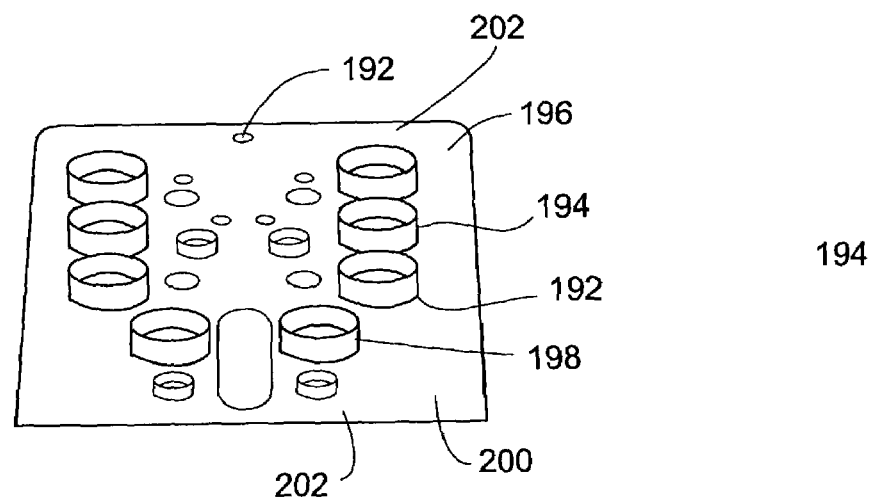
FIGS. 18A and 18B are perspective and plan view of a mobility-shift capillary chip.
Figure 18B:
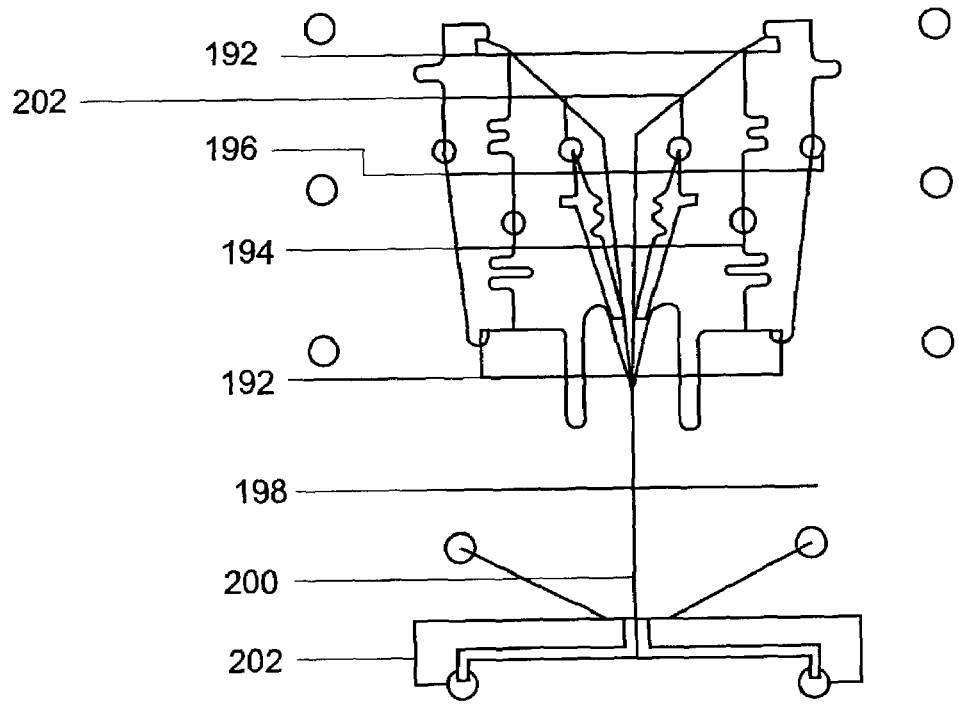

Referring now to FIGS. 17A and 17B, more complex microfluidic networks can include a plurality of capillary joints or intersections 192 and substrate wells or reservoirs 194, enzyme wells 196, waste wells 198, and the like. One or more detection or sensor windows or locations 200 can be provided for monitoring of propagation of the flow perturbations. The microfluidic assembly and network of FIGS. 17A and 17B can be useful for multi-capillary fluorogenic assays. A multi-capillary basic mobility-shift microfluidic assembly and network having similar structures is illustrated in FIGS. 18A and 18B. This structure also includes a plurality of electrode wells 202 for applying voltages to the microfluidic network, as described above.

Accurate control of the flow perturbation pulse can be challenging, particularly where the pulse comprises a step-function change in flow. To decrease noise in measurements, and to generally enhance viscosity measurement accuracy and/or enhance measurement range, it can be beneficial to separate a flow having the perturbation (typically at an intersection within the network) into a plurality of separated flows. A first separated flow might advance along a first separated flow channel, while a second separated flow advances along a second separated flow channel having dimensions (and thus a transit time) different than that of the first separated flow channel. As the channel fabrication tolerances can be better controlled than the pulse, comparison of the transit times through the different channels can allow the magnitude of a step-function pulse to be determined, and thereby allow more accurate viscosity calculations to be made.

Figure 20:
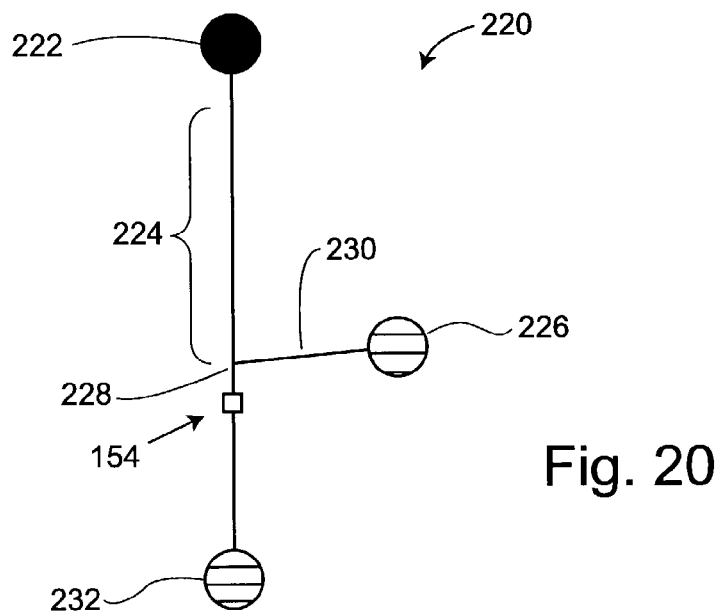
FIG. 20 schematically illustrates a microfluidic network for use in a microfluidic system for determining a viscosity of a sample fluid without adding dyes, or the like, so as to distort the viscosity measurement, and/or to allow the use of dyes that are not compatible with the sample.

Referring now to FIG. 20, a simple microfluidic network 220 for determining a viscosity of a fluid sample is shown schematically. Network 220 includes a sample fluid source 222 which supplies sample fluid to a first flow-resisting channel segment 224. A detectable fluid source 226 is coupled to first segment 224 at an intersection 228 via a second flow-resisting channel segment 230. A sensor or detector 154 is disposed downstream of intersection 228, with the fluid from the sources eventually flowing to a waste well 232 or the like.

In network 220 shown in FIG. 20, the fluid sources and waste well can comprise simple ports or reservoirs as described above. By using this simple arrangement with three wells and a single intersection, viscosities of sample fluids can be determined without mixing the sample fluid with a dye or other detectable substance in such a manner as to alter the viscosity to be measured. Specifically, the channels of network 220 can be completely (often filled using capillary action) with a reference fluid having a known viscosity. The reference fluid used to initially fill the channels of the network can be free from dyes or other detectable substances. The fluid sample can be introduced into sample fluid source 222, and reference fluid having a detectable substance such as a dye can be introduced into detectable fluid source 226. A flow of the fluids within the network can be generated toward waste well 222, for example, by applying a steady vacuum at the waste well.

Figure 21A:
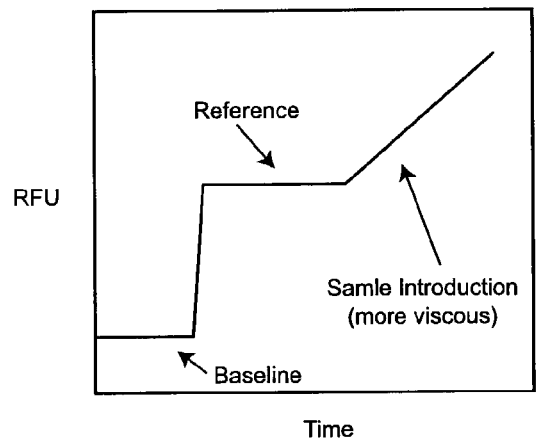
FIGS. 21A and 21B schematically illustrate signals provided by the sensor of the microfluidic network of FIG. 20, allowing determination of a viscosity of a sample fluid relative to a known viscosity of a reference fluid.
Figure 21B:
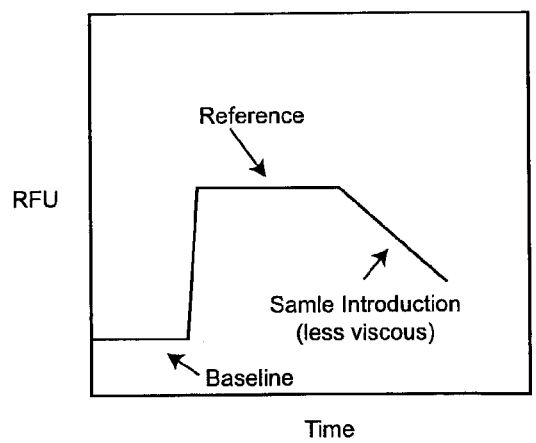

Referring now to FIGS. 20, 21A and 21B, where the reference and detectable fluid have similar viscosities, the dilution of the dye-free reference fluid initially used to fill the channels of network 220 can first be determined by the relative hydrodynamic resistances of the first and second channel segments 224, 230 (the parallel sections of the network circuit), as described below. This can result in a substantially steady signal at the detector 154 after initiation of the flow, (with the baseline signal shown in the figures being generated prior to any flow of the detectable fluid past the detector). Optionally, this initial calibration flow can proceed with reference fluid disposed within sample fluid source 222, and/or with the detectable fluid pre-filling second segment 230. Regardless, this initial flow can be dominated by the flow resistance of the reference fluid within the first channel segment and the detectable fluid within the second channel segment so as to produce a steady reference signal, as schematically shown in FIGS. 21A and 21B.

As a significant portion of the sample fluid is drawn into the first channel segment 224, the ratio between the resistance the first channel segment to the reference fluid and the resistance of the first channel segment to the flow of the sample fluid therein is altered. This results in more or less dye (or other detectable fluid) entering the flow at intersection 228. For example, if the fluid sample is more viscous than the reference fluid initially disposed within the first channel segment 224, the signal will increase at detector 154. This change in signal at the detector results from the change in the percentage of detectable fluid in the combined flow at the detector. As illustrated in FIG. 21A, in our example of a sample fluid having a viscosity higher than that of reference fluid, the signal at detector 154 will increase due to this increased percentage or ratio of detectable fluid at the detector. Similarly, in the case of a sample fluid which is less viscous than the reference fluid, overall resistance of the first channel segment 224 to the flow there through will decrease, and less detectable fluid will be present in the flow at detector 154, resulting in a reduction in the signal generated by detector 154, as illustrated in FIG. 21B. Hence, the relative viscosity of the sample fluid can be determined by comparison to the flow characteristics of the reference fluid. The signals illustrated for FIGS. 21A and 21B can be any appropriate detector signal units, and are schematically shown as Reference Fluorescent Units ("RFU"), as might be appropriate for the use of a fluorescent dye in the detectable fluid. Suitable reference fluids might include, for example, aqueous solutions of ethylene glycol having known concentrations, thereby providing known viscosities from about 1 to about 15 cp. For many embodiments, suitable reference fluids can comprise (or be composed of) water with one or more dye (optionally being diFMU or Fluorescein), a buffer (optionally being a well-known buffer such as HEPES, TRIS, or CAPS at an appropriate pH for the associated dye) and a dye, or the like. Suitable reference fluids can also comprise (or be composed of) a National Institute of Standards and Technology (NIST) (or other standard regulating body) certified viscosity standard, which are generally oils having a known viscosity at a given temperatures. Such viscosity standards are commercially available, and are used for calibration of traditional viscometers.

It should be recognized that the schematic graphs shown in FIGS. 21A and 21B are a simplification. Changes in the signal can begin immediately and/or gradually as the sample fluid enters the flow-resisting segment, and the signal need not be linear.

From the above, it can be understood that the viscosity of the sample can be analyzed as a function of the slope of the fluorescent signal, with positive slopes representing samples that are more viscous than the reference, and negative slopes representing samples that are less viscous than the reference fluid. The relationship between viscosity and the slope of the fluorescence signal will typically not be linear. Nonetheless, the relationship is generally reproducible, so that the relationship can be mapped by fitting a curve (such as a polynomial, an exponential expression, or the like) to the viscosity/signal slope data. The relationship can generally be trendfitted/overlayed on calibration or other measurement data to allow the viscosity to be determined as a function of the signal slope. Still further approaches might be used, including generation of a look-up table and the like.

Still further related methods can be used to determine the viscosity from a sensor signal. For example, as the sample fluid and detectable fluid from the sources fill the channel network and achieve steady state flow, the signal from detector 154 should likewise level off. Hence, the viscosity of the sample fluid can be determined in response to the change in slope of the signal prior to achieving steady-state flow, and/or by using the eventual steady-state signal.

Determination of the viscosity of the sample fluid might be performed using the relative volumetric flow rates through the flow-resisting channel segments as related to fluid viscosity in the equations given above. However, actual resistances to flows within a microfluidic network can be quite sensitive to channel dimensions. Processing and fabrication capabilities can, in turn, limit how tightly the dimensions or tolerances of a particular chop are constrained. As a result, accuracy of viscosity measurement will often benefit significantly from at least one calibration measurement.

Viscosity measurement accuracy will typically be enhanced by taking a plurality of calibration measurements for a specific network, the measurements generally being taken with fluids at a plurality of different known viscosities. As the signal will often vary with changes in viscosity with a non-linear relationship, three or more calibration measurements can be taken with each chip, typically from three to seven measurements. From a plurality of signal slopes or other measurements taken with reference fluids having known viscosities, a calibration curve can be established, and an equation determined fitting the fluid-flow and signal response for a particular microfluidic chip and its network. Measurements taken with the sample fluid will then provide a fluorescence signal (or other) response which can be mapped onto the calibration curve to determine the sample viscosities. Using this reference fluid-based approach the involved calculations can comprise (or even be limited to) derivation of the calibration curve from measurements taken with reference fluids, together with mapping of measurements taken with sample fluids onto the calibration curve to determine sample viscosity.

Figure 22:
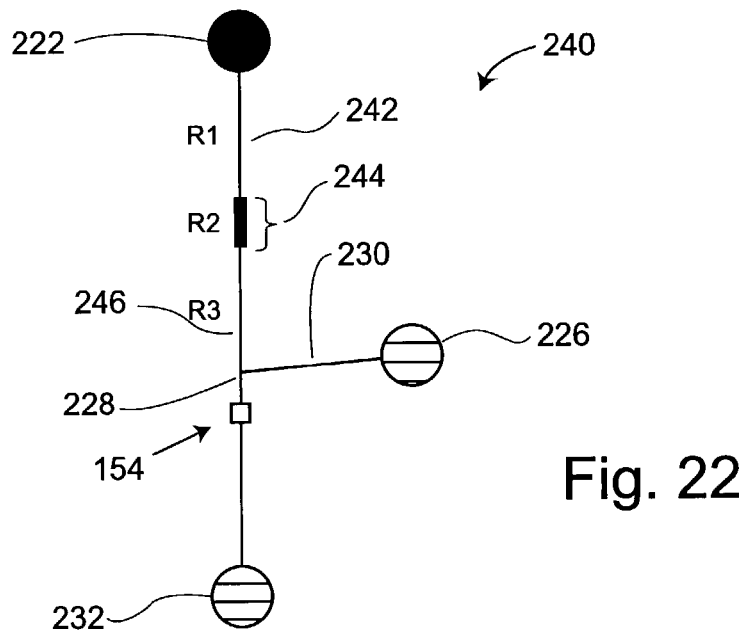
FIG. 22 schematically illustrates a microfluidic network in which a locally enhanced flow resistance region is used as a portion of a viscometer.

A number of network design variations around the general microfluidic viscometer concept described above can be implemented. In some embodiments, alternative (and in some cases slightly more complicated) viscometer channel networks can provide a larger possible dynamic range, enhanced accuracy, greater ease of use, or the like. One alternate viscometry network channel 240 is illustrated in FIG. 22. Network 240 includes many of the components described above regarding network 220, with the flow path coupling the sample fluid source 222 to intersection 228 here comprising a first segment portion 242, a second segment portion 244, and a third segment portion 246. The hydrodynamic resistance of the channel segment portion 244 has been locally enhanced, so that the majority of the flow-resistance of the sample fluid between the sample fluid source 222 and the intersection 228 is imposed along the second channel segment portion 244. This can be effected by altering the depth of the channel along this segment portion, altering the width of the channel segment along this portion, by placing a flow occluding structure within the channel along this segment portion, or the like. Optionally, the bulk of the resistance can be localized within a relatively short channel length, for example, by taking advantage of the strong dependence of the hydrodynamic resistance on the channel depth, and by locally decreasing that channel depth.

Figure 23A:
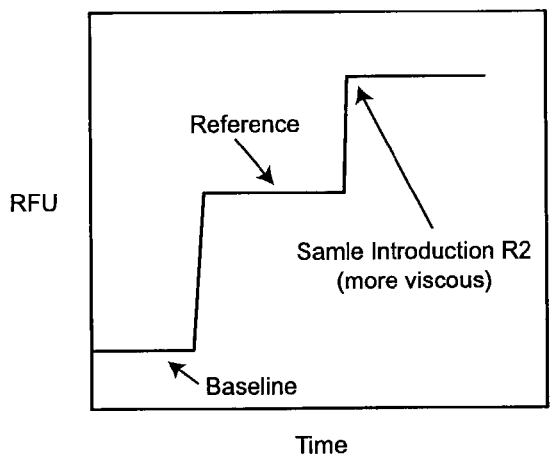
FIGS. 23A and 23B schematically illustrate signals provided by the sensor associated with the network of FIG. 22.
Figure 23B:
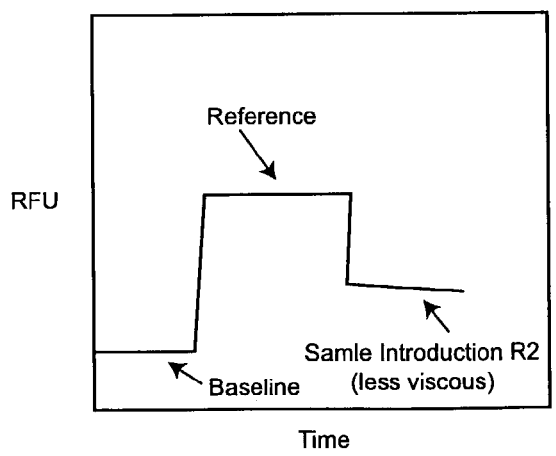

As can be understood with reference to FIGS. 23A and 23B, locally enhancing hydrodynamic resistance R2 along second channel segment portion 244 can help to provide signals from detector 154 which do not change significantly until the flow front has entered and/or filled channel segment 244. After a steeply ramped change in signal, little additional change in the detector signal will occur, assuming that R2 is much larger than R3 or R1. Hence, the signal response to the network 240 would substantially be in a form of a stair step, in which the magnitude of the step is proportional to (or otherwise a function of) the viscosity, with samples having greater viscosity than a reference fluid generating an increased signal as illustrated in FIG. 23A, while sample fluids having a lower viscosity than the reference fluid generating a stair-step down signal as illustrated in FIG. 23B.

Figure 24:
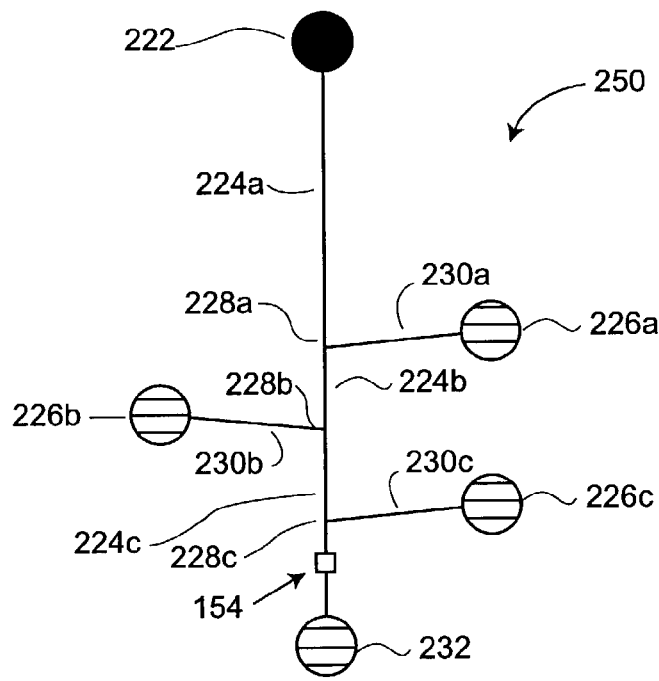
FIG. 24 schematically illustrates yet another alternative microfluidic network for use in a microfluidic viscometer system in which a series of sequential channel segments are coupled to a series of detectable fluid sources at a series of intersections so as to determine viscosities throughout a wide range.
Figure 25:
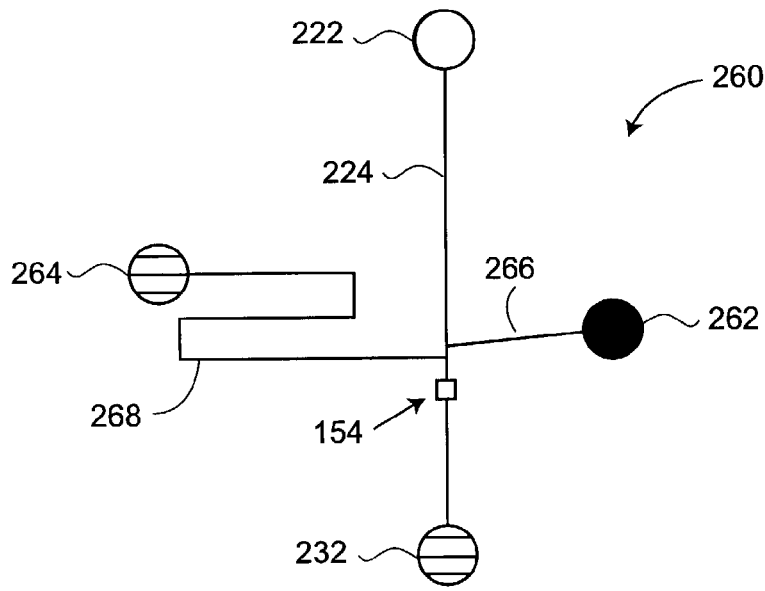
FIG. 25 schematically illustrates a microfluidic viscometry network in which independently detectable fluids are coupled to a sample fluid flow resisting channel by detectable fluid channel segments having differing flow resistance so as to identify sample fluid viscosities throughout a wide range.

It can be advantageous to enhance the dynamic range of a microfluidic viscosity measurement system as can be understood with reference to FIGS. 24 and 25. In network 250 of FIG. 24, a series of flow resisting channel segments 224a, 224b, 224c are aligned in series. Detectable fluid sources 226a, 226b, 226c are coupled to the series flow path by associated channel segments 230a, 230b, 230c at associated intersections 228a, 228b, 228c. This series of hydrodynamic resisters of the sample fluid flow can result in a series of signal plateaus as the sample passes each sequential intersection. By analyzing the relative plateau levels, it will be possible to determine viscosity of the sample fluid, potentially over several orders of magnitude. While three detectable fluid branch channels are shown, two or more can also be used.

In one exemplary embodiment, detectable fluid source 226a and its associated channel of components can provide for detection of viscosities in a range from about 1 to about 10 cp. Similarly, a second detectable fluid source 226b can be used for detection of viscosities in a range from about 10–100 cp, while a third detectable fluid source my provide viscosities in a range from about 100–1000 cp. The variation in sensing range associated with the different detectable fluid sources, is enhanced by the differences in percentage change of flow at the different intersections. Differing side resistances and/or differing detectable fluids having differing signatures (as discussed below regarding FIG. 25), differing detectable fluid viscosities from the differing detectable fluid sources, and the like can also be employed.

Another wide dynamic range network 260 is illustrated in FIG. 25. In this embodiment, a first detectable fluid source 262 includes a first detectable fluid (for example, a dye having a first color signal) and a second detectable fluid source 224, having a second independently detectable fluid (for example, having a dye with a second color signal). Detectable fluid sources 262, 264 are coupled to the first flow-resisting channel segment 224 by a second channel segment 266, and a third channel segment 268, respectively. Segment 266 has a significantly lower hydrodynamic resistance to flow of the first detectable fluid than segment 268 has to flow of the second detectable fluid therethrough. When a vacuum is drawn at waste well 232, a mixture ratio between the sample fluid from sample fluid source 222, and the first detectable fluid can indicated viscosities in a relatively low range (for example, 1–10 cp), while mixing of the sample fluid with the second detectable fluid can indicate viscosities throughout a higher viscosity rating (for example, through out a range of 10–100 cp). Hence, by simply using (for example) dyes having different color together with side channel segments having varying fluidic resistances, the microfluidic viscometry range can be significantly enhanced.

In another embodiment, the viscometer 220 can be used to measure the viscosity of a sample fluid that is immisciable with the detectable fluid. The flow rate of the sample fluid through the capillary is influenced by its viscosity as well as the surface tension properties between the two fluids. The pressure differential across the immisciable fluid interface is determined at least in part by the interfacial tension, the contact angle with the capillary wall, and the radius of the capillary. It is therefore possible to measure interfacial properties between immisciable liquids in addition to sample viscosity by monitoring the changes in the fluorescence intensity signal as a function of time, which is indicative of the sample flow rate as discussed earlier.

Referring back to FIGS. 20 and 6, independent pressure control provided by modulators 14 can also be used to determine viscosity using feedback from sensor 154. A quantity of a sample fluid having an unknown viscosity can be introduced to reservoir 222, through a capillary 176, or the like. Reference fluid can optionally be introduced before and after the sample fluid to produce a "plug" of sample fluid in channel 224, and the viscosity of the sample fluid within the network will affect relative flows at intersections upstream and/or downstream of the plug. A feedback control loop from sensor 154 to pressure modulators 14 allows pressures from port 226 to be adjusted until a desired signal response is achieved. For example, when the plug is first introduced into the main channel, the signal from a dye flowing from reservoir 226 will increase in slope if the plug has a high viscosity. Pressure at reservoir 226 might be decreased until the signal response is flat again. By knowing how much the pressure was changed and the geometry of the chip, one can determine how much the sample fluid has changed the flow resistance in the network, and can thereby determine viscosity of the sample fluid.

Figure 26:
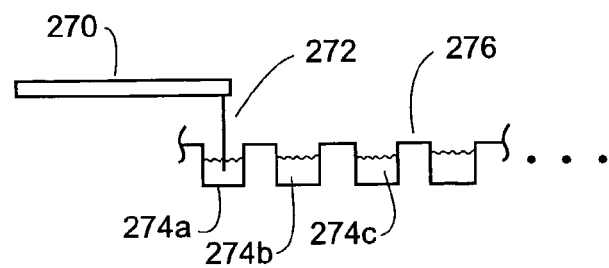
FIG. 26 schematically illustrates a system for sequentially introducing sample fluids into a microfluidic body.

Referring now to FIG. 26, the use of microfluidic viscometry in a high-throughput system can be understood. High-throughput microfluidic systems and methods are more fully described in PCT Publication No. WO 00/10015, the full disclosure of which is incorporated herein by reference. In simple terms, a microfluidic body 270, having channel walls defining the channels of a microfluidic network is coupled to a capillary 272 for entering sample fluids 274a, 274b, and 274c . . . in the channel network. The sample fluids can be disposed in the wells of a microtiter plate 276, with the plate (and/or microfluidic body 270) being moved robotically so as to sequentially introduce the sample fluids through capillary 272. High-throughput systems can also be multiplexed so as to simultaneously determine a plurality of viscosities, optionally with a plurality of capillaries extending from a single body.

To account for variation between capillaries (differences in diameter, coupling of the capillary to the microfluidic network, and the like) it can be advantageous to calibrate the viscosity measurements by introducing a reference fluid from a well of microtitre plate 276. In some embodiments, the bulk of the fluidic resistance can be incorporated in the microfluidic body (rather than the capillary) to reduce the sensitivity of a high-throughput system and method to capillary variability, capillary junction connection variability, and the like.

A variety of alternative microfluidic networks might be used to measure viscosity and/or other fluid characteristics. Using the concepts described above, viscosity might be determined by comparatively measuring flow resistance through a segment of such a network in a manner analogous to the well-known comparative methods used for electrical resistance measurements in the Wheatstone bridge circuit. Such a microfluidic network can be particularly well-suited for viscosity measurements of fluid mixtures, and can also facilitate viscosity measurements throughout a range of dilutions. Other fluid characteristics might also be measure in such a network, including electrical conductivity or the like.

Figure 27:
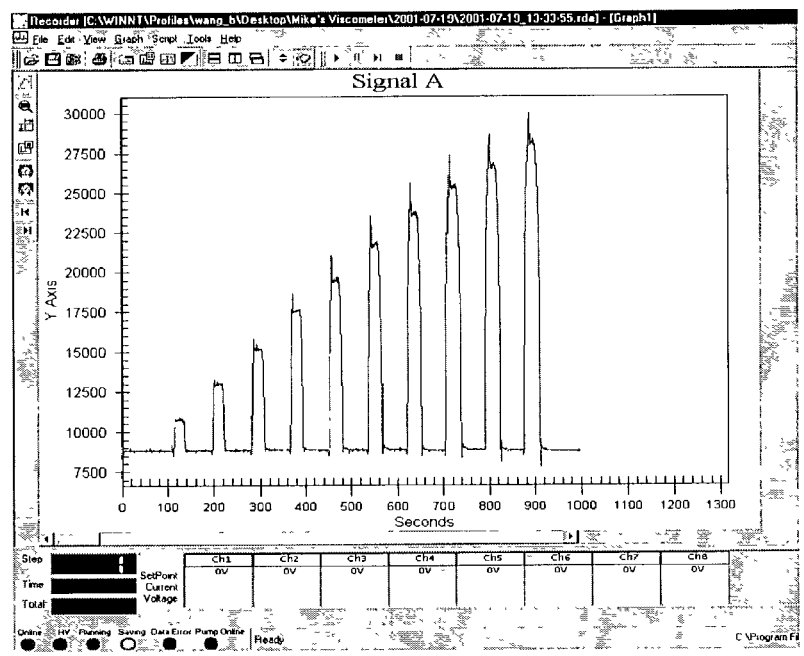
FIGS. 27–33 graphically illustrate measurements and computer model data for determining viscosity and calibrating viscosity measurements.
Figure 28:
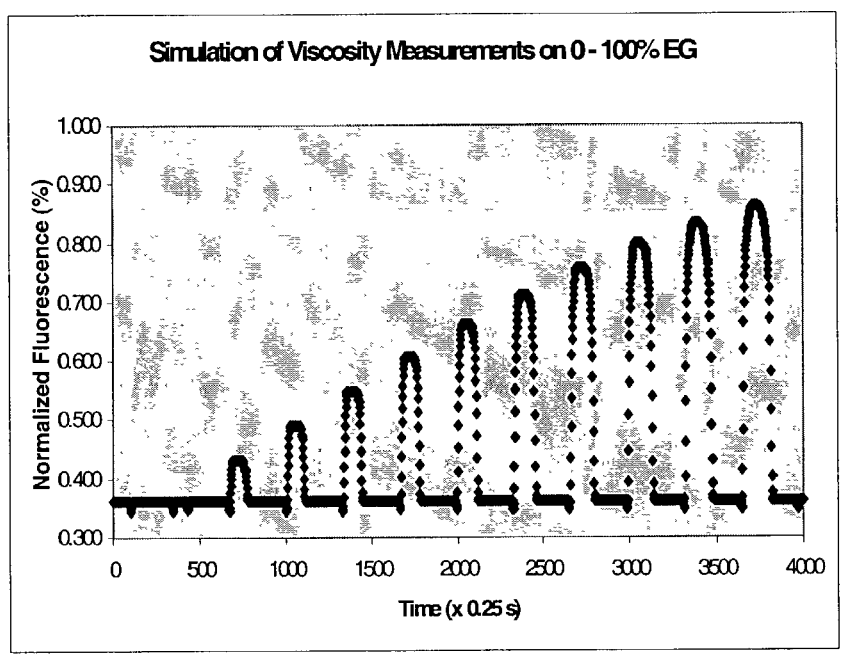

As can be understood from the network design tools described above, a channel simulation program can be helpful in optimizing potential microfluidic viscometer body designs. Calibrations data for a specific microfluidic network can enhance measurements accuracy, as is also explained above. FIGS. 27–33 show measurements and simulated data of viscosities as measured with the microfluidic techniques described herein. Specifically, FIG. 27 shows measurement data generated using a microfluidic chip (NS71, fabrication by Caliper Technologies Corp. of Mountain View, Calif.) by "sipping" (introducing via a capillary 272) sequential 20-second flows of sample fluids having varying viscosities. The sample fluids for these measurements were solutions of ethylene glycol varying from 0 to 100%, providing viscosities varying from about 1 to about 15 cp. FIG. 28 shows corresponding data generated by a computer model or simulation of this microfluidic system.

Figure 29:
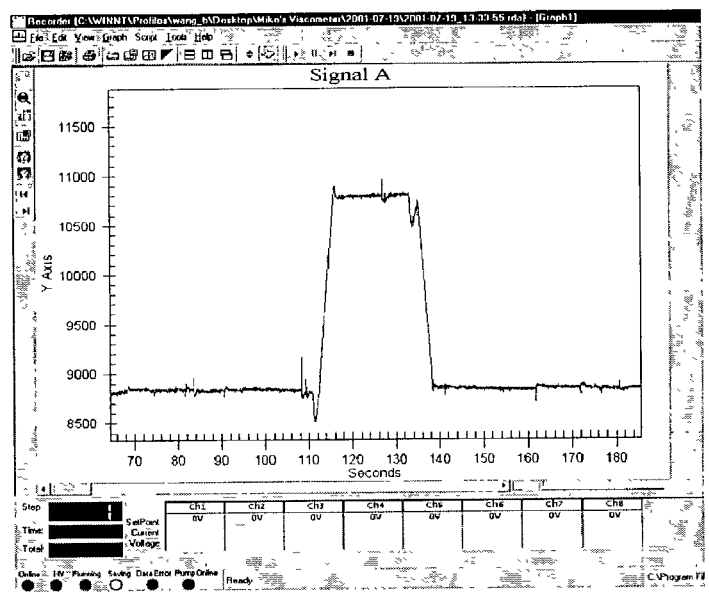
Figure 30:
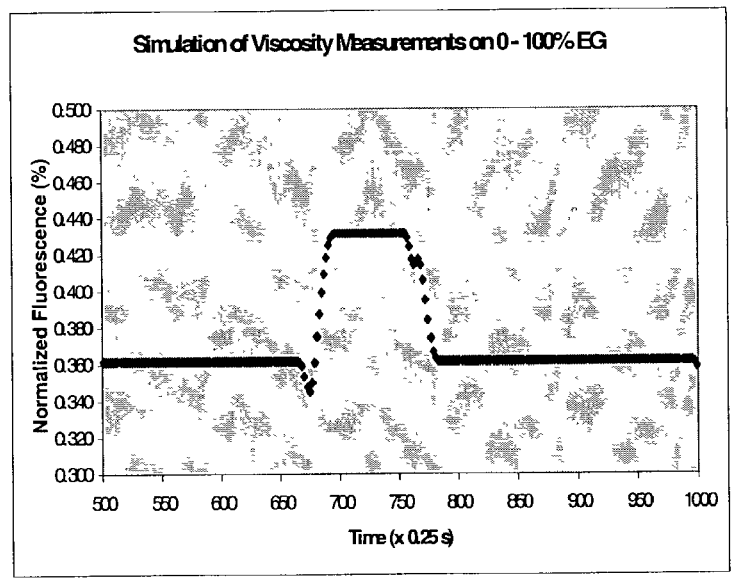
Figure 31:
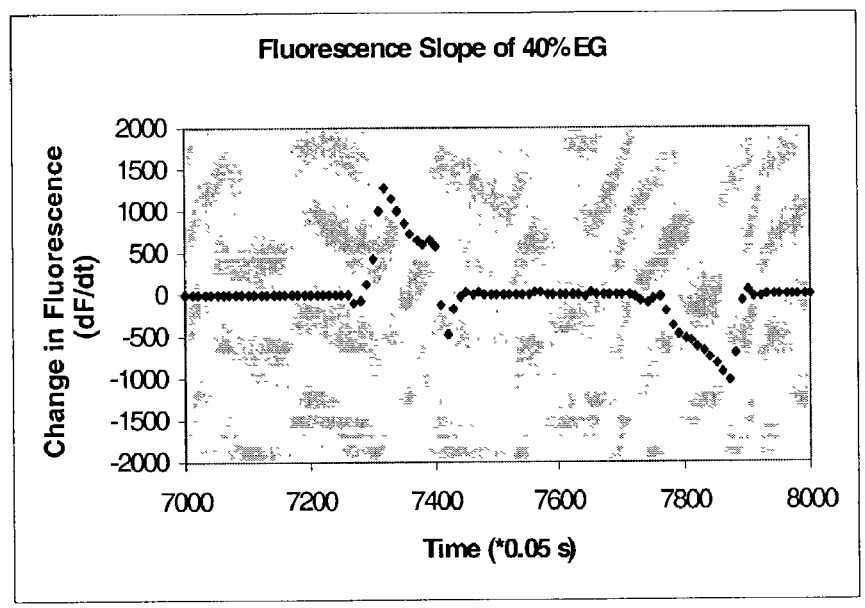
Figure 32:
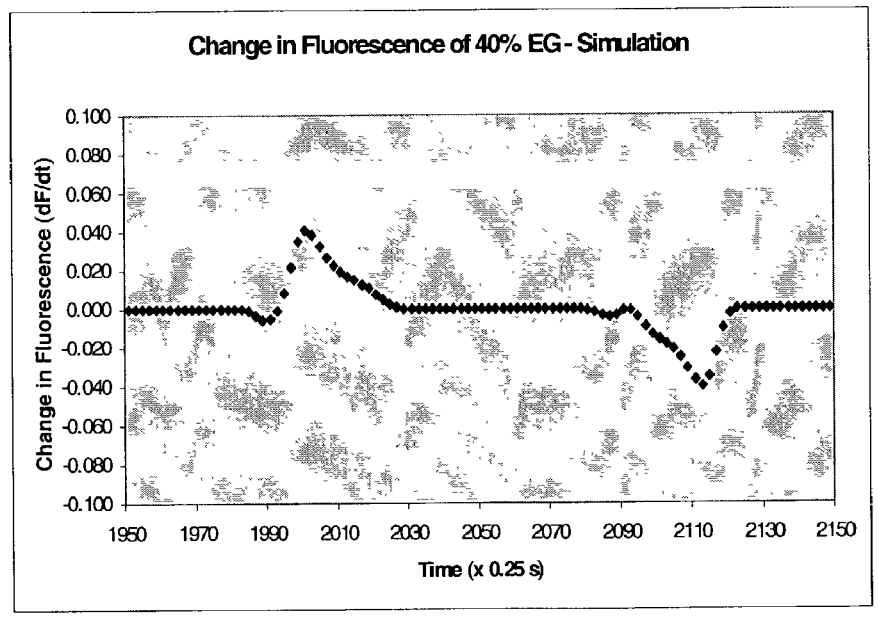

FIGS. 29 and 30 show measurement data and simulation data, respectively, for a single 20-second sip a 10% ethylene glycol solution. The figure shows spontaneous injection of the sample within the capillary due to capillary forces. Viscosity measurements can be based at least in part on the rate of change of the fluorescence (in this case, the increase) when sipping the sample fluid. Measurement data for a rate of change or slope for a 20-second sip of 40% ethylene glycol is shown in FIG. 31, while corresponding simulation data is shown in FIG. 32. The initial change in fluorescence can be the maximum if any errors resulting from spontaneous injection are neglected. These graphs were again generated using the NS71 chip.

Figure 33:
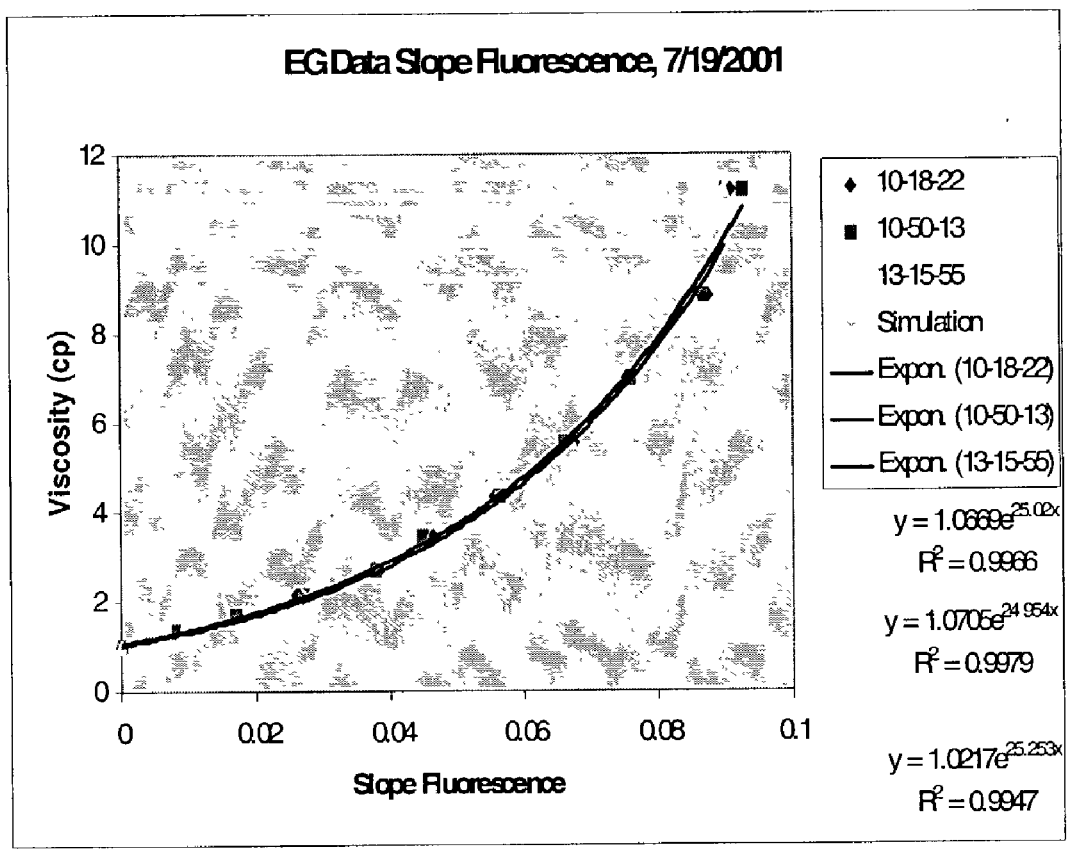
Figure 34A:
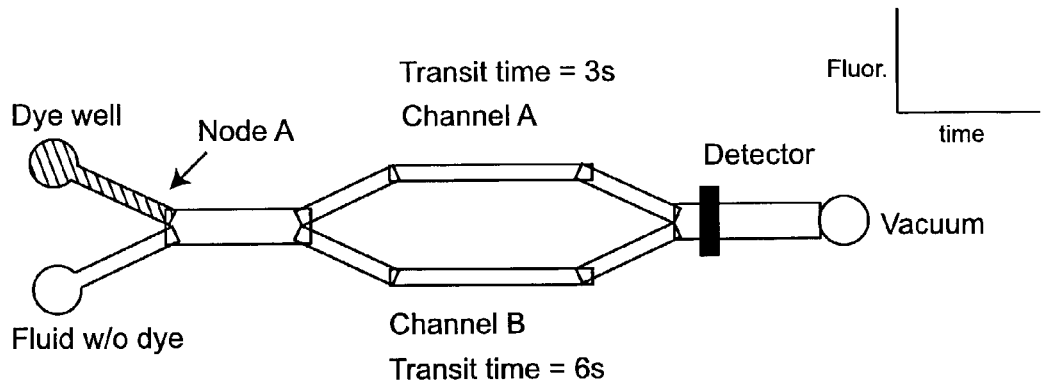
FIGS. 34A to 34F schematically illustrate a pulsed-injection/perturbation method for determination of viscosity.
Figure 34B:
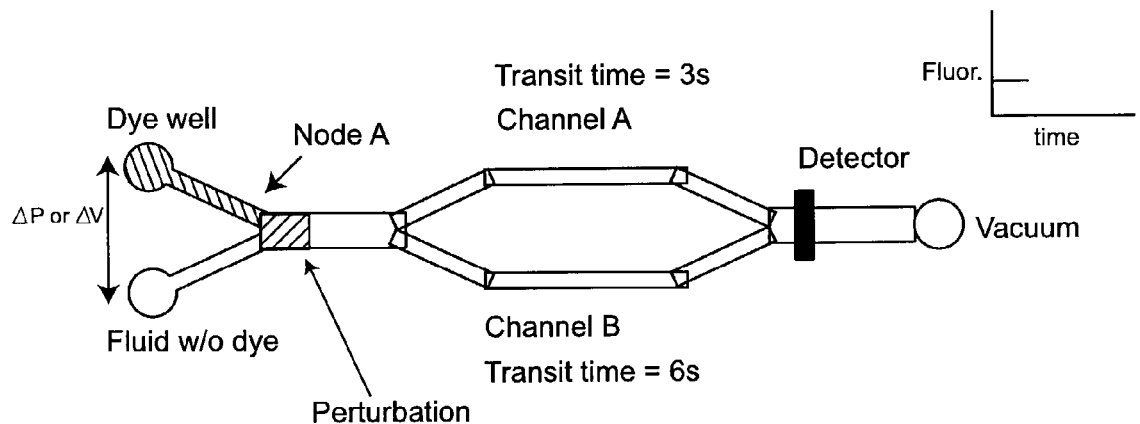
Figure 34C:
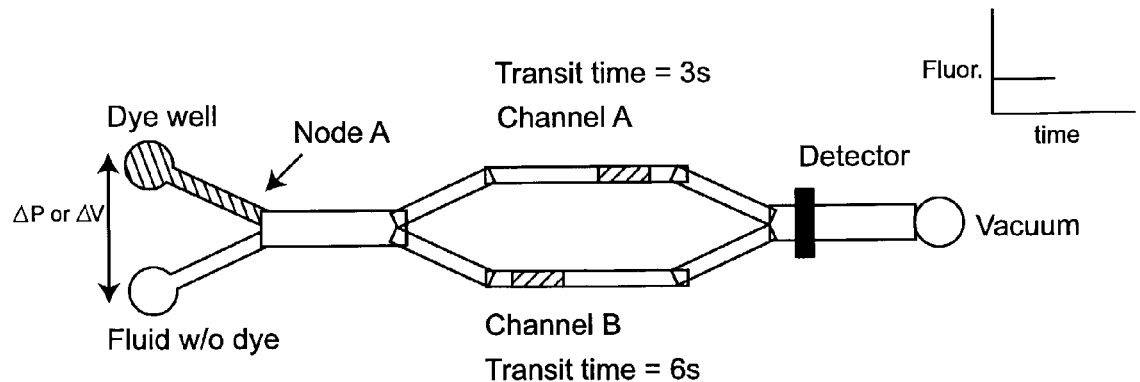
Figure 34D:
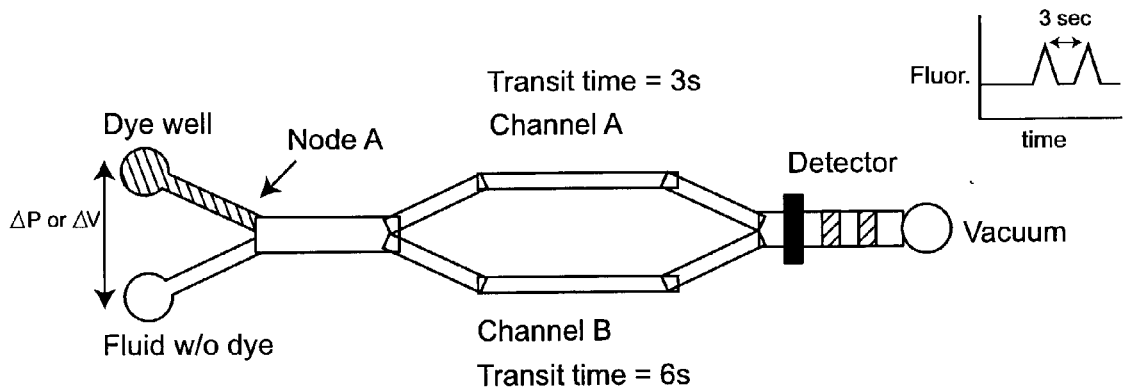
Figure 34E:
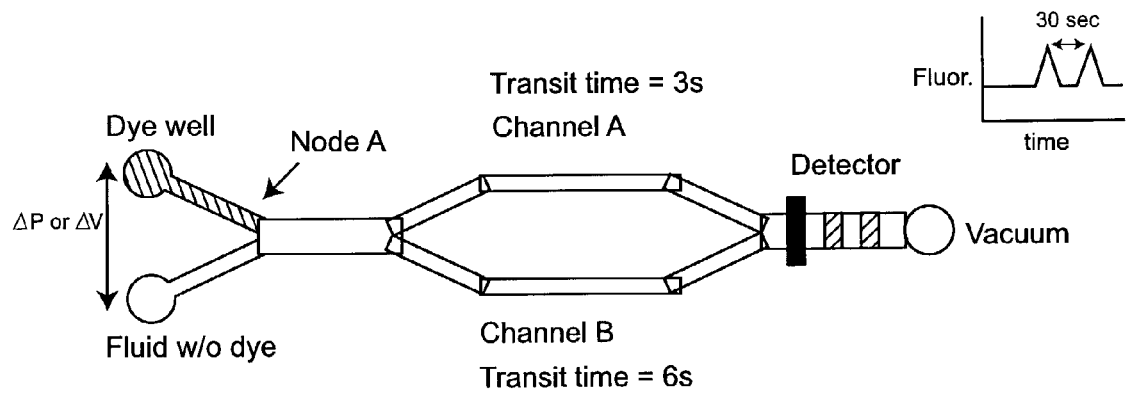
Figure 34F:
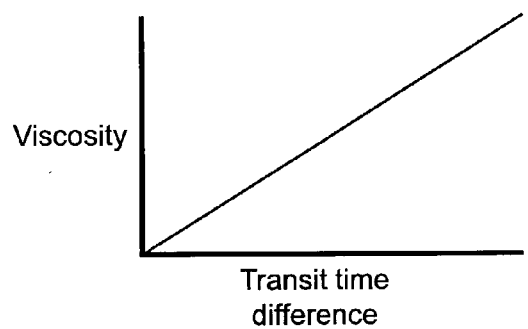

Information from three measurements for the various titrations of ethylene glycol are summarized in FIG. 33. As the viscosities of the samples are known, these measurements allow a calibration curve to be determined for the chip. Measurement data from the calibrated chip can be referenced to the calibration curve to determine viscosity. For example, if a sample material results in a fluorescence slope of 0.06, the curve indicates that the sample material has a viscosity of about 4.5 cp.

Three curves are shown in FIG. 33, with each curve being generated for an associated experiment. The reproducibility of the experiments is indicated by the correspondence of the curves. Sensitivity is higher at the lower viscosities as there is a more significant separation in slopes for a given change in viscosity. Accurate viscosity measurement range can be enhanced by the structures and methods described above. The simulation results deviate somewhat from the measurement data, which can (at least in part) result from actual channel dimensions, channel surfaces, capillary dimensions, capillary/chip joints, and the like, which vary from the computer model.

Techniques are provided in the invention for performing accurate viscosity measurements in which a single perturbation in a detectable signal (e.g., fluorescence intensity) can be used as a signal signature to determine viscosity of a fluid. In overview, a fluid comprising a signal moiety (e.g., a fluorophore) is directed into two or more channels with defined geometries and different hydrodynamic resistance. Based on the relative flow rates of the fluid in the two channels, viscosity can be measured or calculated. Because the method relies on channel geometry rather than applied forces, and because one channel effectively acts to calibrate the other, the method is highly reproducible and reduces errors or "noise" in viscosity measurements.

For example, as illustrated in FIGS. 34A–F, one can design the geometry of first and second microfluidic channel segments (channel A and channel B in FIG. 34) such that they have significantly different flow transit times, allowing a single signal perturbation (e.g., introduction of a detectable marker pulse into the channels) to be split into two signals, e.g., at a channel intersection (node), with the difference in flow time characterizing the viscosity of the fluid. In effect, channel B becomes an internal calibration channel for channel A, to provide signal repeatability of <1% variation over repeated use of a chip with precise control over channel geometry (such as channel length and channel cross section shape). For example, in a T-Junction pulse viscometer (a perpendicular junction is not a requirement of the embodiment, i.e., a T-junction" as used here generically, refers to "T" shapes, "Y" shapes and other similar channel geometries), this reproducibility eliminates errors that arise from the generation of a signal perturbation (e.g., flow of detectable components). This also reduces restrictions on the duration of the pressure or electrokinetic pulse used to produce the signal that is detected.

FIG. 34, panel A illustrates an example microfluidic channel geometry that can be used to perform precise viscosity measurements when using this pulsed-injection/perturbation method. For example, in the illustrated embodiment, the same fluid (e.g., a 1 centipoise fluid ) is loaded throughout the chip, but a reservoir containing the fluid is also spiked with a small amount of fluorescein such that a perturbation in fluorescence signal (resulting from flow of label from the reservoir past a detector) can be produced by inducing a pulse of fluid from the reservoir. The graph to the right of panel A shows the (e.g., fluorescence) readout at the detector. FIG. 34, panel B illustrates the results of a pulse induced via pressure or electrokinetic action ($\Delta V$ or $\Delta P$), as per the T-junction viscometer. For example, under vacuum/hydrodynamic pulse induction, the fluid plug comprising the signal reagent is induced to flow through the chip, e.g., towards vacuum. As shown in FIG. 34, panel C, the pulse is split into two. In this example, because the transit time from channel B is slower than channel A (due to the channel geometry and resultant hydrodynamic resistance), the pulse in channel B arrives later at the detector. In FIG. 34, panel D, the two signal perturbations arrive at the detector, separated, in this illustration, by 3 seconds from each other, resulting in the fluorescence signature shown to the right in the plot. As illustrated in FIG. 34, panel E, for a fluid of 10 cp (10× higher than the previous example) the transit times through the channels are increased proportionally (10× in this example). The transit times for the signal perturbations (e.g., plugs of dye or other detectable materials) are also increased proportionately. As illustrated in FIG. 34., Panel F, the relationship between viscosity and transit time difference is linear. It will be apparent to those skilled in the art that the absolute viscosity of a sample fluid can be determined, e.g., by comparing the transit times of one or more reference standards of known viscosity to sample fluid transit times in the same chip.

In another embodiment, the viscosity of a sample fluid can be determined by evaluation of flow inducing pressures required to set a non-mixed interface at a particular location in a detection channel. This embodiment is based on controlling the location of a non-mixed interface between the two fluids, one typically a reference standard, after they are brought together, e.g., at a T-intersection. Details regarding analytical solutions to Navier-Stokes equations that describe flow of two immiscible incompressible liquids of different constant absolute viscosity in a rectangular channel are found in Gambos and Forster (1998) "An Optical Microfluidic Viscometer" *MEMS* 66:187–191 and in U.S. Pat. No. 6,134,950, "Method for Determining Concentration of a Laminar Sample Stream", to Forster, et al.

In this embodiment, viscosity can be measured by determining the force of flow induction pressures at fluid wells (or other reservoirs) that is required to set the fluid interface at a selected region (e.g., the centerline) of a low-resistance detection channel, downstream of the T intersection. This embodiment can makes use of multi-reservoir pressure control and, e.g., two-layer etch technology (the latter allows the resistance of the channel following the intersection to be made negligible as compared to the channels leading directly to the reference fluid well and the well containing the fluid of unknown viscosity). Flow can be measured by any detection method, including optical detection (e.g., where one or more of the fluid streams are fluorescent), conductivity detection, or the like.

Figure 35:
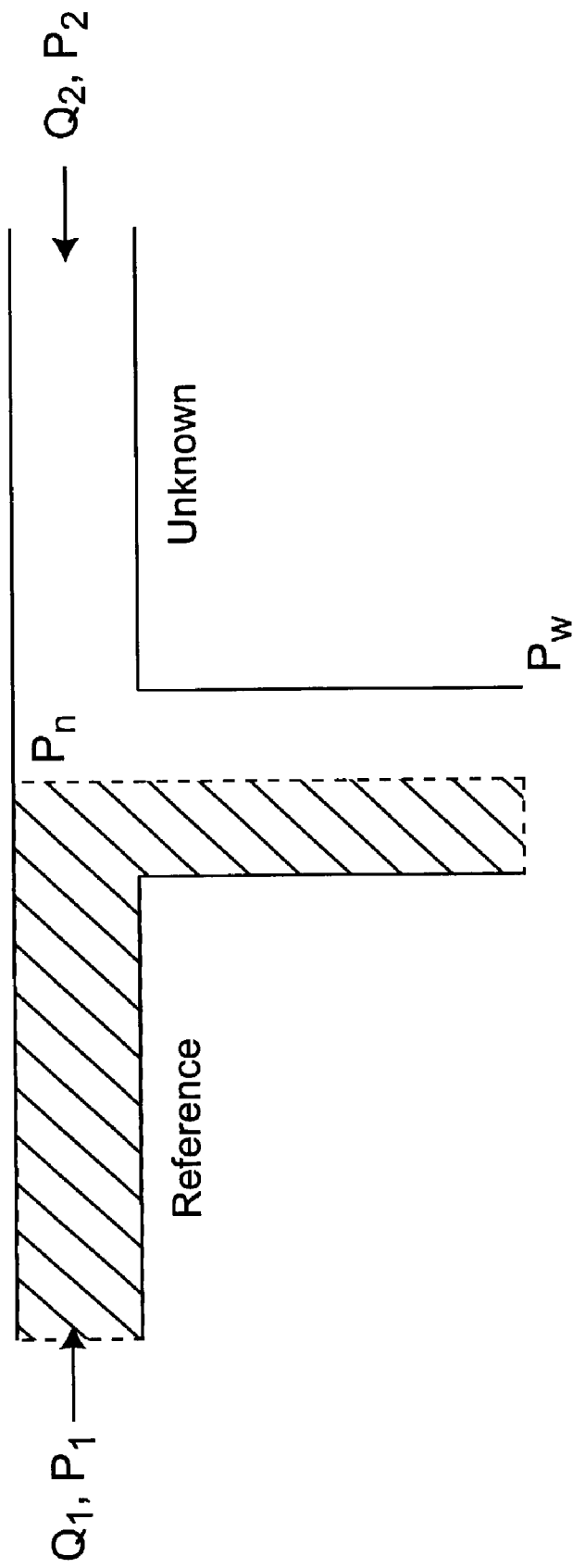
FIG. 35 schematically illustrates a system for determining fluid viscosity using a method of pressure adjustments to a fluid interface location.

As illustrated in FIG. 35, a reference fluid (typically having known viscosity properties) and a fluid comprising properties to be determined are induced to flow simultaneously into a T intersection from channels A and B and into detector channel C. The reference fluid of known viscosity ($\mu_1$) having a flow rate $Q_1$ at pressure $P_1$, and the sample fluid of unknown viscosity having a flow rate of $Q_2$ at pressure $P_2$. Either fluid or both fluids can contain detectable marker as appropriate for the detection method. The pressures ($P_1$ and $P_2$) are adjusted until the interface of the two fluids is positioned at a selected location in the channel (e.g., the centerline). For the condition illustrated in FIG. 35:

$$Q_2/Q_1 = \Delta P_2/\Delta P_1(\mu_1/\mu_2) = f(\mu_2/\mu_1).$$

$$\Delta P_2/\Delta P_1 = (f(\mu_2/\mu_1))/(\mu_2/\mu_1), \text{ where } (\mu_2/\mu_1) = g(\Delta P_2/\Delta P_1).$$

Figure 36:
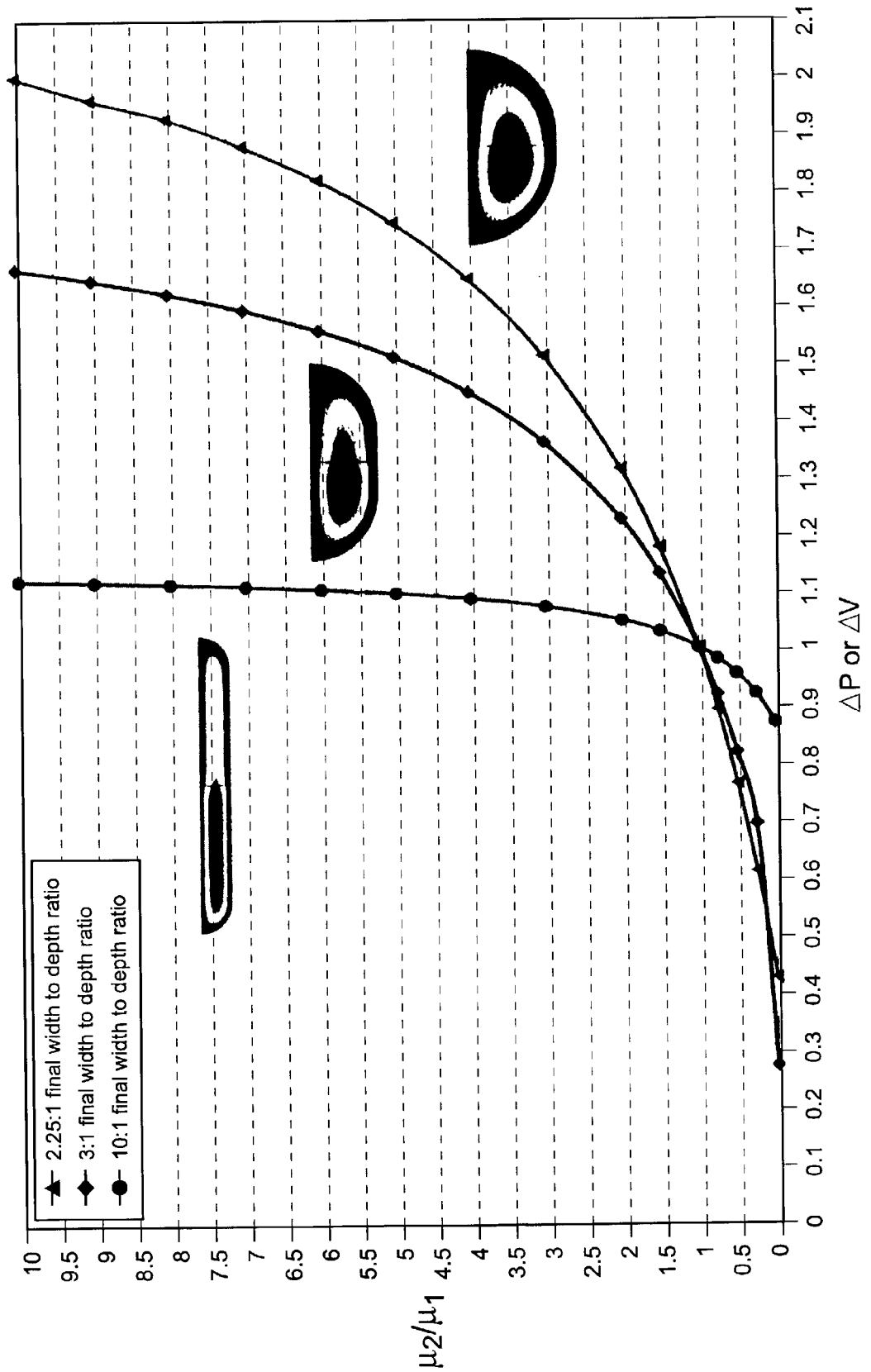
FIG. 36 graphically illustrates calibration curves for interface location fluid viscosity measurement systems having different detection channel aspect ratios.

In general, $\Delta P = P - P_n \approx P$ if the pressure drop between $P_n$ and $P_w$ is negligible. Thus, viscosity can be calculated if the applied pressures to bring the fluid interface to a selected location in channel C are known. For example, as graphically illustrated in FIG. 36, if mass flows are equal, and the interface is located at the centerline of relatively wide channel C (a wide aspect ratio of the channel cross section) the ratio of the pressures required to obtain the centerline interface is approximately equal to the ratios of the fluid viscosities ($P_2/P_1 \approx \mu_2/\mu_1$). Where channel C is relatively deep, the viscosity of a sample fluid can be determined from, e.g., the known reference fluid viscosity and known flow induction pressures with reference to experimentally prepared calibration curves.

In another aspect, the invention provides a chip-based viscometer that allows for the determination of mass-percent composition (the percentage of mass in a fluid mixture that is attributable to any one fluid contributing to the mixture) and kinematic viscosity (dynamic viscosity corrected for mass) of a flowing mixture of two or more fluid streams. The chip utilizes available reference fluid density and viscosity information; the dilution and mixture viscosity are measured simultaneously. The embodiment relies on multi-reservoir pressure control and imaging of a marker front (e.g., fluoroscein, conductive salt solutions, and the like) to set a zero-flow condition on a side channel connecting to the main channel that contains the mixed fluids. Once the zero-flow condition is set, the pressure at the intersection of the side channel and the main channel is equal to the pressure applied to the side-channel well. Thus, a multi-reservoir controller and optical imaging are used to measure the pressure drop in the main channel; the mixture composition and viscosity is determined from the measured pressure drop and the pressures applied to the fluid wells.

The invention provides a chip-based viscometer that allows for the determination of mass-percent composition (the percentage of mass in a fluid mixture attributable to any one contributing fluid stream) and kinematic viscosity (dynamic viscosity corrected for mass) of a flowing mixture of two or more fluid streams. The chip utilizes available information of reference fluid densities and viscosities; the dilution and mixture viscosity are measured simultaneously. The embodiment relies on multi-reservoir pressure control and imaging of a marker front (e.g., fluoroscein, conductive salt solutions, and the like) to set a zero-flow condition on a side channel connecting to the main channel that contains the mixed fluids. Once the zero-flow condition is set, the pressure at the intersection of the side channel and the main channel is equal to the pressure applied to the side-channel well. Thus, a multi-reservoir controller and optical imaging are used to measure the pressure drop in the main channel; the mixture composition and viscosity is determined from the measured pressure drop and the pressures applied to the fluid wells.

Figures 37A, 37B:
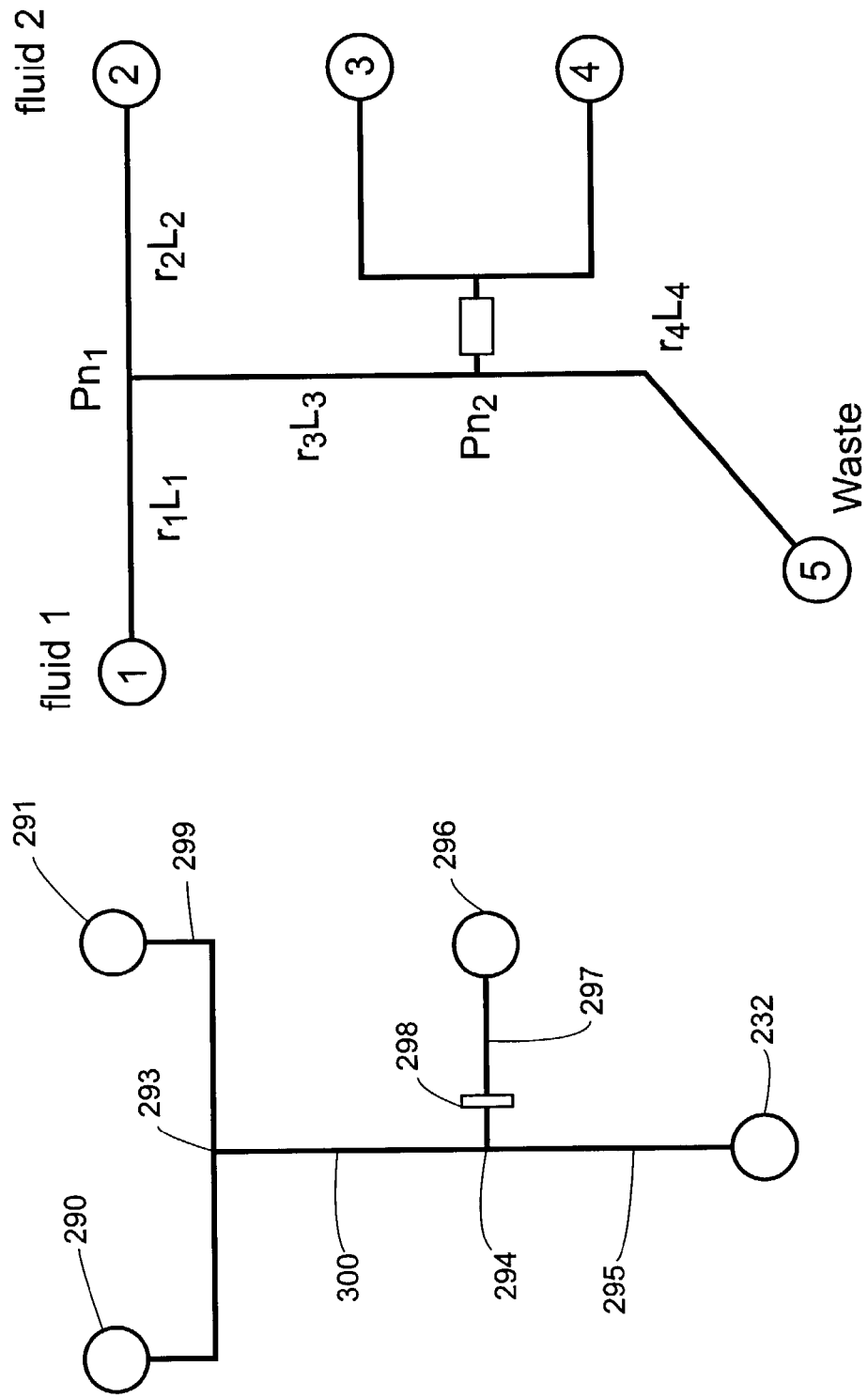
FIGS. 37A–37B schematically illustrate systems for determining mass-percent composition and kinematic viscosity of fluids.

For example, to simultaneously measure mass-percent composition and kinematic viscosity, a microfluidic chip, as shown schematically in FIG. 37A, can be employed. Fluid well 290 can contain, e.g., a first fluid of known kinematic viscosity and second fluid well 291 can contain a second fluid of known kinematic viscosity. The wells can be independently pressurized (e.g., using a multi-reservoir pressure control manifold) to provide desired fluid flows into mixing node 293, past side channel node 294, and along main channel section 295 to waste well 232. Side channel well 296, containing, e.g., a detectable marker, such as a dye reagent or salt solution, can be pressurized to create a marker front along side channel 297 that can be detected by detector 298. The pressure in side channel well 296 can be adjusted to a level equivalent to the pressure at side channel node 294 as confirmed by detection of a stationary marker front (the pressure at the node then measurable as the pressure in the side channel well). A stable dynamic flow is thus created, e.g., wherein the mass-percent composition for each fluid and the kinematic viscosity of the fluid mixture can be calculated.

Calculations for the system described above can be based on the momentum equation for a fully developed flow of an incompressible liquid, given by:

$$\Delta P = m v r L, \text{ or}$$

$$v = \Delta P / m r L$$

where kinematic viscosity (v) of a fluid is equal to the pressure differential (ΔP) of the fluid flowing in a channel segment divided by the product of the fluid mass flow rate (m), the channel resistance shape factor (r), and the channel length (L). In well characterized systems, many of these parameters are well known, e.g., from theoretical calculations and experimentation. In the system of FIG. 37A, for example, the kinematic viscosity (v) of a mixed fluid in main channel section 295 can be calculated after determining the pressure differential between side channel node 294 ($P_{294}$, measured at well 296 under zero-flow side channel conditions) and waste well 232 ($P_{232}$, typically constant, and often 0 psig). Once $P_{294}$ is known, $P_{293}$ can be calculated, e.g., from the known resistance ratios of channel segment 295 and channel segment 300:

$$P_{293} = (P_{294} - P_{232})(r_{300} L_{300} + r_{295} L_{295}) / (r_{295} L_{295}) + P_{323}$$

Once $P_{293}$ is calculated, the mass flow rate from well 291 ($m_{291}$) can be calculated, e.g., using the calculated $P_{293}$ and the known (or previously determined) properties $r_{299}$, $L_{299}$, and $v_{291}$:

$$m_{291} = (P_{291} - P_{293}) / (v_{291} \times r_{299} \times L_{299})$$

The mass flow rate from well 290 can be calculated in a similar manner and the total mass flow rate in channel 300 (which is the same as that in channel 295 under the zero-flow condition) is calculated as:

$$m_{300} = m_{295} = m_{290} + m_{291}$$

The kinematic viscosity can then be calculated as the pressure differential between side-channel node 294 and well 232 divided by the product of the total mass flow ($m_{295}$) and the resistance along main channel segment 295 ($r_{295} \times L_{295}$). That is:

$$v_{295} = (P_{294} - P_{232}) / (m_{295} \times r_{295} \times L_{295})$$

The composition of a fluid mixture (percentage of each comprising fluid, m %) can be calculated from quantities that were determined or calculated in the manner described above:

$$m\%_{299} = m_{299} / m_{295}$$

By varying the pressures on wells 290 and 291, and then determining the mixture composition and viscosity, a curve can be generated that describes kinematic viscosity of the fluid mixture versus mass-percent composition (e.g. $v_{295}$ versus m $\%_{299}$).

The pressure of fluid at any location along a channel can be measured, e.g., at a side channel fluid well where the side channel flow has been set to zero-flow. The zero-flow condition can also be determined using, for example, an electrical conductivity/resistance measurement. Such a measurement can be performed using a system, e.g., similar to that shown schematically in FIG. 37b. In this case, wells 3 and 4 can be filled, e.g., with a fluid having an electrical conductivity much higher (or lower) than the fluids in wells 1 or 2. To determine the zero-flow condition, the same pressure can be applied at wells 3 and 4 and this pressure can be, e.g., adjusted while the electrical resistance of the side channel is simultaneously measured (e.g. by sending a DC or AC current from well 3 to well 4 and measuring the resulting voltage differential). Given the conductivity mismatch of the fluids in wells 1 and 2 with those of wells 3 and 4, flow into or out of the side channel will cause a change in electrical resistance between wells 3 and 4. When the flow in the side channel is stopped, the electrical resistance of the side channel will remain constant, indicating a zero-flow condition in the side channel. The pressure applied to wells 3 and 4, in this case is, e.g., an indirect measure of fluid pressures ($Pn_2$) at the intersection of the side channel with the main channel.

Figure 38:
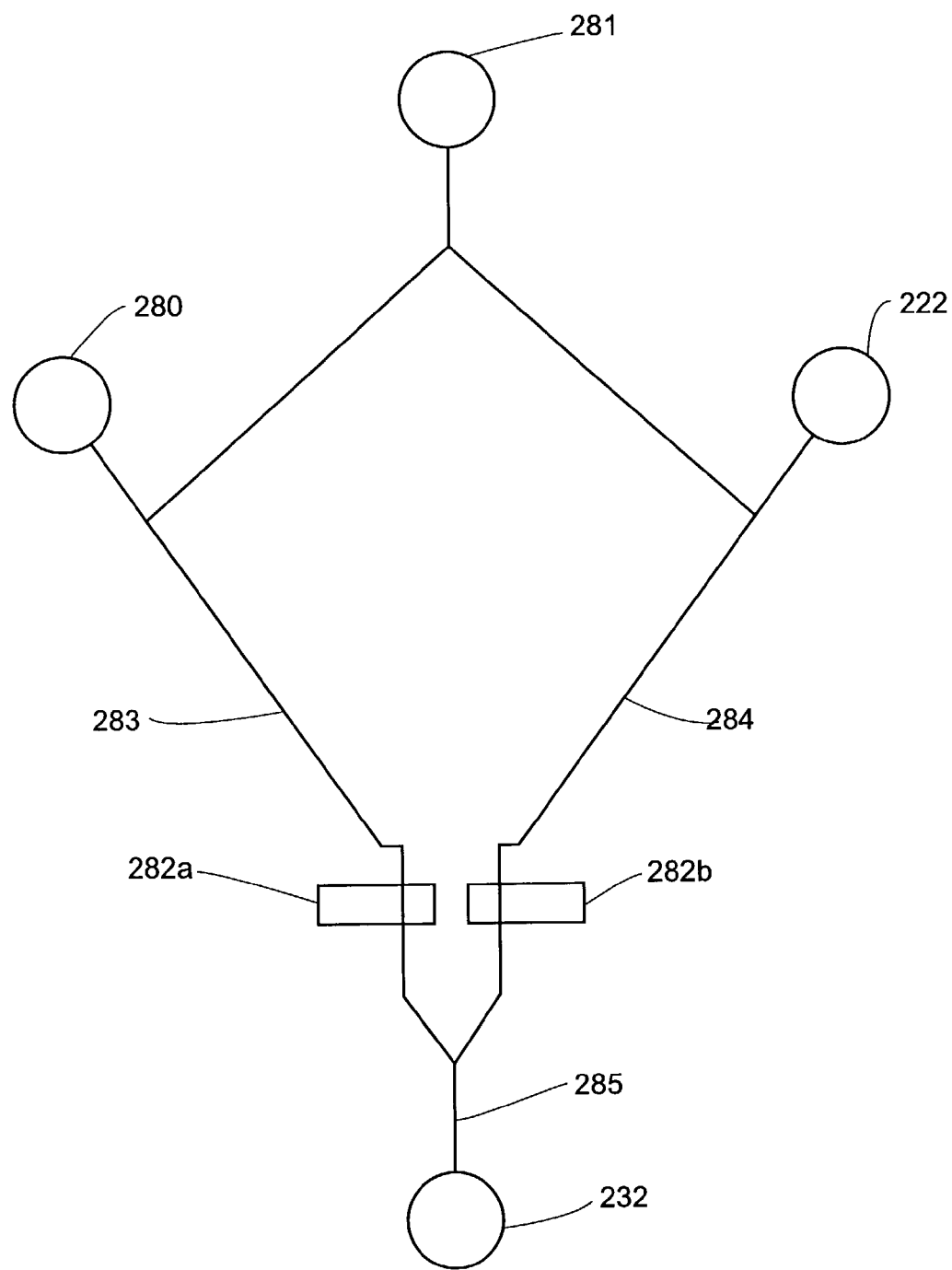
FIG. 38 schematically illustrates a system with paired channel geometry and a common detectable marker diluent fluid source for determination of fluid viscosities.

In further embodiments of viscometers of the invention, a chip can include, e.g., paired channel geometry to provide an internal standard for channel etch depth and temperature compensation. Such a chip, as shown in FIG. 38, can be used to determine the viscosity of an unknown sample relative to a reference fluid of known viscosity. For example, reference fluid well 280 can contain a reference fluid of known viscosity and sample fluid source well 222 can contain a sample fluid with a viscosity to be determined. A diluent fluid, e.g., containing a detectable marker, such as a dye, can be contained in diluent fluid well 281. Each of the three wells can be equally pressurized, e.g., with a multi-reservoir pressure manifold, to induce fluids to flow into waste well 232. After fluid flows have stabilized, the difference in amounts of diluent fluid (detectable marker) at detectors 282a and 282b can be determined. If the sample fluid viscosity is higher than the reference fluid viscosity, more diluent fluid containing detectable marker will flow into reference channel 283. The sample fluid viscosity can be determined by, e.g., calculation, or by reference to an experimentally generated calibration curve of measured dye ratios for the reference and known sample calibration reagents.

Sample fluid viscosity can optionally be compared to reference fluid viscosity using the paired channel configuration of FIG. 38, e.g., by measurement of a time difference output value for a detectable marker pulse traveling in the paired channels (typically having equivalent volume and resistance). For example, the three fluid wells can be equally pressurized to establish a stable flow. A pressure pulse can be exerted on diluent well 281 to inject a detectable marker pulse in the flow of channels 283 and 284. If the sample fluid is less viscous than the reference fluid, the pulse will arrive, e.g., at detector 282b before detector 282a. The sample fluid viscosity can be determined by, e.g., calculation, or by reference to an experimentally generated calibration curve of measured pulse travel time differences between the reference and sample calibration reagents of known viscosity. For this viscosity measurement technique, a single detector, e.g., at waste channel 285, can be optionally used to detect the reference and sample pulse, as can be appreciated by those skilled in the art.

Sample fluid viscosity can optionally be compared to reference fluid viscosity using the paired channel configuration of FIG. 38, e.g., by measurement of a pressure differential output value necessary to obtain equivalent flow rates in the paired channels. For example, the three fluid wells can be equally pressurized to establish stable fluid flows. A pressure pulse can be exerted on diluent well 281 to inject a detectable marker pulse in the flow of channels 283 and 284. If the sample fluid is more viscous than the reference fluid, the pulse will arrive, e.g., at detector 282a before detector 282b. The pressure inducing flow from sample fluid well 222 can then be, e.g., increased, and a second marker pulse introduced into the fluid flows. If the pulse arrives, e.g., at detector 282a again before the pulse at detector 282b, the pressure inducing flow from sample fluid well 222 can be increased further before another pulse timing measurement. After repeated pulse timing and pressure adjustment cycles, e.g., a pressure differential between reference well 280 and sample well 222 can be determined which provides equivalent travel times for pulses in channels 283 and 284. The sample fluid viscosity can be determined by, e.g., calculation, or by reference to an experimentally generated calibration curve of measured pressure differences required to obtain equivalent pulse travel times between the reference and a set of sample calibration reagents of known viscosity. Simple programs can be written, e.g., in Matlab to measure the arrival time of pulses in the chip channel and to iteratively adjust the chip well pressures.

In an additional embodiment, the invention provides methods for measuring viscoelasticity (relaxation time) of polymers such as biopolymers, ordered or disordered micellar solutions and/or surfactants in a microfluidic system. The method operates by measuring the transient response of a test fluid that is following through a micro channel under the action of an applied sinusoidal pressure gradient of frequency $\omega$.

Figure 39:
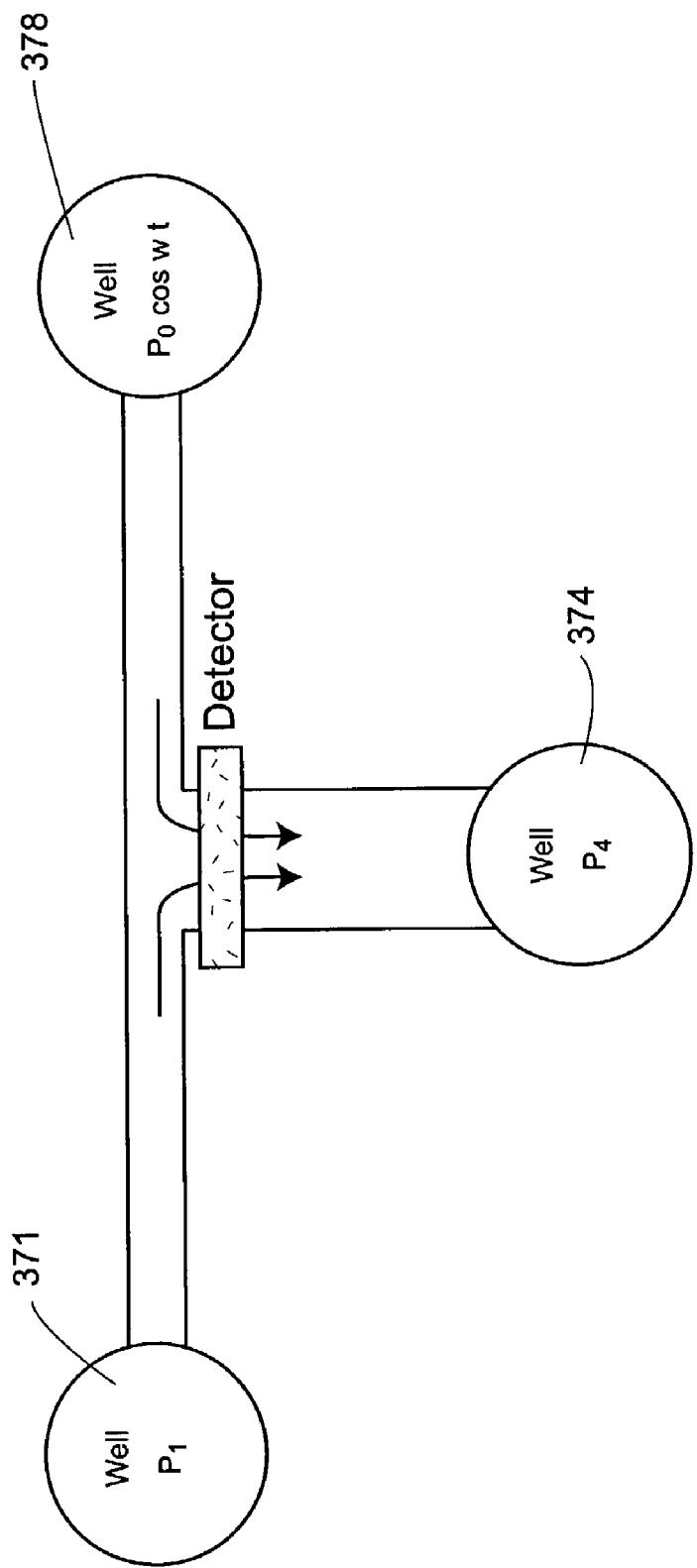
FIG. 39 schematically illustrates a system for determining fluid viscoelasticity.

For example, a simple T-junction chip is used to illustrate this approach in FIG. 39. Although a perpendicular intersection alignment is preferred in this invention, other geometries can be employed. A detectable marker labeled Newtonian fluid (such as fluorescein in a low concentration buffer solution) is loaded in well #371, a polymeric sample fluid is loaded in well #378, and both fluids are mixed at the T-junction and induced to co-flow towards waste well #374. The dilution ratio of the fluids depends upon the applied pressure of wells 371 and 378 (pressure at well 374 can, e.g., =0 psi). If the flow inducing pressure at well #378 is made to oscillate as: $p=p_o \cos\omega t$, the dilution ratio of the polymeric sample fluid can be shown to oscillate as $Q_{378}/Q_{371} \sim a p_o \{(1+b\lambda\omega^2)\cos\omega t - (\lambda-c)\omega \sin\omega t\}$ where a, b and c are dimensional constants, $Q_{378}/Q_{371}$ represents the ratio of sample fluid and Newtonian fluid mass flows, and $\lambda$ is the relaxation time of the test polymeric fluid. Hence, if the detector is located near the T-junction, it will register a sinusoidally varying signal (oscillations in the amount of detectable marker) with an additional phase shift associated with the time constant $\lambda$. This signal can then be compared with the input pressure oscillation to determine the phase shift. The phase shift value can be used in a calculation of the test polymeric material viscoelasticity. For a simple Newtonian fluid, the pressure and detector signal will be out of phase ($\lambda=0$ s). Various time scales in the flow of the polymeric solutions can be probed using a spectrum of pressure frequencies.

There are a number of applications for this method. For example, this method can determine the viscoelasticity (relaxation times) of polymeric solutions such as long chain biopolymers, lipids, entangled wormy micellar solutions (see, FIG. 40 for a schematic diagram of micellar system phase changes that can affect viscoelasticity), liquid crystals, vesicles and spherical micelles. These systems tend to change their viscoelastic behavior with concentration, temperature and ionic strength (if an amphiphilic molecule is charged). Hence, the effects of the parameters can be easily probed using a transient microchip. For example, a solution of 15 mM cetylpyridinium salicylate in the presence of 11 mM sodium salicylate has a relaxation time of ~1 s. Upon increasing the ionic strength by 14%, the relaxation time of the resulting solution increases by two orders of magnitude (~100 s) (Rehage and Hoffman, Journal of Physical Chemistry, 92, 4712, 1988). The structure and state of aggregation of concentrated ionic surfactants in electrolytic solutions can also be inferred from these measurements.

It should be understood that the various embodiments of methods and structures described herein will often be combined. For example, dilution and/or fluid combination structures and methods can be combined in a microfluidic network with viscometer structures and methods, allowing fluid mixtures to be characterized as a function of their composition. Mixtures will often include more than two fluids, and the ability to controllably mix three or more, five or more, and/or ten or more fluids in a controlled manner within the network allows complex studies to be performed quickly and with small fluid volumes. Measured fluid flow, measured flow times, and/or viscometry information derived from the network will, as noted above, often by used by the fluid flow generator control system to control the flow of fluids within the network via a feedback control loop. Similarly, computer simulations of networks can be combined with flow times and other flow measurement data to enhance feedback control of flows within the network.

While the viscosity measurement structures described herein have generally, for purposes of illustration, made use of pressure differential, similar microfluidic systems might make use of other flow generating systems within a microfluidic environment for determining viscosities of small quantities of sample fluids. In general, while the exemplary embodiments have been described in some detail, by way of example and for clarity of example, a variety of modifications, changes, and adaptation will be obvious to those of skill in the art. Hence, the scope of the present invention is limited solely by the appended claims.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for determining a relative viscosity of a sample fluid and a reference fluid, the method comprising:
   (a) establishing a steady flow of the reference fluid through two microfluidic channel segments of different hydrodynamic resistance, a first microfluidic channel segment and a second microfluidic channel segment, each of the two microfluidic channel segments having an inlet and an outlet;
   (b) introducing a detectable perturbation into the steady flow of reference fluid at the inlet of each of the two microfluidic channel segments at a first time;
   (c) measuring a first transit time that transpires from the first time until the detectable perturbation exits the outlet of the first microfluidic channel segment;
   (d) measuring a second transit time that transpires from the first time until the detectable perturbation exits the outlet of the second microfluidic channel segment;
   (e) calculating a difference in the first and second transit times for the reference fluid;
   repeating steps (a)–(e) with a sample fluid, thereby determining a difference in the first and second transit times for the sample fluid; and
   determining a relative viscosity of the sample fluid by comparing the difference in the first and second transit times for the reference fluid and the difference in the first and second transit times for the sample fluid.

2. The method of claim 1, further comprising:
   determining an absolute viscosity of the sample fluid by;
   determining the difference in first and second transit times for a plurality of reference fluids, wherein the difference in first and second transit times for the sample fluid lies within the range of the various differences in first and second times for the plurality of reference fluids, and
   comparing the difference in first and second transit times for the sample to the various differences in first and second times for the plurality of reference fluids.

3. The method of claim 1, wherein the inlets of the first microfluidic channel segment and the second microfluidic channel segment meet at a "Y" junction.

4. The method of claim 1, wherein the inlets of the first microfluidic channel segment and the second microfluidic channel segment meet at a "T" junction.

5. The method of claim 1, wherein the step of flowing the sample fluid through two microfluidic channel segments comprises applying a pressure difference across the two microfluidic channel segments.

6. The method of claim 1, wherein the step of flowing the sample fluid through two microfluidic channel segments comprises applying an electrokinetic driving force across the two microfluidic channel segments.

7. The method of claim 1, wherein the detectable perturbation comprises a perturbation in a fluorescence signal.

8. The method of claim 7, wherein the perturbation in a fluorescence signal comprises an increase in fluorescence.

* * * * *